US006828397B2

(12) United States Patent
Boussie et al.

(10) Patent No.: US 6,828,397 B2
(45) Date of Patent: Dec. 7, 2004

(54) METHODS OF COPOLYMERIZING ETHYLENE AND ISOBUTYLENE AND POLYMERS MADE THEREBY

(75) Inventors: Thomas R. Boussie, Menlo Park, CA (US); Gary M. Diamond, San Jose, CA (US); Christopher Goh, San Francisco, CA (US); Keith A. Hall, San Jose, CA (US); Anne M. LaPointe, Sunnyvale, CA (US); Margarete K. Leclerc, Santa Clara, CA (US); Cheryl Lund, Milpitas, CA (US); Vince Murphy, Campbell, CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 0 days.

(21) Appl. No.: 09/992,760

(22) Filed: Nov. 6, 2001

(65) Prior Publication Data

US 2002/0137845 A1 Sep. 26, 2002

Related U.S. Application Data

(60) Provisional application No. 60/301,666, filed on Jun. 28, 2001, and provisional application No. 60/246,781, filed on Nov. 7, 2000.

(51) Int. Cl.[7] .............................. C08F 4/44; C08F 4/72; B01J 31/38
(52) U.S. Cl. ................ 526/161; 526/171; 526/336; 526/348.6; 502/155; 502/167; 546/2; 548/101; 548/402
(58) Field of Search .................. 526/348.6, 336, 526/161, 171; 502/155, 167

(56) References Cited

U.S. PATENT DOCUMENTS

| | | | |
|---|---|---|---|
| 4,297,465 A | 10/1981 | Smith | 526/141 |
| 5,026,798 A | 6/1991 | Canich | 526/127 |
| 5,064,802 A | 11/1991 | Stevens et al. | 502/155 |
| 5,153,157 A | 10/1992 | Hlatky et al. | 502/117 |
| 5,318,935 A | 6/1994 | Canich et al. | 502/117 |
| 5,385,993 A | 1/1995 | Fujita | 526/119 |
| 5,453,410 A | 9/1995 | Kolthammer et al. | 502/155 |
| 5,599,761 A | 2/1997 | Turner | 502/152 |
| 5,616,664 A | 4/1997 | Timmers et al. | 526/127 |
| 5,631,391 A | 5/1997 | Canich | 556/11 |
| 5,637,660 A | 6/1997 | Nagy et al. | 526/160 |
| 5,763,556 A | 6/1998 | Shaffer et al. | 526/348.4 |
| 5,866,665 A | 2/1999 | Shaffer et al. | 526/348.4 |
| 5,985,356 A | 11/1999 | Schultz et al. | 427/8 |
| 6,030,917 A | 2/2000 | Weinberg et al. | 502/104 |
| 6,034,240 A | 3/2000 | La Pointe | 546/24 |
| 6,043,363 A | 3/2000 | LaPointe et al. | 544/225 |
| 6,103,657 A | 8/2000 | Murray | 502/155 |
| 6,136,748 A | * 10/2000 | Smith | 502/167 |
| 6,214,939 B1 | 4/2001 | Shinozaki et al. | 525/270 |
| 6,239,236 B1 | 5/2001 | Morini et al. | 526/124.9 |
| 6,260,407 B1 | 7/2001 | Petro et al. | 73/61.52 |

FOREIGN PATENT DOCUMENTS

| | | | |
|---|---|---|---|
| EP | 0 277 004 A1 | 8/1988 | ............ C08F/4/64 |
| EP | 0 622 380 | 11/1994 | ........... C08F/10/06 |
| EP | 0 748 824 | 12/1996 | ........... C08F/10/06 |
| EP | 0 889 061 A1 | 10/1999 | ............ C08F/4/64 |
| EP | 1 041 092 | 10/2000 | ......... C08F/210/02 |
| EP | 1 195 391 | 4/2002 | .......... C98F/110/06 |
| GB | 1 340 694 | 12/1973 | ............ C08F/3/08 |
| JP | 00 239313 | 9/2000 | |
| JP | 01 011111 | 1/2001 | ............ C08F/4/64 |
| JP | 01 048909 | 2/2001 | ............ C08F/4/64 |
| JP | 01 048910 | 2/2001 | ............ C08F/4/64 |
| JP | 01 048911 | 2/2001 | ............ C08F/4/64 |
| JP | 01 048925 | 2/2001 | ........... C08F/10/00 |
| JP | 01 048936 | 2/2001 | |
| JP | 01 181331 | 7/2001 | ........... C08F/4/642 |
| WO | WO 93/05082 | 3/1993 | ........... C08F/10/06 |
| WO | WO 93/25590 | 12/1993 | ........... C08F/10/00 |
| WO | WO 94/00500 | 1/1994 | ........... C08F/10/00 |
| WO | WO 98/03521 | 1/1998 | ........... C07F/19/00 |
| WO | WO 98/10014 | 3/1998 | ........... C08L/23/02 |
| WO | WO 98/22514 | 5/1998 | ............ C08F/2/00 |
| WO | WO 99/01460 | 1/1999 | |
| WO | WO 99/05186 | 2/1999 | ........... C08F/10/00 |
| WO | WO 99/06413 | 2/1999 | ............ C07F/5/02 |
| WO | WO 99/29742 | 6/1999 | ........... C08F/10/06 |
| WO | WO 99/42467 | 8/1999 | ............ C07F/5/02 |
| WO | WO 00/09255 | 2/2000 | ............ B01J/19/00 |
| WO | WO 00/20427 | 4/2000 | |
| WO | WO 00/37511 | 6/2000 | |
| WO | WO 00/50470 | 8/2000 | ............ C08F/4/70 |
| WO | WO 01/30862 | 5/2001 | |
| WO | WO 01/40325 | 6/2001 | |
| WO | WO 01/40330 | 6/2001 | |

OTHER PUBLICATIONS

Kang, Kap Ku et al., "The Synthesis and Polymerization Behavior of Bimetallic Pyridine Diamide Complexes Containing Transition Metal", *J. Polym. Sci.*, Part A: Polym. Chem., 1999, 37(20), pp. 3756–3762.

Ziniuk, Zeev et al., "Zirconium Complexes of Chelating Dianionic Bis (Pentafluorophenylamido) Ligands: Synthesis, Structure and Ethylene Polymerization Activity", *Inorg. Chem. Commun.*, 1999, 2(11), pp. 549–551.

Bercaw et al., *J. Am. Chem. Soc.*, 1996, vol. 118, 11988–11989.

(List continued on next page.)

*Primary Examiner*—Robert Deshon Harlan
(74) *Attorney, Agent, or Firm*—Venable LLP; Marina V. Schneller

(57) ABSTRACT

New ligands, compositions, metal-ligand complexes and arrays with pyridyl-amine ligands are disclosed that catalyze the polymerization of monomers into polymers. Certain of these catalysts with hafnium metal centers have high performance characteristics, including higher comonomer incorporation into ethylene/olefin copolymers, where such olefins are for example, 1-octene, isobutylene or styrene. Certain of the catalysts are particularly effective at polymerizing propylene to high molecular weight isotactic polypropylene in a solution process at a variety of polymerization conditions.

10 Claims, 7 Drawing Sheets

OTHER PUBLICATIONS

Bercaw et al., J. Am. Chem. Soc., 1999, vol. 121, 564–573.
Brintzinger et al., Angew. Chem. Int. Ed. Engl., 1995, vol. 34, pp. 1143–1170.
Coates et al., Angew. Chem. Int. Ed., 2000, vol. 39, pp. 3626–3629.
Coates, G.W., Chem. Rev. 2000, 100, 1223–1252.
Gibson et al., Angew. Chem. Int. Ed., 1999, vol. 38, pp. 428–447.
Jordan, Adv. Organometallic Chem., 1991, vol. 32, pp. 325–153.
LaPointe et al., J. Am. Chem. Soc., 2000, 122, 9560–9561.
Luongo, J.P., J. Appl. Polym. Sci., 1960, 3, 302–309.
Organometallics, 1999, 18, pp. 3649–3670.
Piers et al., J. Am. Chem. Soc., 1999, 121, 3244–3245.
Resconi et al., Chem. Rev. 2000, 100, 1253–1345.
Sundell, T. et al., Polymer, 1996, 37, 3227–3231.

* cited by examiner

METHODS OF COPOLYMERIZING ETHYLENE AND ISOBUTYLENE AND POLYMERS MADE THEREBY

This application claims the benefit of U.S. Provisional Patent Application No. 60/246,781, filed Nov. 7, 2000 and the benefit of U.S. Provisional Patent Application No. 60/301,666, filed Jun. 28, 2001, both of which are incorporated herein by reference for all purposes.

FIELD OF THE INVENTION

The present invention relates to ligands, complexes, compositions and/or catalysts that provide enhanced olefin polymerization capabilities based on a substituted pyridyl amine structure and hafnium. The invention also relates to methods of polymerization. The invention also relates to isotactic polypropylene and methods of preparing isotactic polypropylene.

BACKGROUND OF THE INVENTION

Ancillary (or spectator) ligand-metal coordination complexes (e.g., organometallic complexes) and compositions are useful as catalysts, additives, stoichiometric reagents, monomers, solid state precursors, therapeutic reagents and drugs. Ancillary ligand-metal coordination complexes of this type can be prepared by combining an ancillary ligand with a suitable metal compound or metal precursor in a suitable solvent at a suitable temperature. The ancillary ligand contains functional groups that bind to the metal center(s), remain associated with the metal center(s), and therefore provide an opportunity to modify the steric, electronic and chemical properties of the active metal center(s) of the complex.

Certain known ancillary ligand-metal complexes and compositions are catalysts for reactions such as oxidation, reduction, hydrogenation, hydrosilylation, hydrocyanation, hydroformylation, polymerization, carbonylation, isomerization, metathesis, carbon-hydrogen activation, carbon-halogen activation, cross-coupling, Friedel-Crafts acylation and alkylation, hydration, dimerization, trimerization, oligomerization, Diels-Alder reactions and other transformations.

One example of the use of these types of ancillary ligand-metal complexes and compositions is in the field of polymerization catalysis. In connection with single site catalysis, the ancillary ligand typically offers opportunities to modify the electronic and/or steric environment surrounding an active metal center. This allows the ancillary ligand to assist in the creation of possibly different polymers. Group 4 metallocene based single site catalysts are generally known for polymerization reactions. See, generally, "Chemistry of Cationic Dicyclopentadienyl Group 4 Metal-Alkyl Complexes", Jordan, *Adv. Organometallic Chem.*, 1991, Vol. 32, pp. 325–153 and "Stereospecific Olefin Polymerization with Chiral Metallocene Catalysts", Brintzinger, et al., *Angew. Chem. Int. Ed. Engl.*, 1995, Vol. 34, pp. 1143–1170, and the references therein, all of which is incorporated herein by reference.

However, those of skill in the art of single site catalysis appreciate that there may be substantial differences in performance between different metal centers. For example, U.S. Pat. No. 5,064,802 discloses a broad category of monocyclopentadienyl ligand catalysts with a broad disclosure of useful metals, and U.S. Pat. No. 5,631,391 more specifically discloses that titanium metal centers offer performance advantages with respect to the same or similar ligands. Additionally, Coates, et al., *Angew. Chem. Int. Ed.*, 2000, vol. 39, pp. 3626–3629 describes the unpredictable nature of olefin polymerization catalyst structure-activity relationships. Thus, references that describe, for example, groups 3–13 and the lanthanides, for example in U.S. Pat. No. 6,103,657, are not of adequate performance indicators of all that is within the scope of what is allegedly described. Moreover, as those of skill in the art appreciate, differences in ligand substituents typically polymerize different monomers at different performances under different polymerization conditions, and discovering those specifics remains a challenge.

One application for metallocene catalysts is producing isotactic polypropylene. An extensive body of scientific literature examines catalyst structures, mechanism and polymers prepared by metallocene catalysts. See, e.g., Resconi et al., "Selectivity in Propene Polymerization with Metallocene Catalysts," *Chem. Rev.* 2000, 100, 1253–1345 and G. W. Coates, "Precise Control of Polyolefin Stereochemistry Using Single-Site Metal Catalysts," *Chem. Rev.* 2000, 100, 1223–1252 and the references sited in these review articles. See also, U.S. Pat. No. 5,026,798 that reports a mono-cyclopentadienyl metallocene for the production of isotactic polypropylene. Isotactic polypropylene has historically been produced with heterogeneous catalysts that may be described as a catalyst on a solid support (e.g., titanium tetrachloride and aluminum alkyls on magnesium dichloride). This process typically uses hydrogen to control the molecular weight and electron-donor compounds to control the isotacticity. See also EP 0622380, U.S. Pat. Nos. 4,297,465, 5,385,993 and 6,239,236.

Given the extensive research activities with respect to metallocene catalysts, there is continued interested in the next generation of non-cyclopentadienyl ligands for olefin polymerization catalysts providing attractive alternatives. See, e.g., "The Search for New-Generation Olefin Polymerization Catalysts: Life beyond Metallocenes", Gibson, et al., *Angew. Chem. Int. Ed.*, 1999, vol. 38, pp. 428–447; *Organometallics* 1999, 18, pp. 3649–3670. Recently, such systems have been discovered, see, e.g., U.S. Pat. Nos. 6,103,657 and 5,637,660. For isotactic polypropylene, bis-amide catalysts have been disclosed in U.S. Pat. No. 5,318,935 and amidinate catalysts have been disclosed in WO 99/05186. See also U.S. Pat. No. 6,214,939.

There remains a need for the discovery and optimization of non-cyclopentadienyl based catalysts for olefin polymerization, and in particular for certain polymers, such as isotactic polypropylene and ethylene-alpha-olefin copolymers. For a solution polymerization methodology, this need may be acute in view of the lack of versatile catalysts for the preparation of isotactic polypropylene at commercially acceptable temperatures. Indeed, new polymer properties are disclosed herein for isotactic polypropylene, ethylene-styrene copolymers and ethylene-isobutylene copolymers.

SUMMARY OF THE INVENTION

This invention discloses surprising enhanced catalytic performances for olefin polymerization when certain combinations of ligands and hafnium metal precursors are employed. This invention also discloses surprising enhanced catalytic performances for olefin polymerization when certain metal complexes are employed in a catalyst, including 2,1 metal complexes and 3,2 metal complexes. In addition, some of the ligands employed herein are themselves novel.

In some embodiments, this invention discloses both the preferred use of a hafnium metal center and certain pyridyl-amine ligands. Such combinations lead to new ligand-metal complexes, catalyst compositions and processes for the polymerization of olefins, diolefins, or other polymerizable monomers. In particular, copolymers of ethylene and another monomer may be prepared with controlled incorporation of the other monomer (e.g., 1-octene, isobutylene, or styrene) into the polymer backbone. In some embodiments, this control is adjusted so that the olefin incorporation is considered to be high with respect to polymers currently known or commercially available. Also in particular, propylene may be polymerized into very high molecular weight isotactic polypropylene. Thus, polymers having novel, improved or desired properties may be prepared using the catalysts and processes of this invention.

More specifically, in some embodiments, the use of a hafnium metal has been found to be preferred as compared to a zirconium metal for pyridyl-amine ligand catalysts. A broad range of ancillary ligand substituents may accommodate the enhanced catalytic performance. The catalysts in some embodiments are compositions comprising the ligand and metal precursor, and optionally may additionally include an activator, combination of activators or activator package.

The invention disclosed herein additionally includes catalysts comprising ancillary ligand-hafnium complexes, ancillary ligand-zirconium complexes and optionally activators, which catalyze polymerization and copolymerization reactions, particularly with monomers that are olefins, diolefins or other unsaturated compounds. Zirconium complexes, hafnium complexes, compositions or compounds using the disclosed ligands are within the scope of this invention. The metal-ligand complexes may be in a neutral or charged state. The ligand to metal ratio may also vary, the exact ratio being dependent on the nature of the ligand and metal-ligand complex. The metal-ligand complex or complexes may take different forms, for example, they may be monomeric, dimeric or higher orders thereof.

For example, suitable ligands useful in this invention may be characterized by the following general formula:

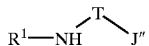

wherein $R^1$ is a ring having from 4–8 atoms in the ring generally selected from the group consisting of substituted cycloalkyl, substituted heterocycloalkyl, substituted aryl and substituted heteroaryl, such that $R^1$ may be characterized by the general formula:

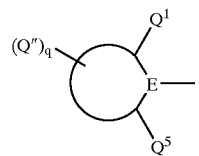

where $Q^1$ and $Q^5$ are substituents on the ring ortho to atom E, with E being selected from the group consisting of carbon and nitrogen and with at least one of $Q^1$ or $Q^5$ being bulky (defined as having at least 2 atoms). $Q''_q$ represents additional possible substituents on the ring, with q being 1, 2, 3, 4 or 5 and Q" being selected from the group consisting of hydrogen, alkyl, substituted alkyl, cycloalkyl, substituted cycloalkyl, heteroalkyl, substituted heteroalkyl, heterocycloalkyl, substituted hetercycloalkyl, aryl, substituted aryl, heteroaryl, substituted heteroaryl, alkoxyl, aryloxyl, silyl, boryl, phosphino, amino, thio, seleno, halide, nitro, and combinations thereof. T is a bridging group selected group consisting of —$CR^2R^3$— and —$SiR^2R^3$— with $R^2$ and $R^3$ being independently selected from the group consisting of hydrogen, alkyl, substituted alkyl, cycloalkyl, substituted cycloalkyl, heteroalkyl, substituted heteroalkyl, heterocycloalkyl, substituted hetercycloalkyl, aryl, substituted aryl, heteroaryl, substituted heteroaryl, alkoxyl, aryloxyl, silyl, boryl, phosphino, amino, thio, seleno, halide, nitro, and combinations thereof. J" is generally selected from the group consisting of heteroaryl and substituted heteroaryl, with particular embodiments for particular reactions being described herein.

Also for example, in some embodiments, the ligands of the invention may be combined with a metal precursor compound that may be characterized by the general formula $Hf(L)_n$ where L is independently selected from the group consisting of halide (F, Cl, Br, I), alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, hydroxy, boryl, silyl, amino, amine, hydrido, allyl, diene, seleno, phosphino, phosphine, carboxylates, thio, 1,3-dionates, oxalates, carbonates, nitrates, sulphates, ethers, thioethers and combinations thereof; and optionally two L groups may be linked together in a ring structure. n is 1, 2, 3, 4, 5, or 6.

In another aspect of the invention, a polymerization process is disclosed for monomers. The polymerization process involves subjecting one or more monomers to the catalyst compositions or complexes of this invention under polymerization conditions. The polymerization process can be continuous, batch or semi-batch and can be homogeneous, supported homogeneous or heterogeneous. Another aspect of this invention relates to arrays of ligands, metal precursors and/or metal-ligand complexes. These arrays are useful for the high speed or combinatorial materials science discovery or optimization of the catalyst compositions or complexes disclosed herein.

These catalysts comprising ancillary ligand-metal complexes or compositions comprising metal precursors and ligands and, optionally, activators are particularly effective at polymerizing α-olefins (such as propylene, 1-butene, 1-pentene, 1-hexene, is 1-heptene, 1-octene, and styrene), copolymerizing ethylene with α-olefins (such as propylene, 1-butene, 1-pentene, 1-hexene, 1-heptene, 1-octene, and styrene), and copolymerizing ethylene with 1,1-disubstituted olefins (such as isobutylene). These compositions might also polymerize monomers that have polar functionalities in homopolymerizations or copolymerizations. Also, diolefins in combination with ethylene and/or α-olefins or 1,1-disubstituted olefins may be copolymerized. The new catalyst compositions can be prepared by combining a hafnium precursor with a suitable ligand and, optionally, an activator or combination of activators. This invention discloses a novel class of catalysts and improved method for preparing isotactic polypropylene. The catalyst is useful for polymerizing a wide variety of polymerizable monomers.

In particular, a method of producing isotactic polypropylene is in a solution process is disclosed and is surprisingly tunable. In one aspect, the temperature of the solution polymerization process can be increased, which generally decreases the molecular weight, but surprisingly, while maintaining a relatively high isotacticity of the polypropylene and while maintaining a relatively high melting point for the polypropylene. In another aspect, the temperature of the solution process can be increased without the molecular weight of the polypropylene dropping so low to levels that are unacceptable for certain commercial applications.

In certain aspects, it has been discovered that certain ligands complex to the metal resulting in novel complexes. In one aspect, the 3,2 metal-ligand complexes of this invention may be generally characterized by the following formula:

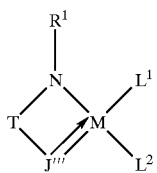

where M is zirconium or hafnium;

$R^1$ and T are defined above;

J''' being selected from the group of substituted heteroaryls with 2 atoms bonded to the metal M, at least one of those atoms being a heteroatom, and with one atom of J''' is bonded to M via a dative bond, the other through a covalent bond; and $L^1$ and $L^2$ are independently selected from the group consisting of halide, alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, hydroxy, boryl, silyl, amino, amine, hydrido, allyl, diene, seleno, phosphino, phosphine, carboxylates, thio, 1,3-dionates, oxalates, carbonates, nitrates, sulphates, ethers, thioethers and combinations thereof; and optionally the L groups may be linked together in a ring structure.

In another aspect, a solution process to prepare isotactic polypropylene is provided comprising adding a catalyst and propylene monomer to a reactor and subjecting the contents to polymerization conditions, where the temperature of the solution process is at least 110° C. and polypropylene is produced that has a weight average molecular weight of at least 100,000, without a drop off in tacticity value (i.e., crystallinity index).

Thus, it is a feature of this invention to use hafnium-ligand complexes as polymerization catalysts with enhanced performance.

It is an object of this invention to polymerize olefins and unsaturated monomers with hafnium-ligand complexes. It is also an object of this invention to polymerize olefins and unsaturated monomers with compositions including substituted pyridyl amine ligands and hafnium metal precursors.

It is still a further object of this invention to polymerize olefins and unsaturated monomers with the hafnium-ligand complexes that additionally comprise an activator or combination of activators.

It is also an object of this invention to use non-metallocene group 4 complexes as polymerization catalysts for the production of isotactic polypropylene.

It is a further object of this invention to polymerize olefins and unsaturated monomers with a catalyst comprised of metal complexes comprising 3,2 ligands.

Further objects and aspects of this invention will be evident to those of skill in the art upon review of this specification.

BRIEF DESCRIPTION OF THE DRAWINGS

FIG. 3 depicts Table 3, which shows the ligands and results from examples, below, using the Hf metal precursor.

Figure 4:
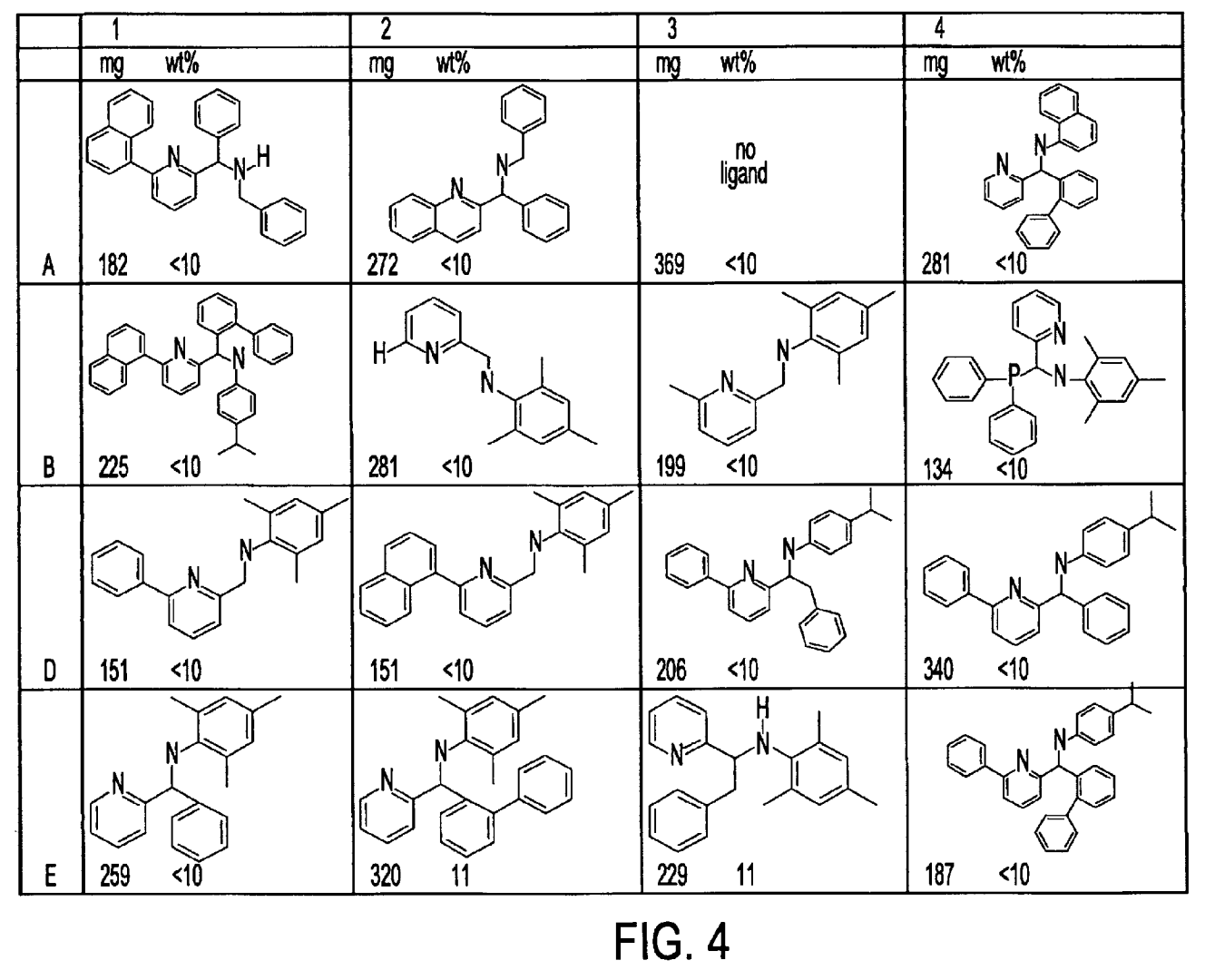

FIG. 4 depicts Table 4, which shows the ligands and results from comparative examples, below, using the Zr metal precursor.

DETAILED DESCRIPTION OF THE INVENTION

Figure 1:
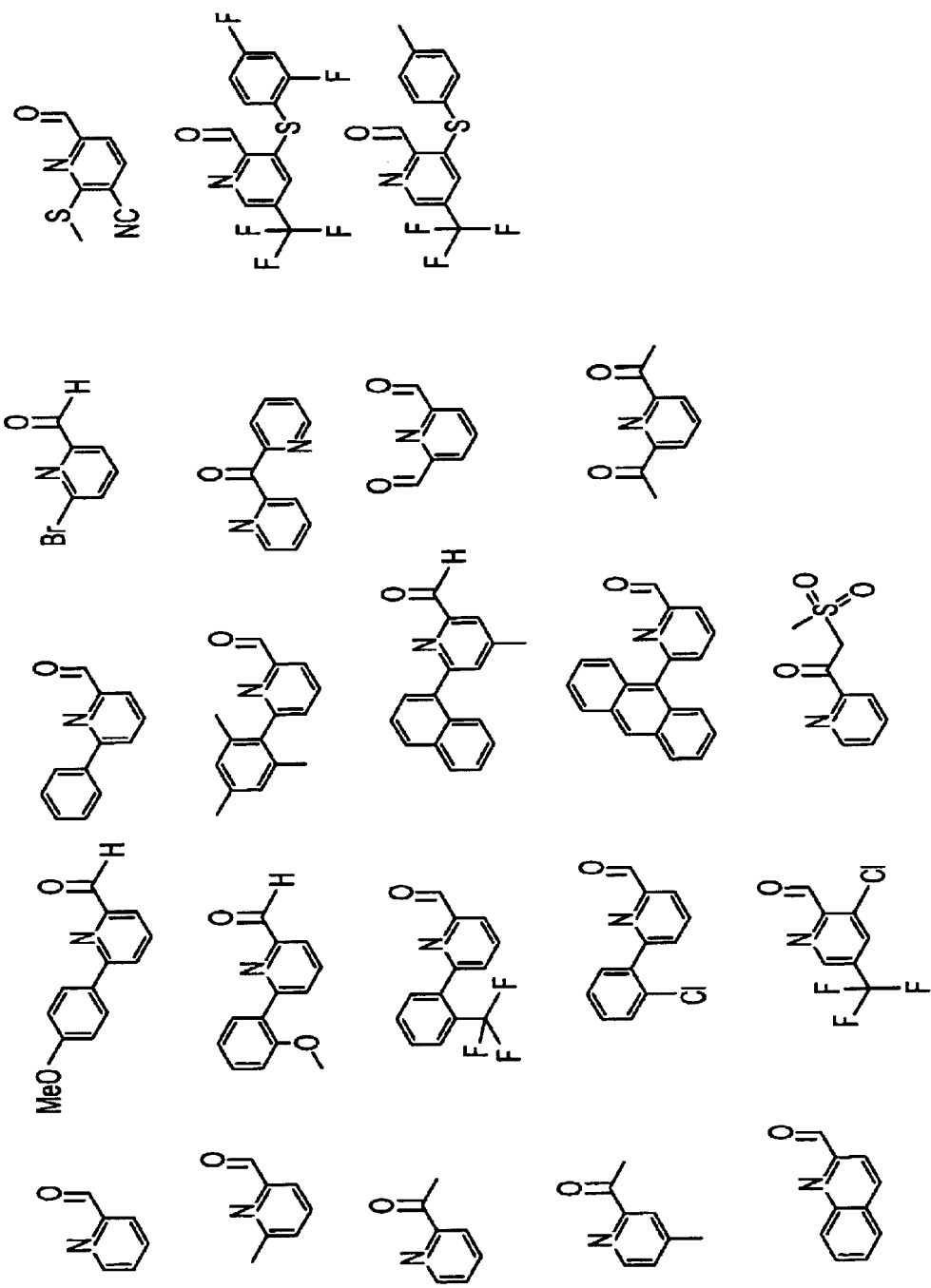
FIG. 1 depicts Table 1, which lists compounds that may be useful for synthesizing the ligands in this invention.
Figure 2A:
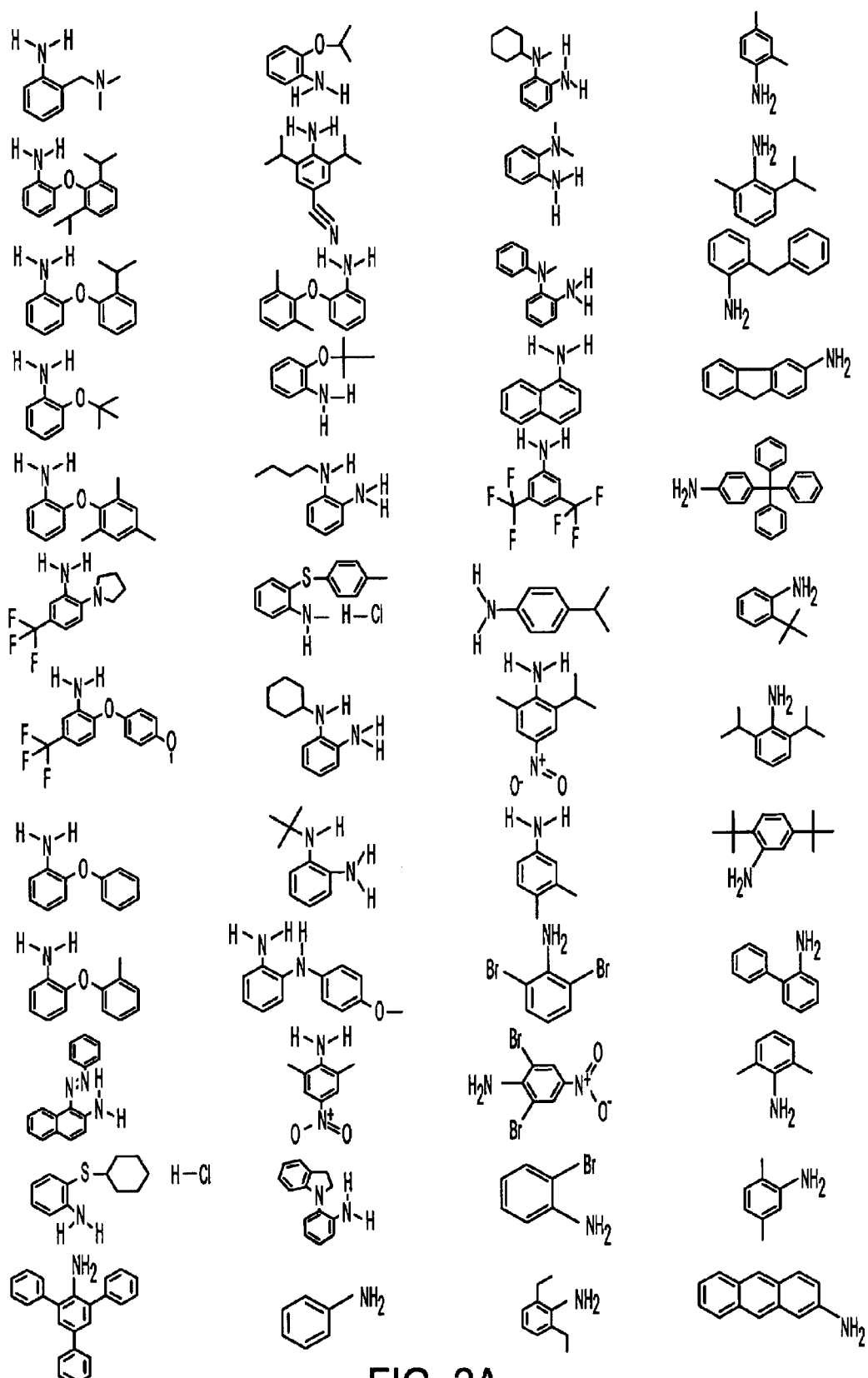
FIG. 2 depicts Table 2, which lists other compounds that may be useful for synthesizing the ligands in this invention.
Figure 2B:
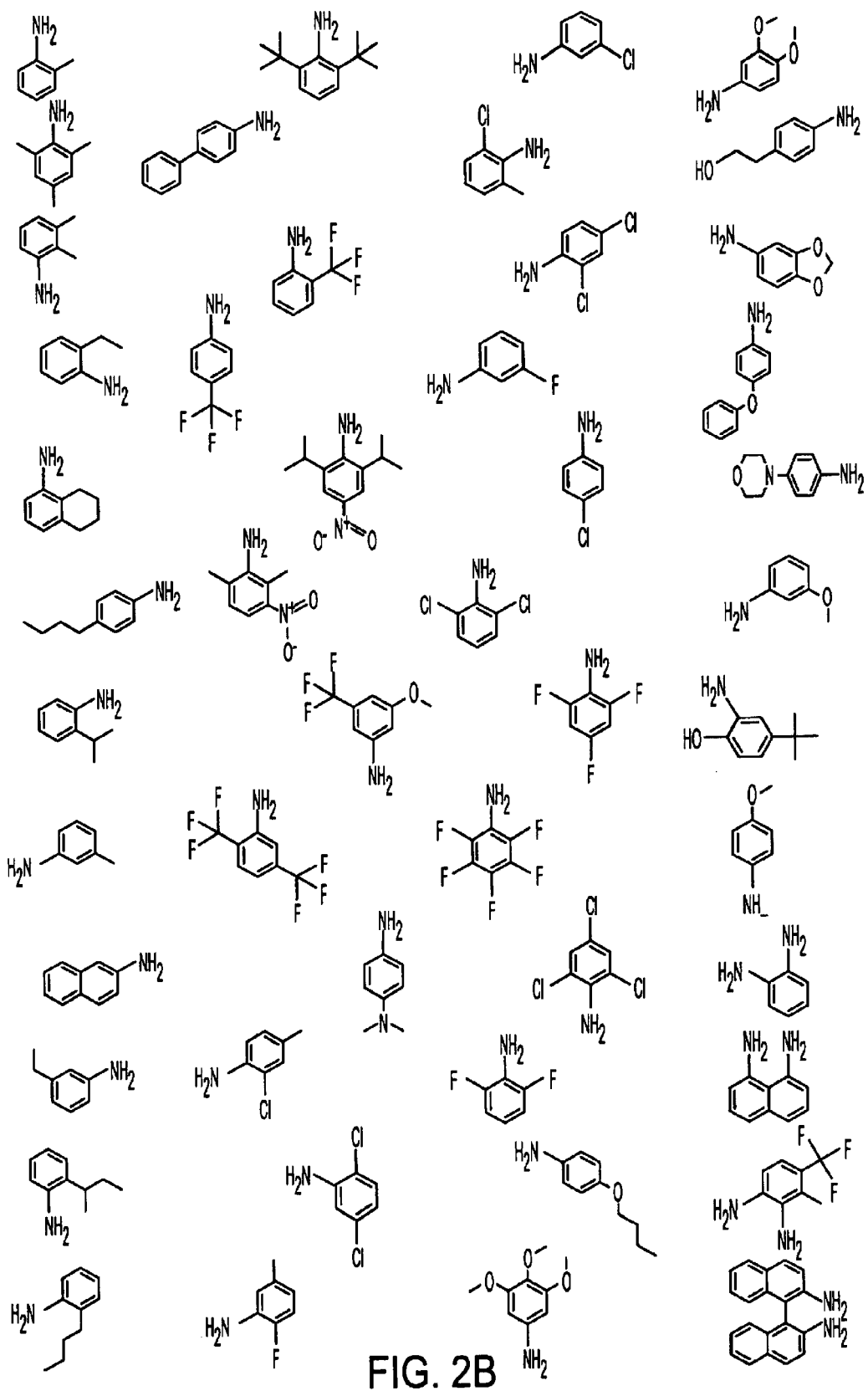
Figure 2C:
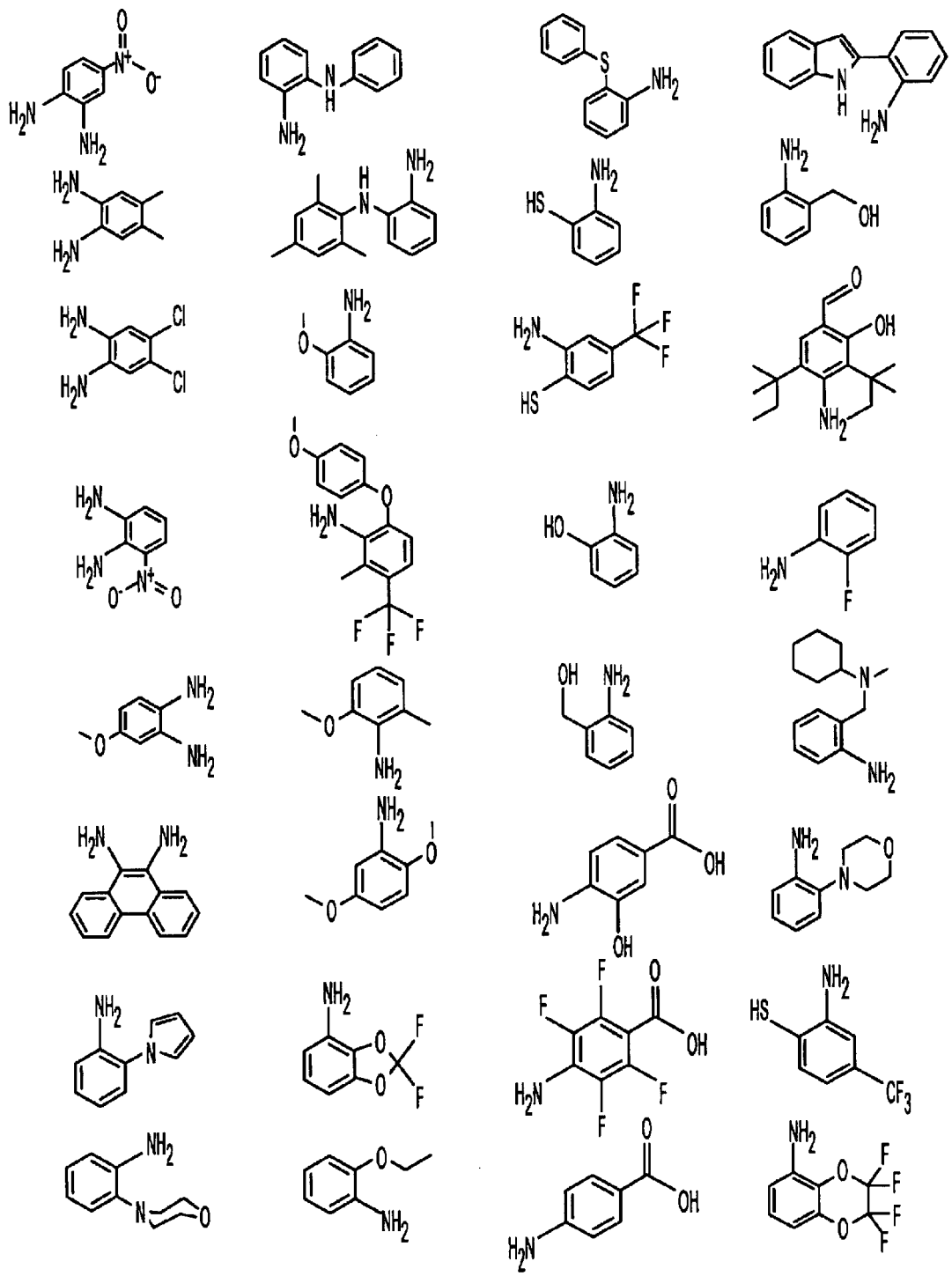
Figure 2D:
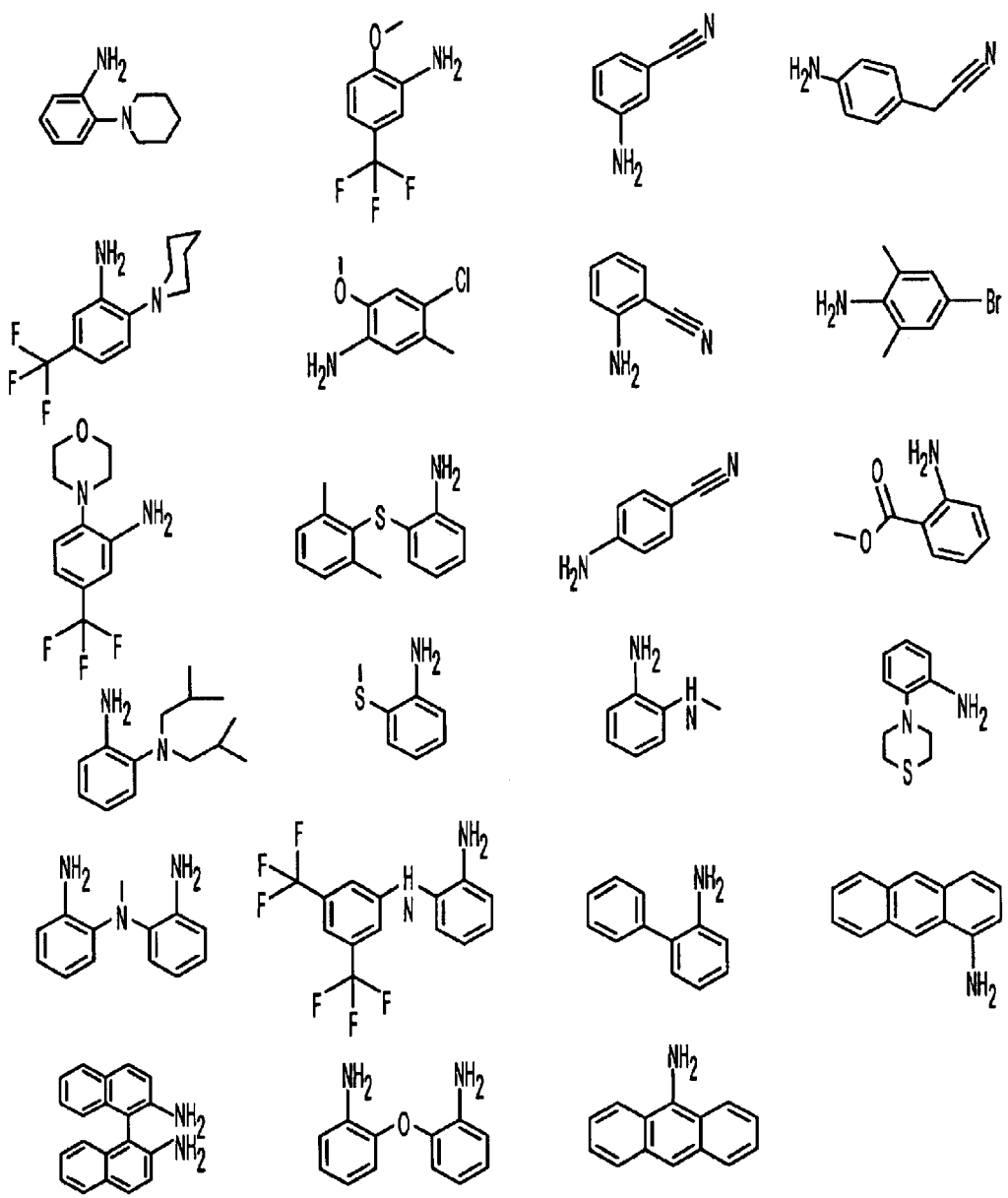

The inventions disclosed herein include metal complexes and compositions, which are useful as catalysts for polymerization reactions.

As used herein, the phrase "characterized by the formula" is not intended to be limiting and is used in the same way that "comprising" is commonly used. The term "independently selected" is used herein to indicate that the R groups, e.g., $R^1$, $R^2$, $R^3$, $R^4$, and $R^5$ can be identical or different (e.g. $R^1$, $R^2$, $R^3$, $R^4$, and $R^5$ may all be substituted alkyls or $R^1$ and $R^2$ may be a substituted alkyl and $R^3$ may be an aryl, etc.). Use of the singular includes use of the plural and vice versa (e.g., a hexane solvent, includes hexanes). A named R group will generally have the structure that is recognized in the art as corresponding to R groups having that name. The terms "compound" and "complex" are generally used interchangeably in this specification, but those of skill in the art may recognize certain compounds as complexes and vice versa. For the purposes of illustration, representative certain groups are defined herein. These definitions are intended to supplement and illustrate, not preclude, the definitions known to those of skill in the art.

"Hydrocarbyl" refers to univalent hydrocarbyl radicals containing 1 to about 30 carbon atoms, preferably 1 to about 24 carbon atoms, most preferably 1 to about 12 carbon atoms, including branched or unbranched, saturated or unsaturated species, such as alkyl groups, alkenyl groups, aryl groups, and the like. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom.

The term "alkyl" is used herein to refer to a branched or unbranched, saturated or unsaturated acyclic hydrocarbon radical. Suitable alkyl radicals include, for example, methyl, ethyl, n-propyl, i-propyl, 2-propenyl (or allyl), vinyl, n-butyl, t-butyl, i-butyl (or 2-methylpropyl), etc. In particular embodiments, alkyls have between 1 and 200 carbon atoms, between 1 and 50 carbon atoms or between 1 and 20 carbon atoms.

"Substituted alkyl" refers to an alkyl as just described in which one or more hydrogen atom bound to any carbon of the alkyl is replaced by another group such as a halogen, aryl, substituted aryl, cycloalkyl, substituted cycloalkyl, heterocycloalkyl, substituted heterocycloalkyl, halogen, alkylhalos (e.g., $CF_3$), hydroxy, amino, phosphido, alkoxy, amino, thio, nitro, and combinations thereof. Suitable substituted alkyls include, for example, benzyl, trifluoromethyl and the like.

The term "heteroalkyl" refers to an alkyl as described above in which one or more hydrogen atoms to any carbon of the alkyl is replaced by a heteroatom selected from the group consisting of N, O, P, B, S, Si, Sb, Al, Sn, As, Se and Ge. This same list of heteroatoms is useful throughout this specification. The bond between the carbon atom and the heteroatom may be saturated or unsaturated. Thus, an alkyl substituted with a heterocycloalkyl, substituted heterocycloalkyl, heteroaryl, substituted heteroaryl, alkoxy, aryloxy, boryl, phosphino, amino, silyl, thio, or seleno is within the scope of the term heteroalkyl. Suitable heteroalkyls include cyano, benzoyl, 2-pyridyl, 2-furyl and the like.

The term "cycloalkyl" is used herein to refer to a saturated or unsaturated cyclic non-aromatic hydrocarbon radical having a single ring or multiple condensed rings. Suitable cycloalkyl radicals include, for example, cyclopentyl, cyclohexyl, cyclooctenyl, bicyclooctyl, etc. In particular embodiments, cycloalkyls have between 3 and 200 carbon atoms, between 3 and 50 carbon atoms or between 3 and 20 carbon atoms.

"Substituted cycloalkyl" refers to cycloalkyl as just described including in which one or more hydrogen atom to any carbon of the cycloalkyl is replaced by another group such as a halogen, alkyl, substituted alkyl, aryl, substituted aryl, cycloalkyl, substituted cycloalkyl, heterocycloalkyl, substituted heterocycloalkyl, heteroaryl, substituted heteroaryl, alkoxy, aryloxy, boryl, phosphino, amino, silyl, thio, seleno and combinations thereof. Suitable substituted cycloalkyl radicals include, for example, 4-dimethylaminocyclohexyl, 4,5-dibromocyclohept-4-enyl, and the like.

The term "heterocycloalkyl" is used herein to refer to a cycloalkyl radical as described, but in which one or more or all carbon atoms of the saturated or unsaturated cyclic radical are replaced by a heteroatom such as nitrogen, phosphorous, oxygen, sulfur, silicon, germanium, selenium, or boron. Suitable heterocycloalkyls include, for example, piperazinyl, morpholinyl, tetrahydropyranyl, tetrahydrofuranyl, piperidinyl, pyrrolidinyl, oxazolinyl and the like.

"Substituted heterocycloalkyl" refers to heterocycloalkyl as just described including in which one or more hydrogen atom to any atom of the heterocycloalkyl is replaced by another group such as a halogen, alkyl, substituted alkyl, aryl, substituted aryl, heteroaryl, substituted heteroaryl, alkoxy, aryloxy, boryl, phosphino, amino, silyl, thio, seleno and combinations thereof. Suitable substituted heterocycloalkyl radicals include, for example, N-methylpiperazinyl, 3-dimethylaminomorpholinyl and the like.

The term "aryl" is used herein to refer to an aromatic substituent, which may be a single aromatic ring or multiple aromatic rings that are fused together, linked covalently, or linked to a common group such as a methylene or ethylene moiety. The aromatic ring(s) may include phenyl, naphthyl, anthracenyl, and biphenyl, among others. In particular embodiments, aryls have between 1 and 200 carbon atoms, between 1 and 50 carbon atoms or between 1 and 20 carbon atoms. In some embodiments herein, multi-ring moieties are substituents and in such an embodiment the multi-ring moiety can be attached at an appropriate atom. For example, "naphthal" can be 1-naphthyl or 2-naphthyl; "anthracenyl" can be 1-anthracenyl, 2-anthracenyl or 9-anthracenyl; and "phenanthrenyl" can be 1-phenanthrenyl, 2-phenanthrenyl, 3-phenanthrenyl, 4-phenanthrenyl or 9-phenanthrenyl.

"Substituted aryl" refers to aryl as just described in which one or more hydrogen atom bound to any carbon is replaced by one or more functional groups such as alkyl, substituted alkyl, cycloalkyl, substituted cycloalkyl, heterocycloalkyl, substituted heterocycloalkyl, halogen, alkylhalos (e.g., $CF_3$), hydroxy, amino, phosphido, alkoxy, amino, thio, nitro, and both saturated and unsaturated cyclic hydrocarbons which are fused to the aromatic ring(s), linked covalently or linked to a common group such as a methylene or ethylene moiety. The common linking group may also be a carbonyl as in benzophenone or oxygen as in diphenylether or nitrogen in diphenylamine.

The term "heteroaryl" as used herein refers to aromatic or unsaturated rings in which one or more carbon atoms of the aromatic ring(s) are replaced by a heteroatom(s) such as nitrogen, oxygen, boron, selenium, phosphorus, silicon or sulfur. Heteroaryl refers to structures that may be a single aromatic ring, multiple aromatic ring(s), or one or more aromatic rings coupled to one or more non-aromatic ring(s). In structures having multiple rings, the rings can be fused together, linked covalently, or linked to a common group such as a methylene or ethylene moiety. The common linking group may also be a carbonyl as in phenyl pyridyl ketone. As used herein, rings such as thiophene, pyridine, isoxazole, pyrazole, pyrrole, furan, etc. or benzo-fused analogues of these rings are defined by the term "heteroaryl."

"Substituted heteroaryl" refers to heteroaryl as just described including in which one or more hydrogen atoms bound to any atom of the heteroaryl moiety is replaced by another group such as a halogen, alkyl, substituted alkyl, aryl, substituted aryl, heteroaryl, substituted heteroaryl, alkoxy, aryloxy, boryl, phosphino, amino, silyl, thio, seleno and combinations thereof. Suitable substituted heteroaryl radicals include, for example, 4-N,N-dimethylaminopyridine.

The term "alkoxy" is used herein to refer to the —$OZ^1$ radical, where $Z^1$ is selected from the group consisting of alkyl, substituted alkyl, cycloalkyl, substituted cycloalkyl, heterocylcoalkyl, substituted heterocycloalkyl, silyl groups and combinations thereof as described herein. Suitable alkoxy radicals include, for example, methoxy, ethoxy, benzyloxy, t-butoxy, etc. A related term is "aryloxy" where $Z^1$ is selected from the group consisting of aryl, substituted aryl, heteroaryl, substituted heteroaryl, and combinations thereof. Examples of suitable aryloxy radicals include phenoxy, substituted phenoxy, 2-pyridinoxy, 8-quinalinoxy and the like.

As used herein the term "silyl" refers to the —$SiZ^1Z^2Z^3$ radical, where each of $Z^1$, $Z^2$, and $Z^3$ is independently selected from the group consisting of hydrogen, alkyl, substituted alkyl, cycloalkyl, heterocycloalkyl, heterocyclic, aryl, substituted aryl, heteroaryl, substituted heteroaryl, alkoxy, aryloxy, amino, silyl and combinations thereof.

As used herein the term "boryl" refers to the —$BZ^1Z^2$ group, where each of $Z^1$ and $Z^2$ is independently selected from the group consisting of hydrogen, alkyl, substituted alkyl, cycloalkyl, heterocycloalkyl, heterocyclic, aryl, substituted aryl, heteroaryl, substituted heteroaryl, alkoxy, aryloxy, amino, silyl and combinations thereof.

As used herein, the term "phosphino" refers to the group —$PZ^1Z^2$, where each of $Z^1$ and $Z^2$ is independently selected from the group consisting of hydrogen, substituted or unsubstituted alkyl, cycloalkyl, heterocycloalkyl, heterocyclic, aryl, substituted aryl, heteroaryl, silyl, alkoxy, aryloxy, amino and combinations thereof.

As used herein, the term "phosphine" refers to the group: $PZ^1Z^2Z^3$, where each of $Z^1$, $Z^3$ and $Z^2$ is independently selected from the group consisting of hydrogen, substituted or unsubstituted alkyl, cycloalkyl, heterocycloalkyl, heterocyclic, aryl, substituted aryl, heteroaryl, silyl, alkoxy, aryloxy, amino and combinations thereof.

The term "amino" is used herein to refer to the group —$NZ^1Z^2$, where each of $Z^1$ and $Z^2$ is independently selected from the group consisting of hydrogen, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

The term "amine" is used herein to refer to the group: $NZ^1Z^2Z^3$, where each of $Z^1$, $Z^2$ and $Z^2$ is independently selected from the group consisting of hydrogen, alkyl, substituted alkyl, cycloalkyl, substituted cycloalkyl, heterocycloalkyl, substituted heterocycloalkyl, aryl (including pyridines), substituted aryl, heteroaryl, substituted heteroaryl, alkoxy, aryloxy, silyl and combinations thereof.

The term "thio" is used herein to refer to the group —$SZ^1$, where $Z^1$ is selected from the group consisting of hydrogen, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

The term "seleno" is used herein to refer to the group —$SeZ^1$, where $Z^1$ is selected from the group consisting of hydrogen, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

The term "saturated" refers to lack of double and triple bonds between atoms of a radical group such as ethyl, cyclohexyl, pyrrolidinyl, and the like.

The term "unsaturated" refers to the presence one or more double and triple bonds between atoms of a radical group such as vinyl, acetylide, oxazolinyl, cyclohexenyl, acetyl and the like.

Other abbreviations used herein include: "$Pr^i$" to refer to isopropyl; "$Bu^t$" to refer to tertbutyl; "Me" to refer to methyl; and "Et" to refer to ethyl.

Ligands

Suitable ligands useful in this invention can be characterized broadly as monoanionic ligands having an amine and a heteroaryl or substituted heteroaryl group. The ligand substituents for particular monomers are detailed near the end of this section. The ligands of the invention may be characterized by the following general formula:

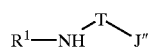
(I)

wherein $R^1$ is generally selected from the group consisting of alkyl, substituted alkyl, cycloalkyl, substituted cycloalkyl, heteroalkyl, substituted heteroalkyl, heterocycloalkyl, substituted hetercycloalkyl, aryl, substituted aryl, heteroaryl, substituted heteroaryl and combinations thereof. In many embodiments, $R^1$ is a ring having from 4–8 atoms in the ring generally selected from the group consisting of substituted cycloalkyl, substituted heterocycloalkyl, substituted aryl and substituted heteroaryl, with $R^1$ being characterized by the general formula:

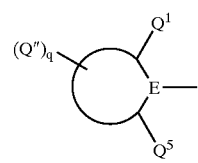
(A)

where $Q^1$ and $Q^5$ are substituents on the ring ortho to atom E, with E being selected from the group consisting of carbon and nitrogen and with at least one of $Q^1$ or $Q^5$ being bulky (defined as having at least 2 non-hydrogen atoms). $Q^1$ and $Q^5$ are independently selected from the group consisting of alkyl, substituted alkyl, cycloalkyl, substituted cycloalkyl, aryl, substituted aryl and silyl, but provided that $Q^1$ and $Q^5$ are not both methyl. $Q''_q$ represents additional possible substituents on the ring, with q being 1, 2, 3, 4 or 5 and Q" being selected from the group consisting of hydrogen, alkyl, substituted alkyl, cycloalkyl, substituted cycloalkyl, heteroalkyl, substituted heteroalkyl, heterocycloalkyl, substituted hetercycloalkyl, aryl, substituted aryl, heteroaryl, substituted heteroaryl, alkoxyl, aryloxyl, silyl, boryl, phosphino, amino, thio, seleno, halide, nitro, and combinations thereof T is a bridging group selected group consisting of —$CR^2R^3$— and —$SiR^2R^3$— with $R^2$ and $R^3$ being independently selected from the group consisting of hydrogen, alkyl, substituted alkyl, cycloalkyl, substituted cycloalkyl, heteroalkyl, substituted heteroalkyl, heterocycloalkyl, substituted hetercycloalkyl, aryl, substituted aryl, heteroaryl, substituted heteroaryl, alkoxyl, aryloxyl, silyl, boryl, phosphino, amino, thio, seleno, halide, nitro, and combinations thereof. J" is generally selected from the group consisting of heteroaryl and substituted heteroaryl, with particular embodiments for particular reactions being described herein.

In a more specific embodiment, suitable ligands useful in this invention may be characterized by the following general formula:

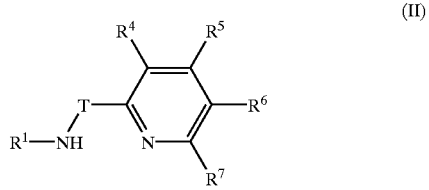
(II)

wherein $R^1$ and T are as defined above and each of $R^4$, $R^5$, $R^6$ and $R^7$ is independently selected from the group consisting of hydrogen, alkyl, substituted alkyl, cycloalkyl, substituted cycloalkyl, heteroalkyl, substituted heteroalkyl, heterocycloalkyl, substituted hetercycloalkyl, aryl, substituted aryl, heteroaryl, substituted heteroaryl, alkoxyl, aryloxyl, silyl, boryl, phosphino, amino, thio, seleno, halide, nitro, and combinations thereof. Optionally, any combination of $R^1$, $R^2$, $R^3$ and $R^4$ may be joined together in a ring structure.

In certain more specific embodiments, the ligands in this invention may be characterized by the following general formula:

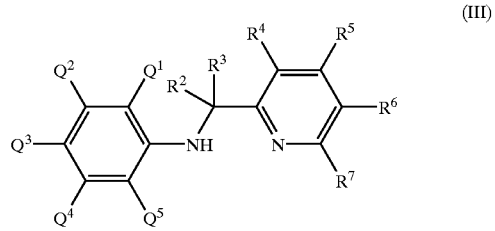
(III)

wherein $Q^1$, $Q^5$, $R^2$, $R^3$, $R^4$, $R^5$, $R^6$ and $R^7$ are as defined above. $Q^2$, $Q^3$ and $Q^4$ are independently selected from the group consisting of hydrogen, alkyl, substituted alkyl, cycloalkyl, substituted cycloalkyl, heteroalkyl, substituted heteroalkyl, heterocycloalkyl, substituted hetercycloalkyl, aryl, substituted aryl, heteroaryl, substituted heteroaryl, alkoxyl, aryloxyl, silyl, boryl, phosphino, amino, thio, seleno, nitro, and combinations thereof.

In other more specific embodiments, the ligands of this invention and suitable herein may be characterized by the following general formula:

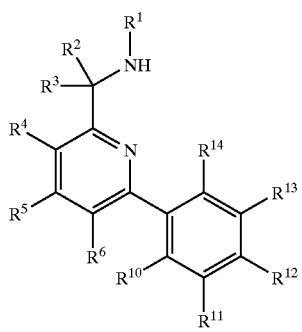

(IV)

wherein $R^1$, $R^2$, $R^3$, $R^4$, $R^5$, and $R^6$ are as defined above. In this embodiment the $R^7$ substituent has been replaced with an aryl or substituted aryl group, with $R^{10}$, $R^{11}$, $R^{12}$ and $R^{13}$ being independently selected from the group consisting of hydrogen, halide, alkyl, substituted alkyl, cycloalkyl, substituted cycloalkyl, heteroalkyl, substituted heteroalkyl, heterocycloalkyl, substituted hetercycloalkyl, aryl, substituted aryl, heteroaryl, substituted heteroaryl, alkoxy, aryloxy, silyl, boryl, phosphino, amino, thio, seleno, nitro, and combinations thereof; optionally, two or more $R^{10}$, $R^{11}$, $R^{12}$ and $R^{13}$ groups may be joined to form a fused ring system having from 3–50 non-hydrogen atoms. $R^{14}$ is selected from the group consisting of hydrogen, alkyl, substituted alkyl, cycloalkyl, substituted cycloalkyl, heteroalkyl, substituted heteroalkyl, heterocycloalkyl, substituted hetercycloalkyl, aryl, substituted aryl, heteroaryl, substituted heteroaryl, alkoxy, aryloxy, silyl, boryl, phosphino, amino, thio, seleno, halide, nitro, and combinations thereof.

In still more specific embodiments, the ligands in this invention may be characterized by the general formula:

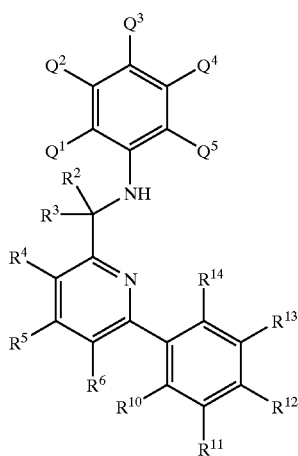

(V)

wherein $R^2$–$R^6$, $R^{10}$–$R^{14}$ and $Q^1$–$Q^5$ are all as define above.

In certain embodiments, $R^2$ is preferably hydrogen. Also preferably, each of $R^4$ and $R^5$ is hydrogen and $R^6$ is either hydrogen or is joined to $R^7$ to form a fused ring system. Also preferred is where $R^3$ is selected from the group consisting of benzyl, phenyl, naphthyl, 2-biphenyl, t-butyl, 2-dimethylaminophenyl (2-(NMe$_2$)—C$_6$H$_4$—),2-methoxyphenyl (2-MeO—C$_6$H$_4$—), anthracenyl, mesityl, 2-pyridyl, 3,5-dimethylphenyl, o-tolyl and phenanthrenyl. Also preferred is where $R^1$ is selected from the group consisting of mesityl, 4-isopropylphenyl (4-Pr$^i$—C$_6$H$_4$—), napthyl, 3,5-(CF$_3$)$_2$—C$_6$H$_3$—, 2-Me-napthyl, 2,6-(Pr$^i$)$_2$—C$_6$H$_3$—, 2-biphenyl, 2-Me-4-MeO—C$_6$H$_3$—, 2-Bu$^t$—C$_6$H$_4$—, 2,5-(Bu$^t$)$_2$—C$_6$H$_3$—, 2-Pr$^i$-6-Me—C$_6$H$_3$—, 2-Bu$^t$-6-Me—C$_6$H$_3$—, 2,6-Et$_2$—C$_6$H$_3$— or 2-sec-butyl-6Et—C$_6$H$_3$—. Also preferred is where $R^7$ is selected from the group consisting of hydrogen, phenyl, napthyl, methyl, anthracenyl, phenanthrenyl, mesityl, 3,5-(CF$_3$)$_2$—C$_6$H$_3$—, 2-CF$_3$—C$_6$H$_4$—, 4-CF$_3$—C$_6$H$_4$—, 3,5-F$_2$—C$_6$H$_3$—, 4-F—C$_6$H$_4$—, 2,4—F$_2$—C$_6$H$_3$—, 4-(NMe$_2$)—C$_6$H$_4$—, 3-MeO—C$_6$H$_4$—, 4-MeO—C$_6$H$_4$—, 3,5-Me$_2$—C$_6$H$_3$—, o-tolyl, 2,6-F$_2$—C$_6$H$_3$— or where $R^7$ is joined together with $R^6$ to form a fused ring system, e.g., quinoline. In some preferred embodiment, $R^4$, $R^5$ and $R^6$ are each independently selected from the group consisting of alkyl, aryl, halide, alkoxy, aryloxy, amino, and thio.

In some embodiments, $Q^1$ and $Q^5$ are, independently, selected from the group consisting of —CH$_2$R$^{15}$, —CHR$^{16}$R$^{17}$ and methyl, provided that not both $Q^1$ and $Q^5$ are methyl. In these embodiments, $R^{15}$ is selected from the group consisting of alkyl, substituted alkyl, aryl and substituted aryl. $R^{16}$ and $R^{17}$ are independently selected from the group consisting of alkyl, substituted alkyl, aryl and substituted aryl; and optionally $R^{16}$ and $R^{17}$ are joined together in a ring structure having from 3–50 non-hydrogen atoms.

Also optionally, two or more $R^4$, $R^5$, $R^6$, $R^7$ groups may be joined to form a fused ring system having from 3–50 non-hydrogen atoms in addition to the pyridine ring, e.g. generating a quinoline group. In these embodiments, $R^3$ is selected from the group consisting of aryl, substituted aryl, heteroaryl, substituted heteroaryl, primary and secondary alkyl groups, and —PY$_2$ where Y is selected from the group consisting of aryl, substituted aryl, heteroaryl, and substituted heteroaryl.

Optionally within above formulas IV and V, $R^6$ and $R^{10}$ may be joined to form a ring system having from 5–50 non-hydrogen atoms. For example, if $R^6$ and $R^{10}$ together form a methylene, the ring will have 5 atoms in the backbone of the ring, which may or may not be substituted with other atoms. Also for example, if $R^6$ and $R^{10}$ together form an ethylene, the ring will have 6 atoms in the backbone of the ring, which may or may not be substituted with other atoms. Substituents from the ring can be selected from the group consisting of halide, alkyl, substituted alkyl, cycloalkyl, substituted cycloalkyl, heteroalkyl, substituted heteroalkyl, heterocycloalkyl, substituted hetercycloalkyl, aryl, substituted aryl, heteroaryl, substituted heteroaryl, alkoxy, aryloxy, silyl, boryl, phosphino, amino, thio, seleno, nitro, and combinations thereof.

Specific examples of ligands within the scope of these formulas include:

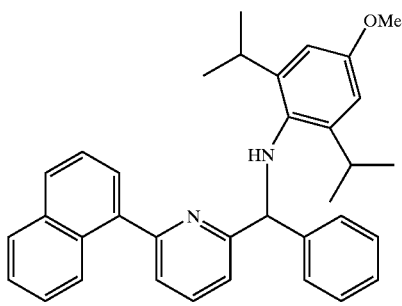

-continued
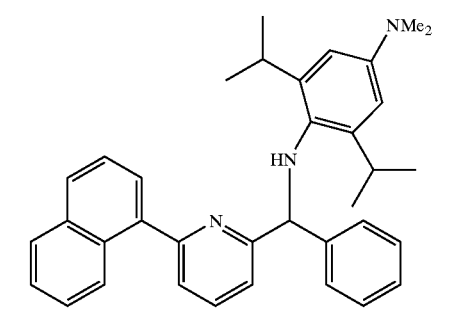
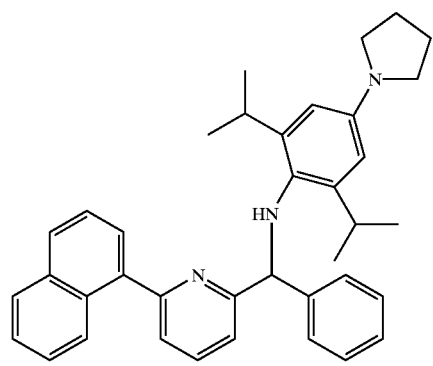
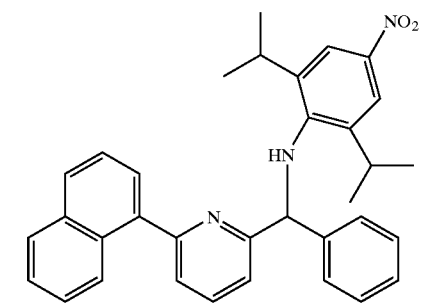
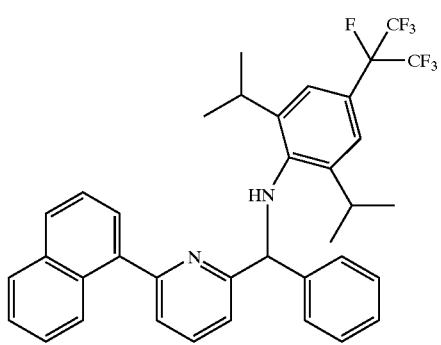
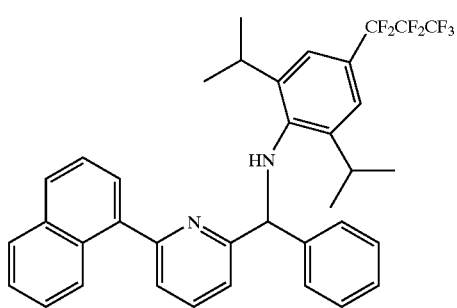
-continued
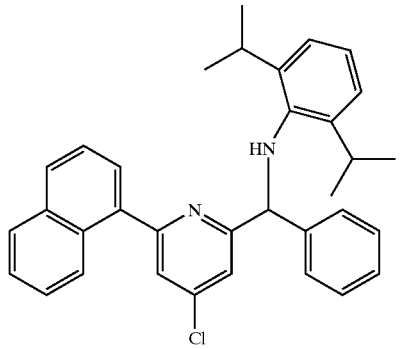
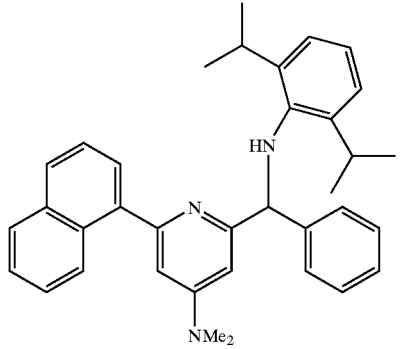
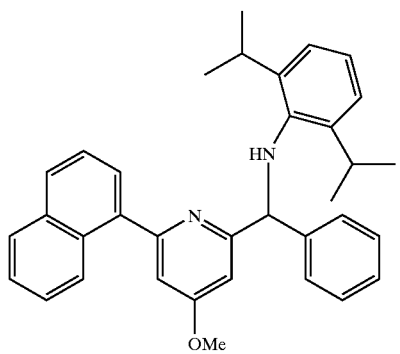
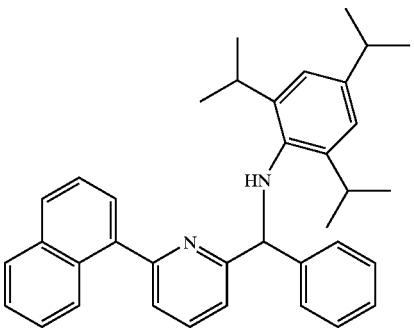
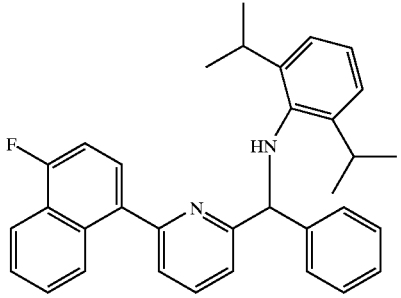

-continued

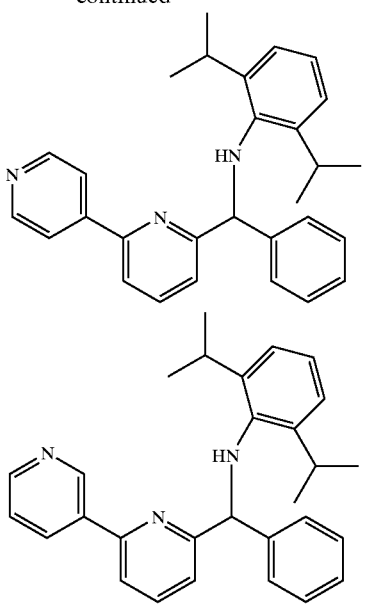

In certain embodiments, the ligands are novel compounds and those of skill in the art will be able to identify such compounds from the above. One example of the novel ligand compounds, includes those compounds generally characterized by formula (III), above where $R^2$ is selected from the group consisting of hydrogen, alkyl, substituted alkyl, cycloalkyl, substituted cycloalkyl, aryl, and substituted aryl; and $R^3$ is a phosphino characterized by the formula $-PZ^1Z^2$, where each of $Z^1$ and $Z^2$ is independently selected from the group consisting of hydrogen, substituted or unsubstituted alkyl, cycloalkyl, heterocycloalkyl, heterocyclic, aryl, substituted aryl, heteroaryl, silyl, alkoxy, aryloxy, amino and combinations thereof. Particularly preferred embodiments of these compounds include those where $Z^1$ and $Z^2$ are each independently selected from the group consisting of alkyl, substituted alkyl, cycloalkyl, heterocycloalkyl, aryl, and substituted aryl; and more specifically phenyl; where $Q^1$, $Q^3$, and $Q^5$ are each selected from the group consisting of alkyl and substituted alkyl and each of $Q^2$ and $Q^4$ is hydrogen; and where $R^4$, $R^5$, $R^6$ and $R^7$ are each hydrogen.

Certain embodiments of these ligands are preferred for the polymerization of certain monomers. In any of the above formulas I, II, III, IV or V, for the production of isotactic polypropylene it is an aspect of this invention that $R^2$ cannot be the same group as $R^3$, leading to a chiral center on the carbon atom from which $R^2$ and $R^3$ stem. Thus, generally, $R^3$ may be selected from the group consisting of hydrogen, halide, alkyl, substituted alkyl, cycloalkyl, substituted cycloalkyl, heteroalkyl, substituted heteroalkyl, heterocycloalkyl, substituted hetercycloalkyl, aryl, substituted aryl, heteroaryl, substituted heteroaryl, alkoxy, aryloxy, silyl, boryl, phosphino, amino, thio, seleno, nitro, and combinations thereof, but it has also been learned that for isotactic polypropylene production $R^3$ is aryl, substituted aryl, heteroaryl or substituted heteroaryl. In more specific embodiments for isotactic polypropylene production $R^3$ is selected from the group consisting of benzyl, phenyl, naphthyl, 2-biphenyl, 2-dimethylaminophenyl, 2-methoxyphenyl, anthracenyl, mesityl, 2-pyridyl, 3,5-dimethylphenyl, o-tolyl, or phenanthrenyl. Also here, $R^1$ is selected from the group consisting of 2,6-$(Pr^i)_2$—$C_6H_3$—, 2-$Pr^i$-6-Me—$C_6H_3$—, 2,6-$Et_2$—$C_6H_3$— or 2-sec-butyl-6-Et—$C_6H_3$—.

Also for isotactic polypropylene production it is preferred that within formula A, above, it is currently preferred that $Q^1$ and $Q^5$ are alkyl, substituted alkyl, heteroalkyl, substituted heteroalkyl, silyl, cycloalkyl, or substituted cycloalkyl, provided that $Q^1$ and $Q^5$ are not both methyl. Here also, $Q^1$ and $Q^5$ can be, independently, selected from the group consisting of —$CH_2R^{15}$, —$CHR^{16}R^{17}$ and methyl, provided that not both $Q^1$ and $Q^5$ are methyl. In a more specific embodiment for isotactic polypropylene production, it is currently preferred that $Q^1$ and $Q^5$ are both isopropyl; or both ethyl; or both sec-butyl; or $Q^1$ is methyl and $Q^5$ is isopropyl; or $Q^1$ is ethyl and $Q^5$ is sec-butyl. Even more specifically, with these $Q^1$ and $Q^5$ preferences, $R^1$ is either

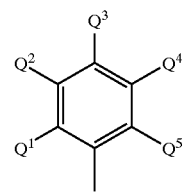

or

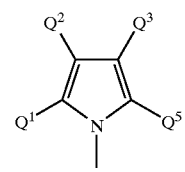

with the above definitions of the variables applying.

For isotactic polypropylene production it is preferred $R^7$ is aryl, substituted aryl, heteroaryl or substituted heteroaryl, and more specifically $R^7$ is phenyl, napthyl, mesityl, anthracenyl or phenanthrenyl. Thus, most preferably, formulas IV and V above apply to isotactic polypropylene production, with it currently being preferred that $R^{10}$, $R^{11}$, $R^{12}$, $R^{13}$ each hydrogen; or one or more of $R^{10}$, $R^{11}$, $R^{12}$, $R^{13}$ are methyl, fluoro, trifluoromethyl, methoxy, or dimethylamino; or where $R^{10}$ and $R^{11}$ are joined to form a benzene ring and $R^{12}$ and $R^{13}$ are each hydrogen (thus forming a napthyl group with the existing phenyl ring).

Specific ligands that are preferred for the production of crystalline polypropylene are:

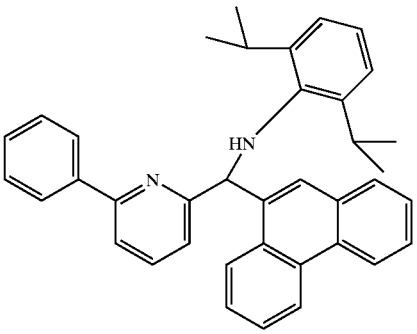

-continued
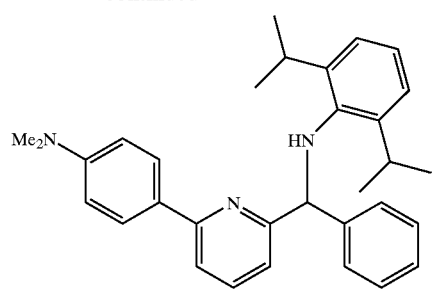
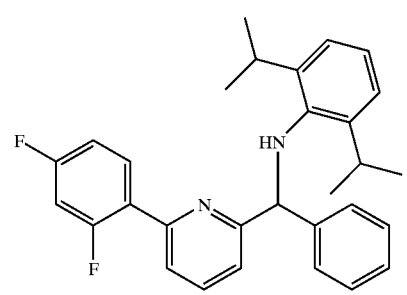
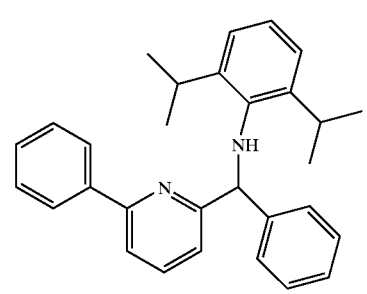
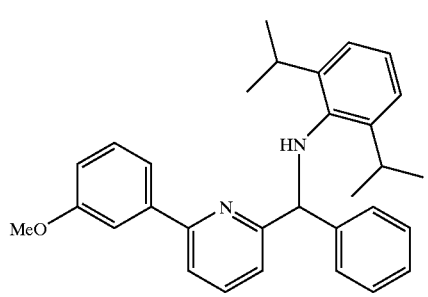
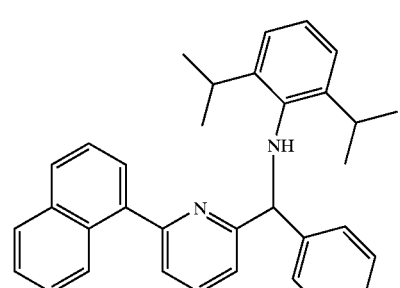
-continued
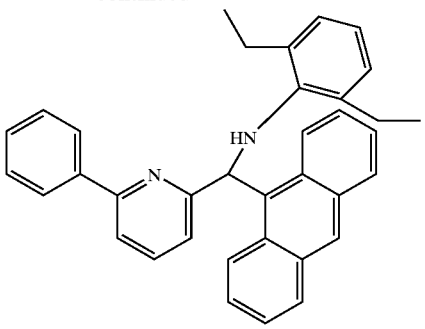
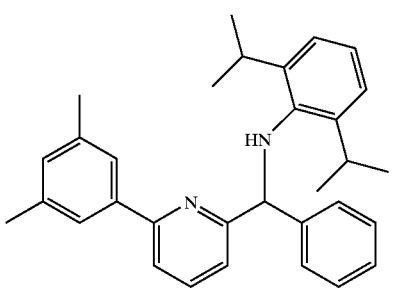
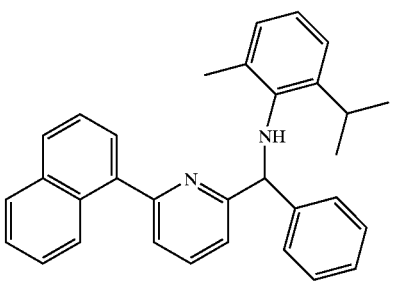
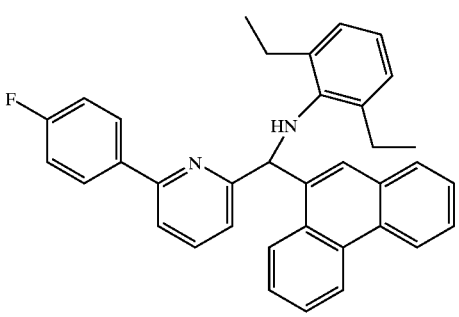
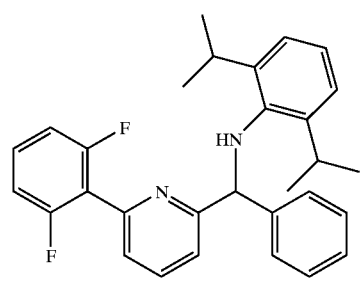

-continued
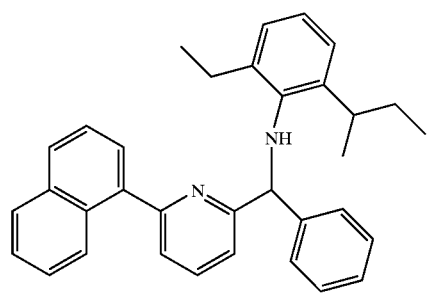
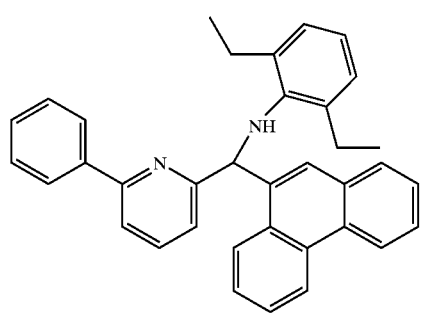
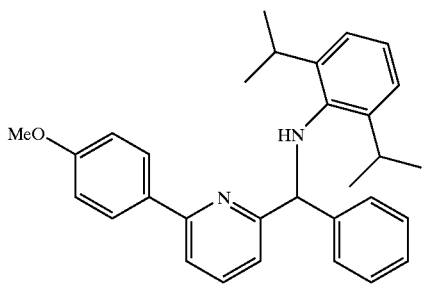
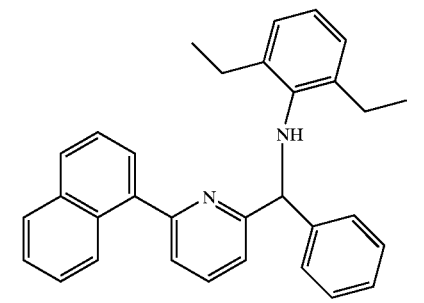
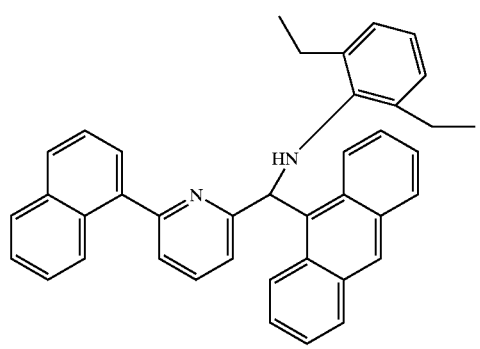
-continued
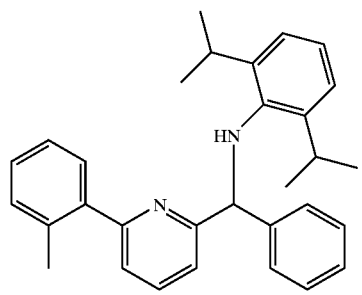
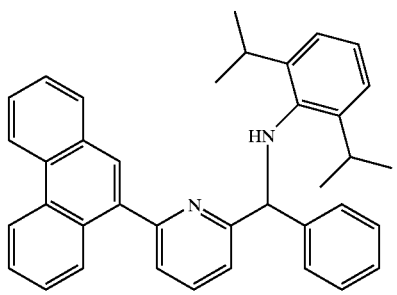
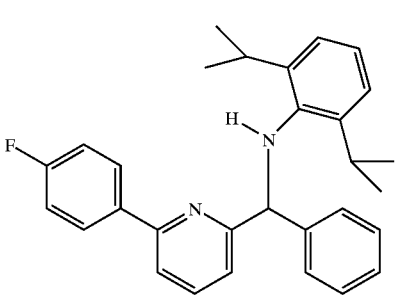
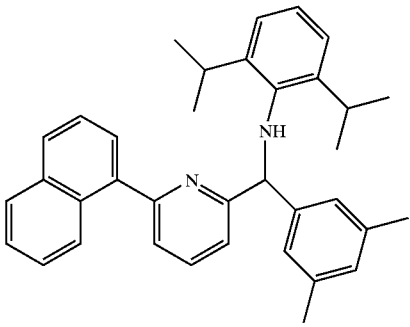
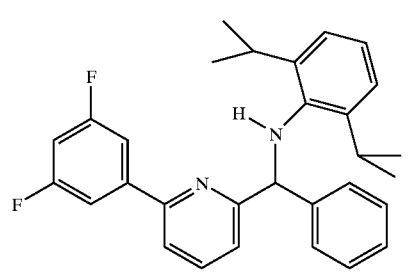

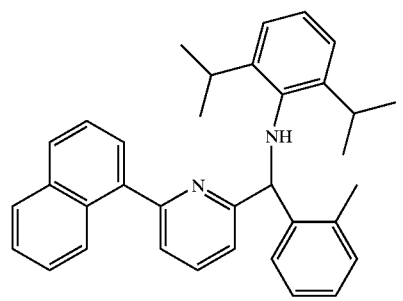

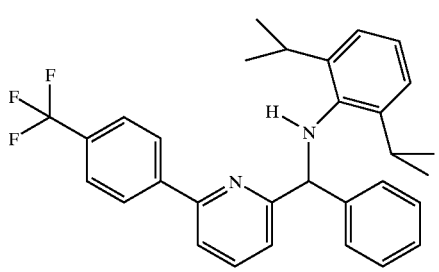

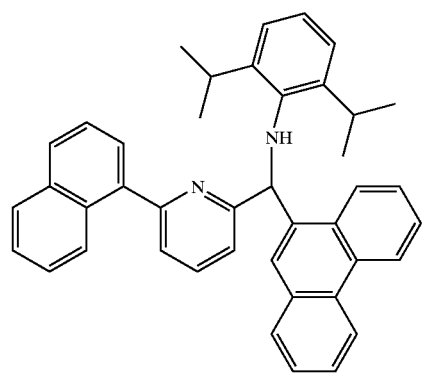

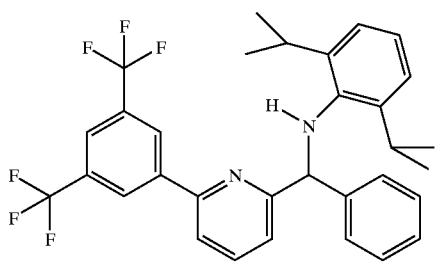

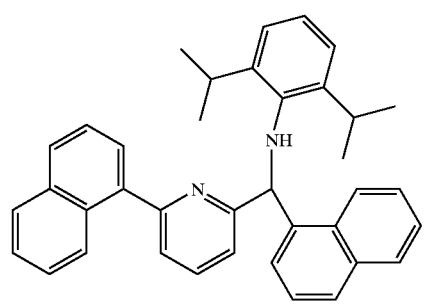

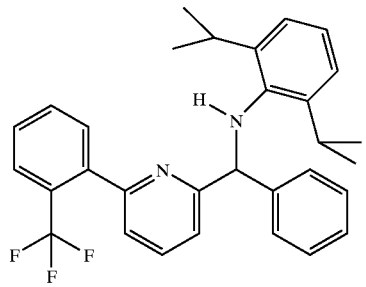

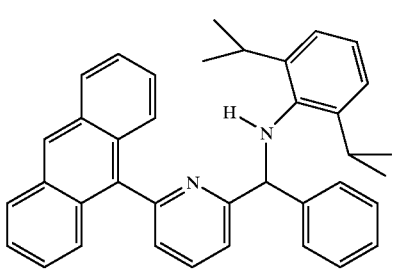

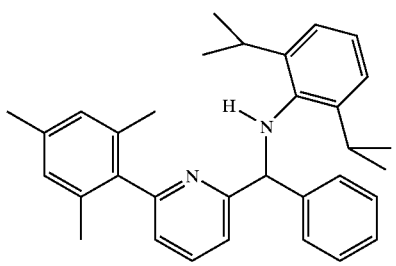

For the production of ethylene-styrene copolymers, there are different preferences depending on the type of polymer that is desired. In some embodiments, it is preferred that the ligands of either of formulas II, III, IV or V is used, particularly with $R^7$ selected from the group consisting of aryl, substituted aryl, heteroaryl, and substituted heteroaryl. Specific ligands that are preferred for ethylene-styrene copolymer production are:

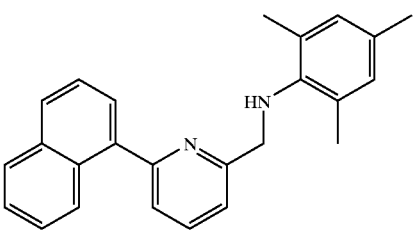

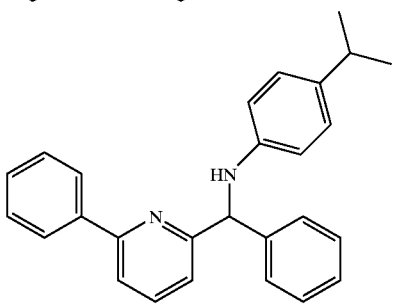

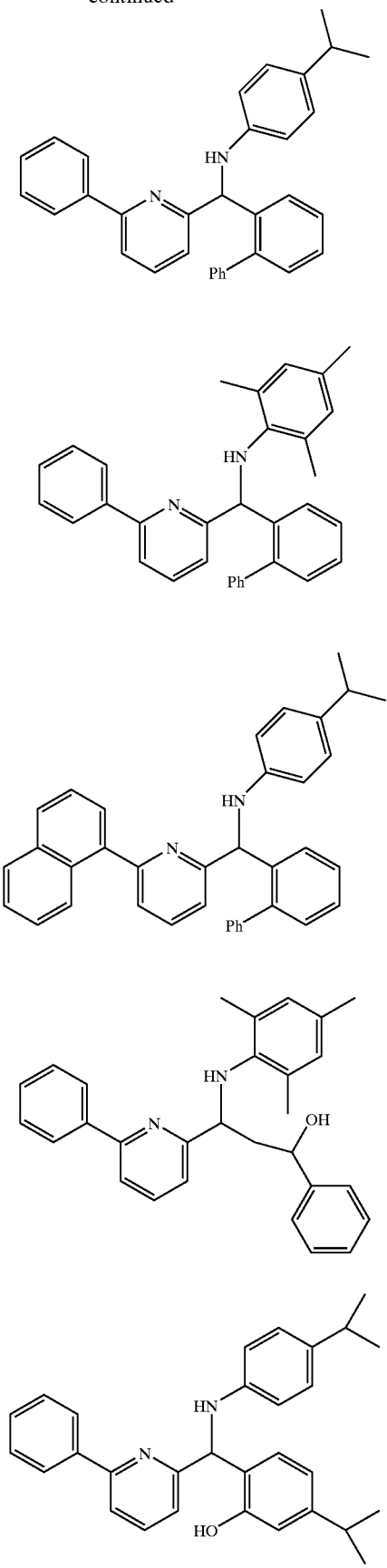
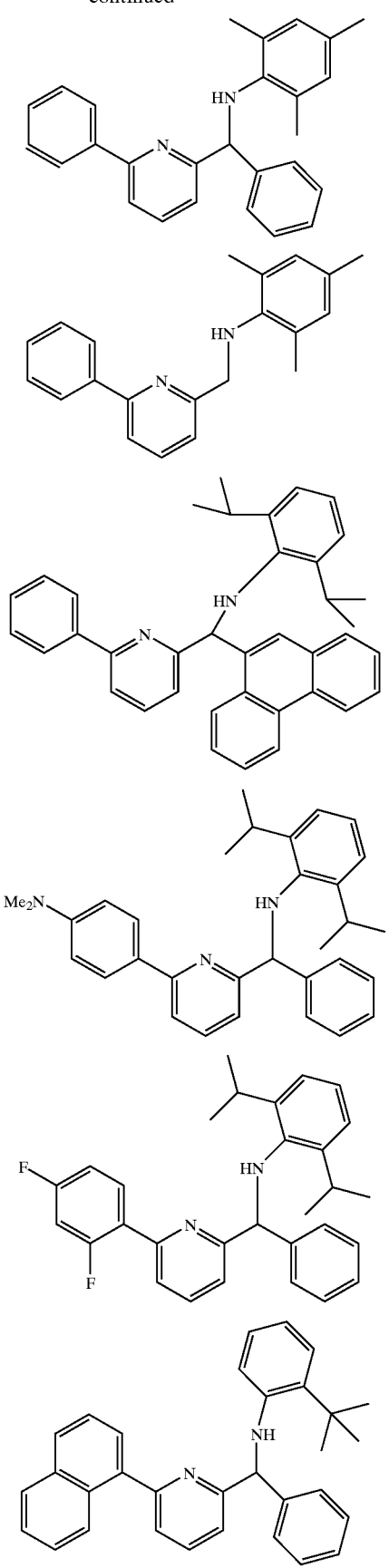

-continued
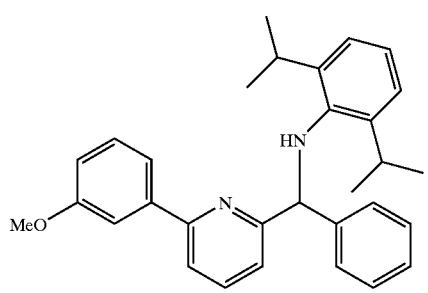
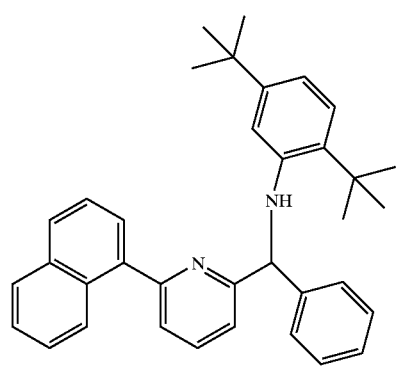
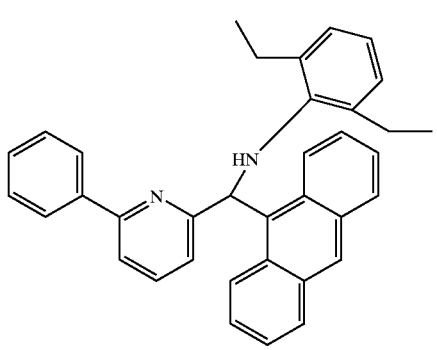
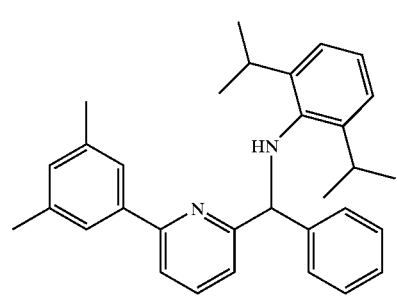
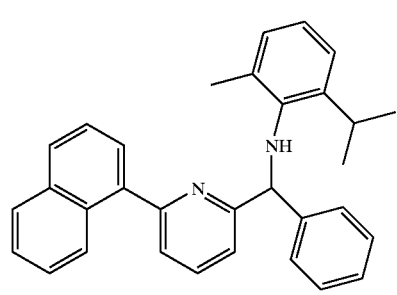
-continued
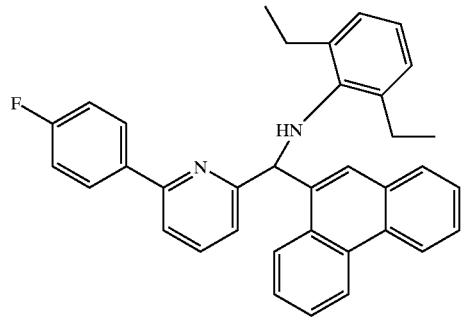
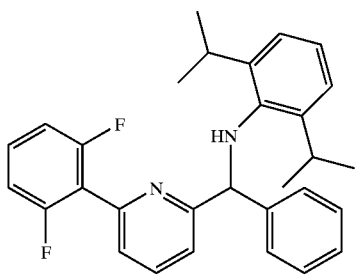
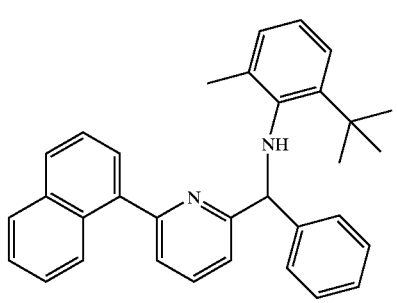
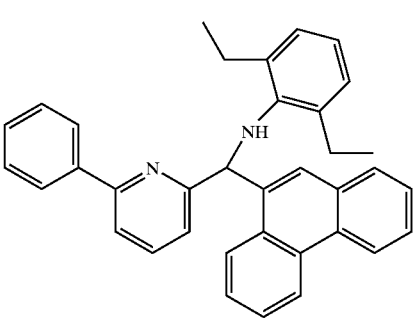
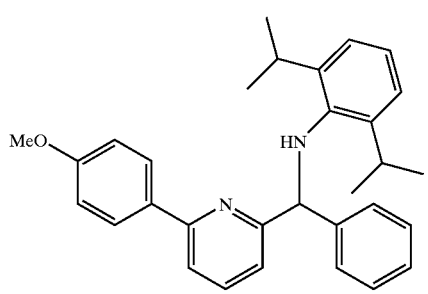

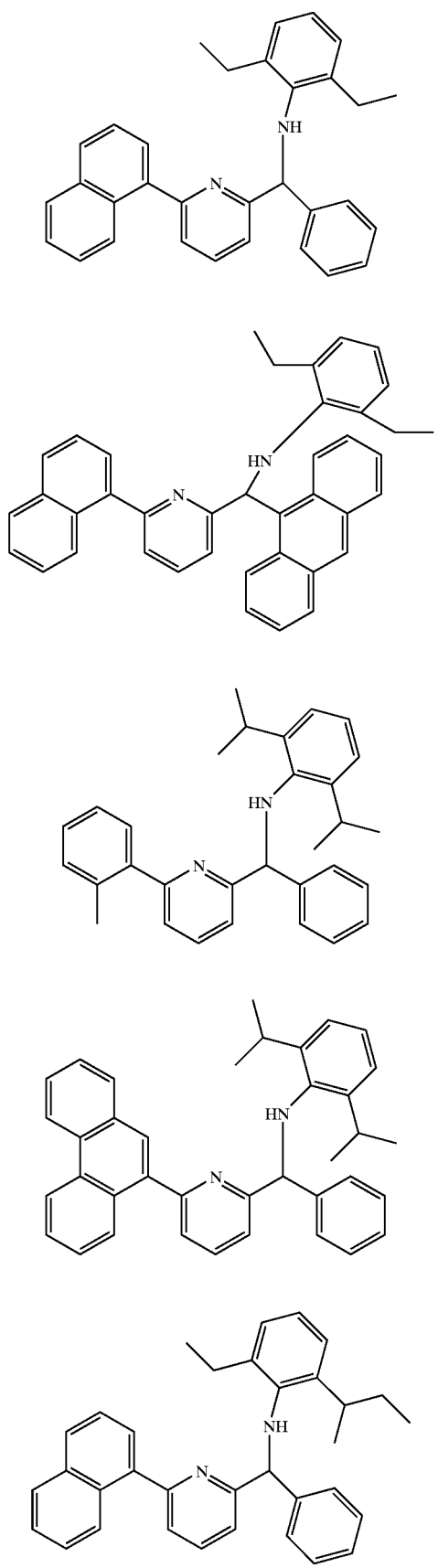
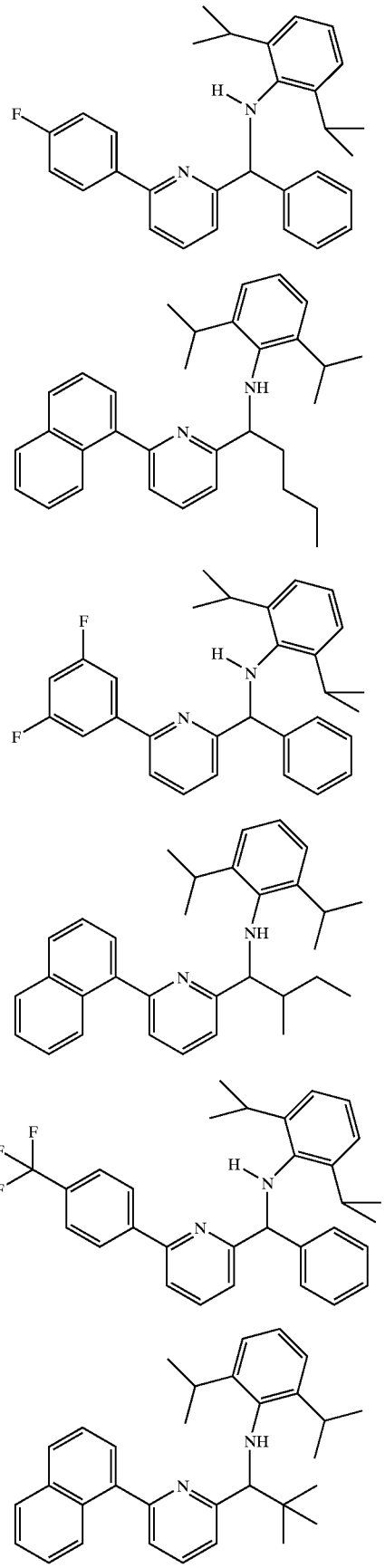

-continued
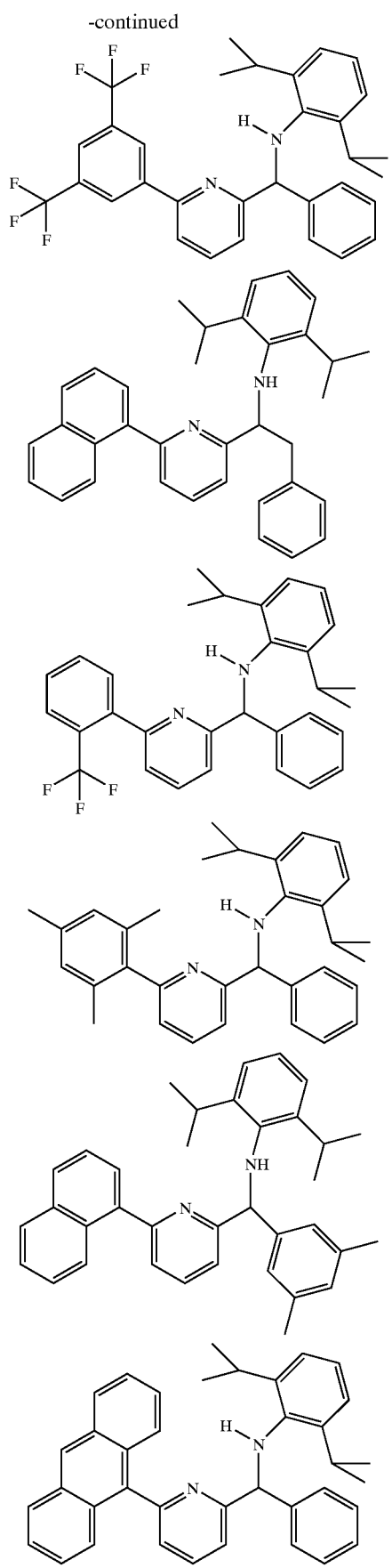
-continued
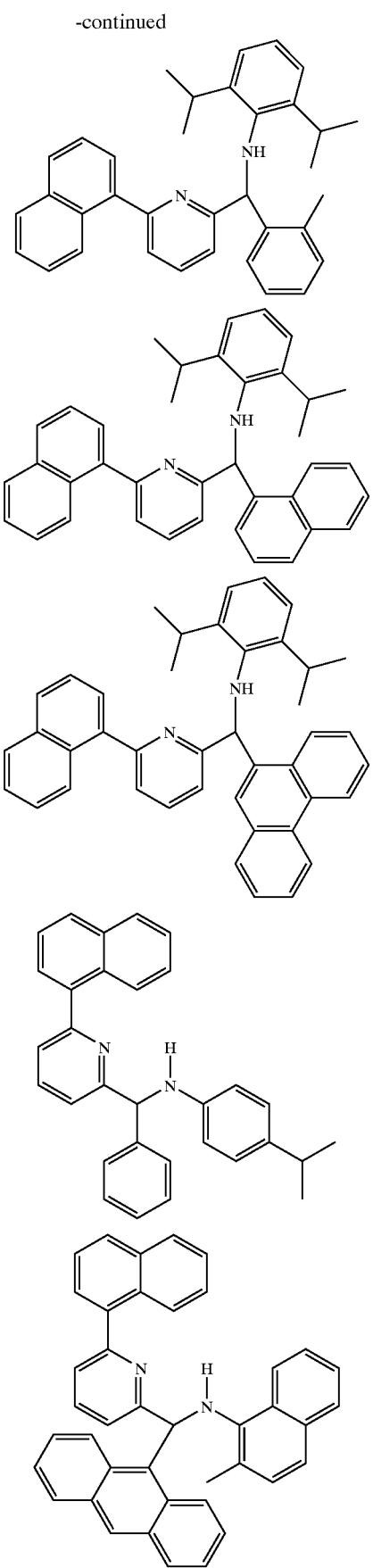

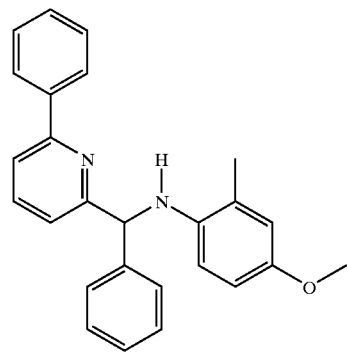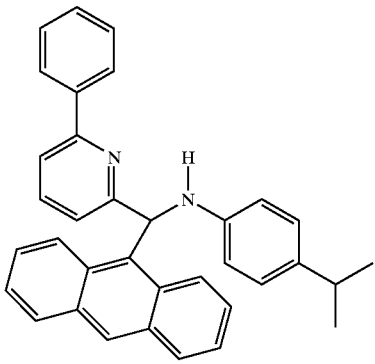

-continued

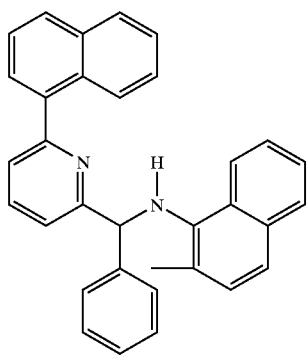

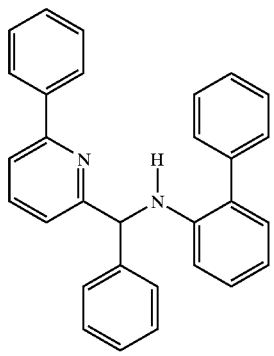

For the production of ethylene-1-octene copolymers, it is preferred that the ligands of either of formulas II, III, IV or V is used, with either or both of $R^3$ and/or $R^7$ being independently selected from the group consisting of aryl, substituted aryl, heteroaryl, and substituted heteroaryl. Specific ligands that are preferred for ethylene-1-octene copolymer production are:

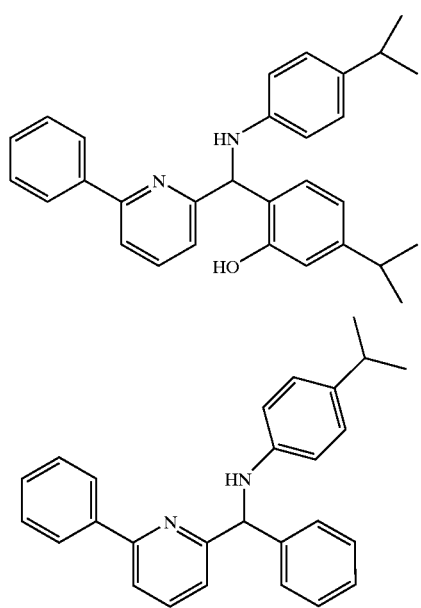

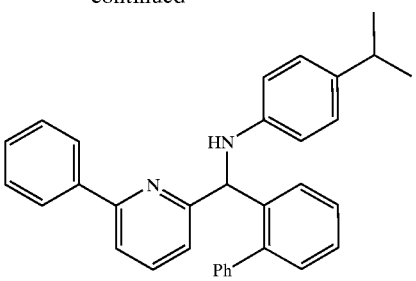

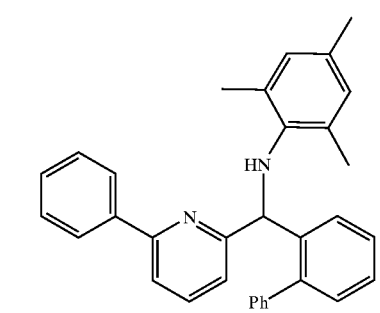

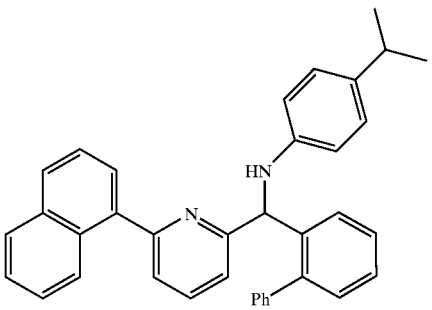

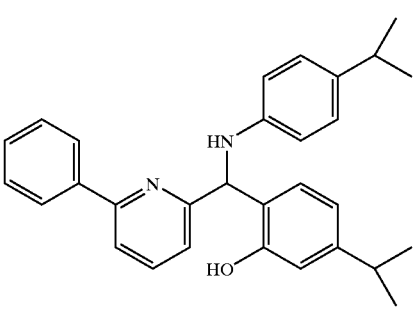

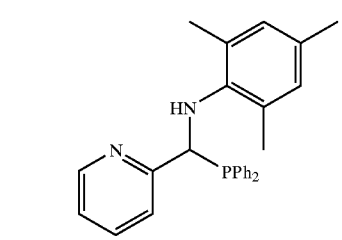

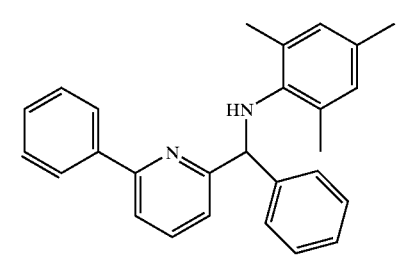

-continued

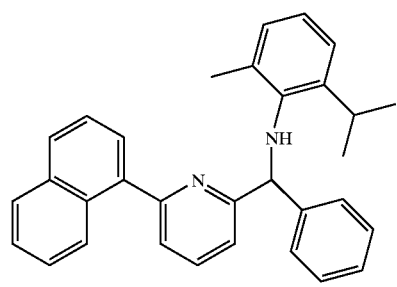
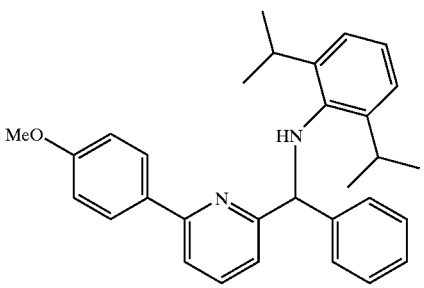
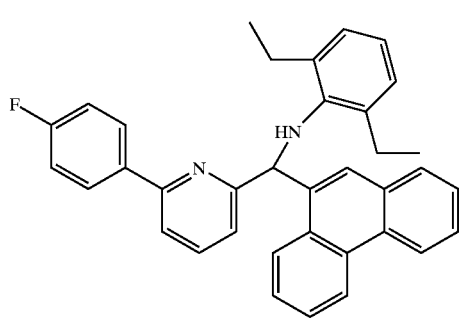
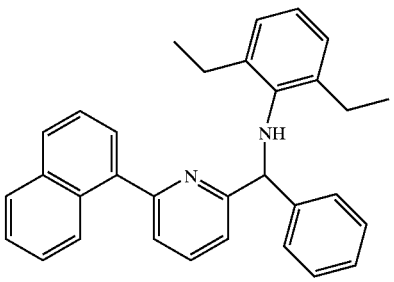
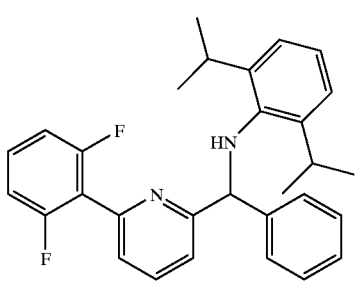
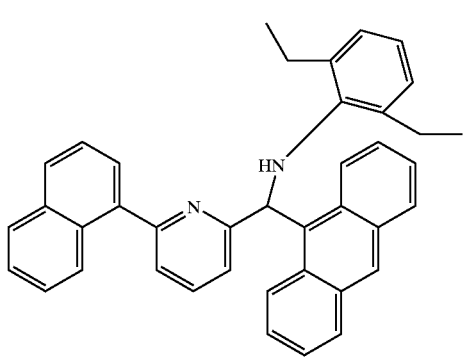
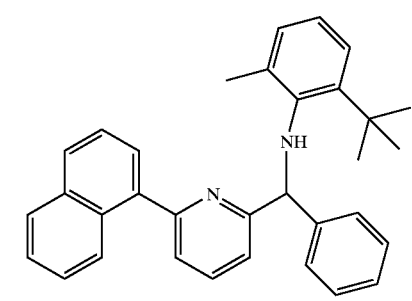
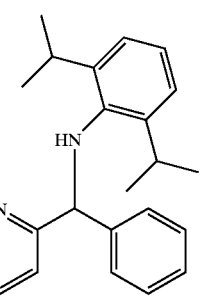
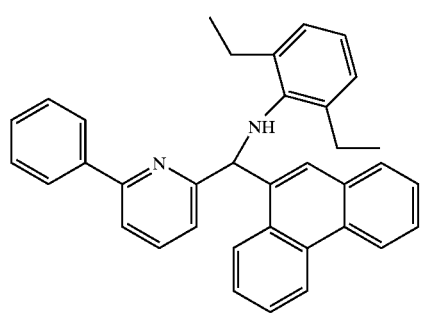
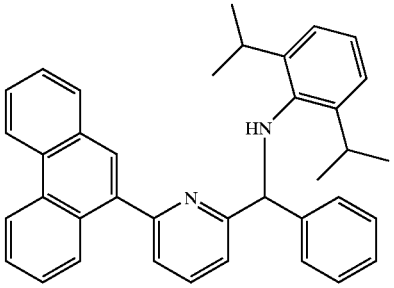

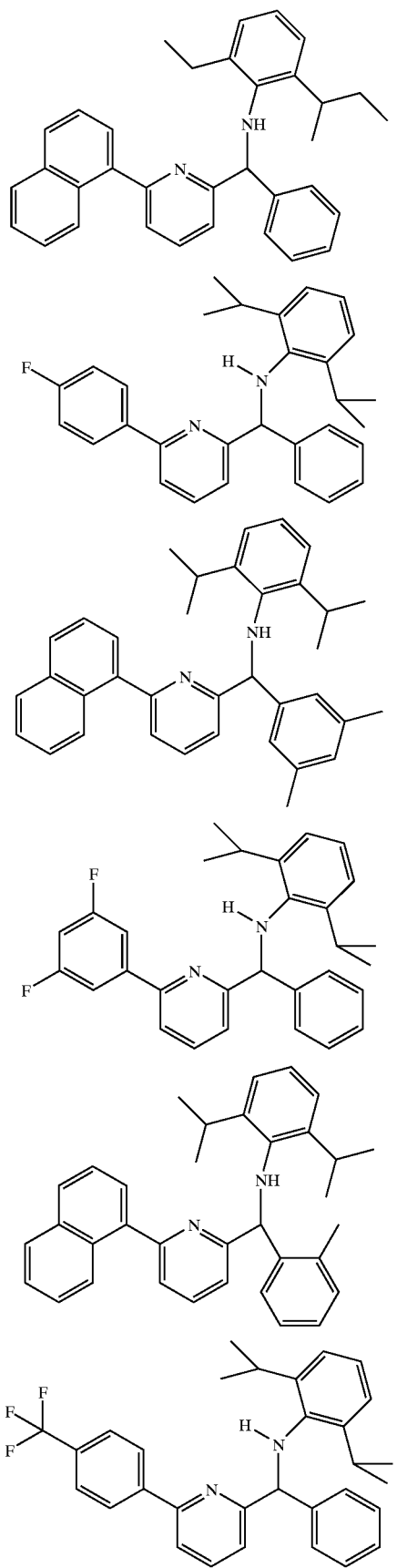
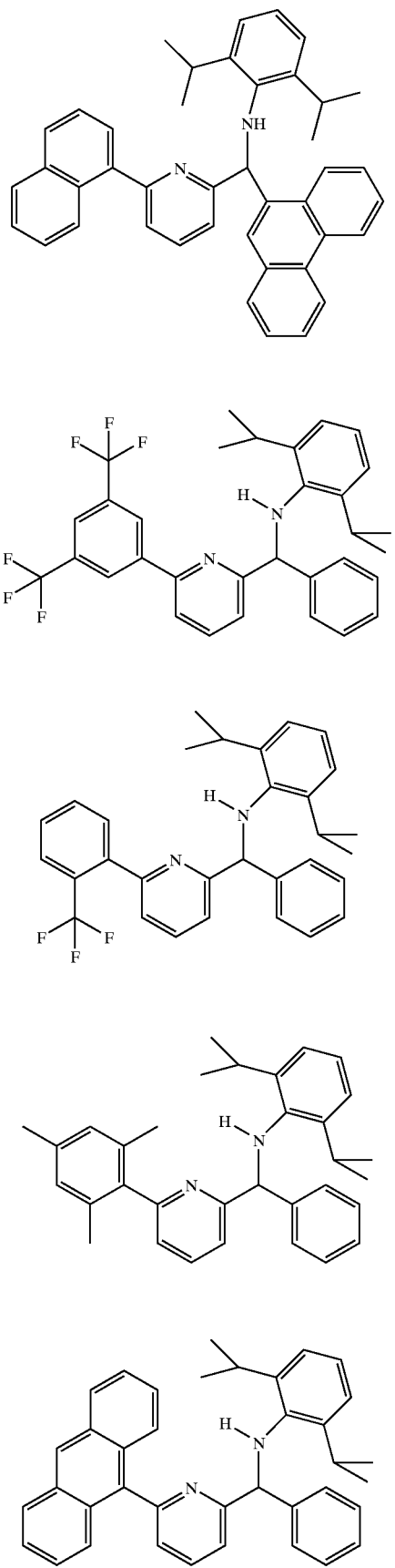

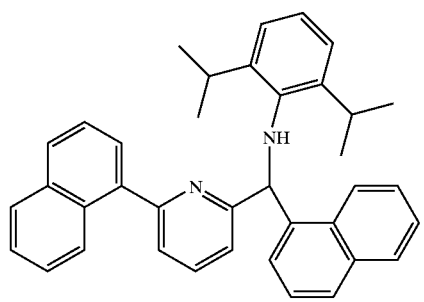
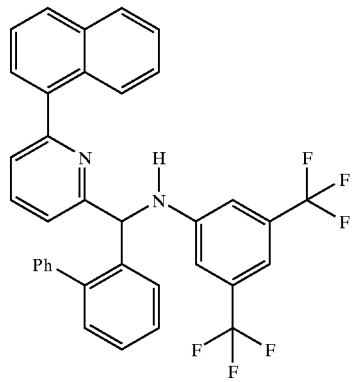
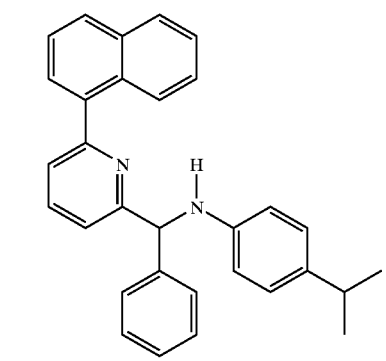
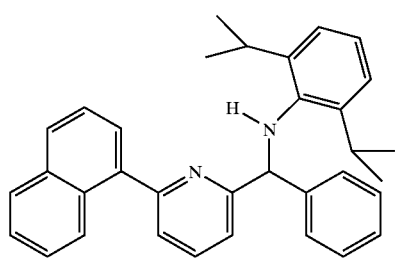
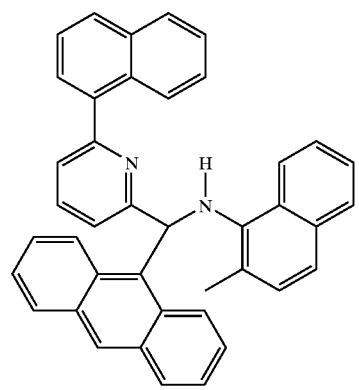
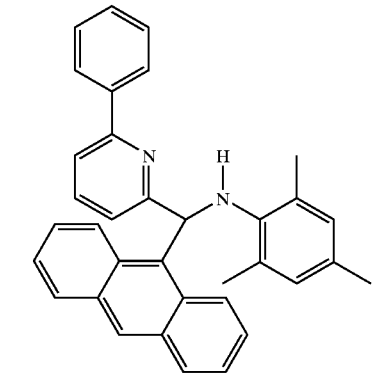
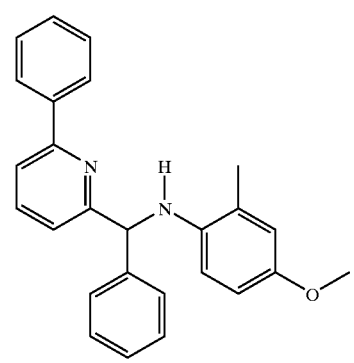
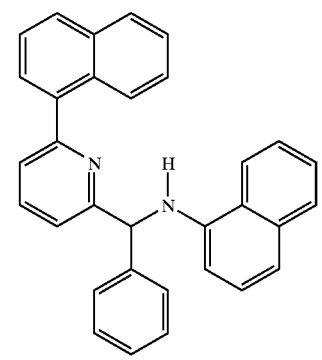

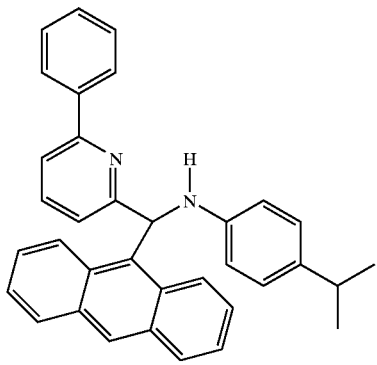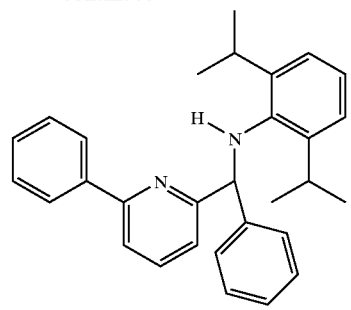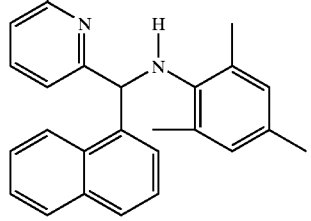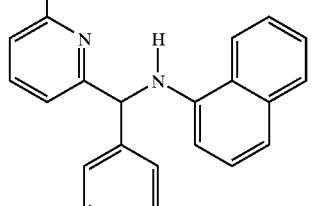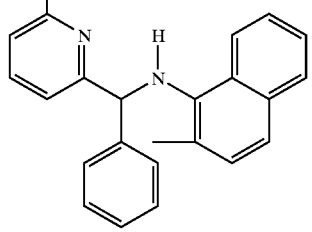

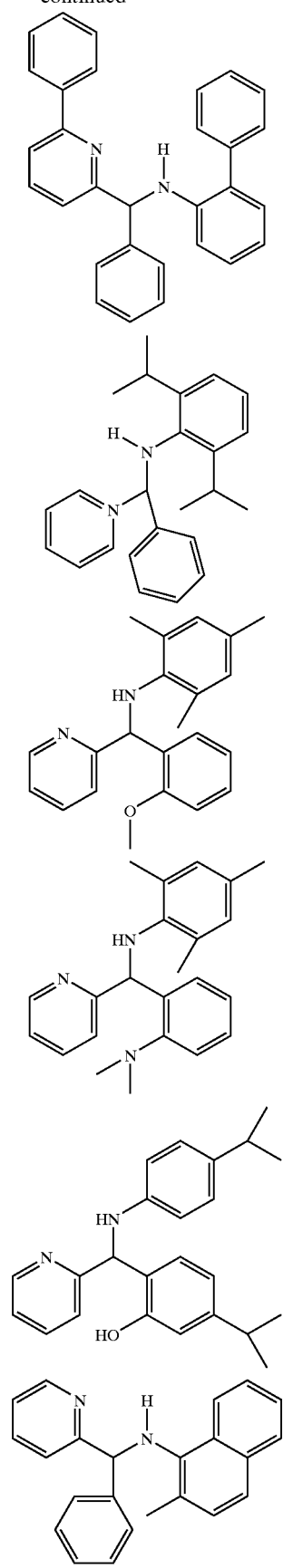

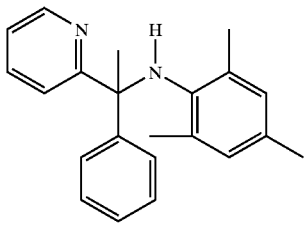

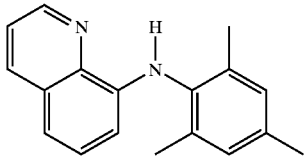

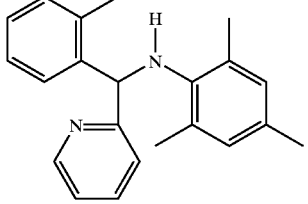

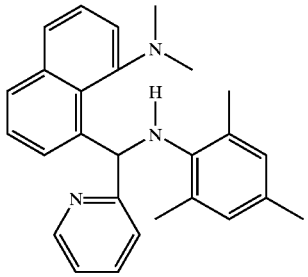

For the production of ethylene-isobutylene copolymers, it is currently preferred that $R^2$ and $R^3$ are either both hydrogen or $R^2$ is hydrogen and $R^3$ is aryl, substituted aryl or substituted alkyl. It is also important for ethylene-isobutylene copolymerization that $R^7$ is hydrogen. Specific ligands useful in this invention for the production of ethylene-isobutylene copolymers include:

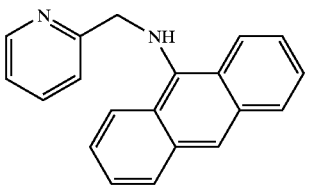

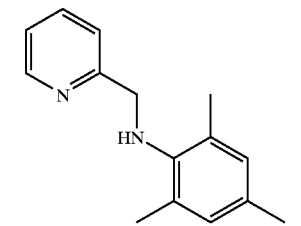

-continued

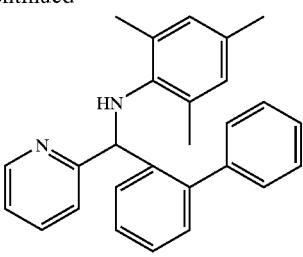

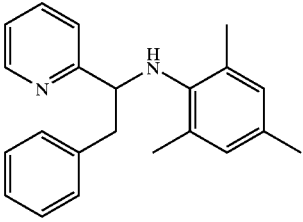

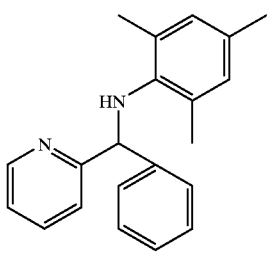

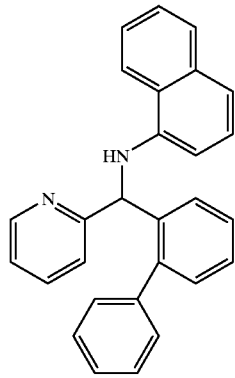

The ligands of the invention may be prepared using known procedures. See, for example, Advanced Organic Chemistry, March, Wiley, N.Y. 1992 (4$^{th}$ Ed.). Specifically, the ligands of the invention may be prepared using the two step procedure outlined in Scheme 1.

Scheme 1

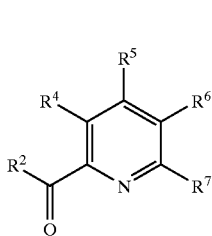

-continued

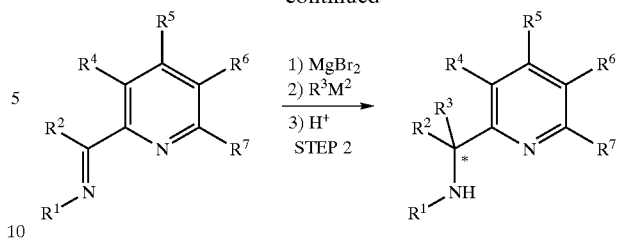

In Scheme 1, the * represents a chiral center when $R^2$ and $R^3$ are not identical; also, the R groups have the same definitions as above. Generally, $R^3M^2$ is a nucleophile such as an alkylating or arylating or hydrogenating reagent and $M^2$ is a metal such as a main group metal, or a metalloid such as boron. The alkylating, arylating or hydrogenating reagent may be a Grignard, alkyl, aryl-lithium or borohydride reagent. Scheme 1, step 2 first employs the use of complexing reagent. Preferably, as in the case of Scheme 1, magnesium bromide is used as the complexing reagent. The role of the complexing reagent is to direct the nucleophile, $R^3M^2$, selectively to the imine carbon. Where the presence of functional groups impede this synthetic approach, alternative synthetic strategies may be employed. For instance, ligands where $R^3$=phosphino can be prepared in accordance with the teachings of U.S. Pat. Nos. 6,034,240 and 6,043,363. In addition, tetra-alkylhafnium compounds or tetra-substituted alkylhafnium compounds or tetra-arylhafnium compounds or tetra-substituted arylhafnium compounds may be employed in step 2, in accordance with the teachings of U.S. Pat. No. 6,103,657, which is incorporated herein by reference. Scheme 2 further describes a synthesis process:

Scheme 2

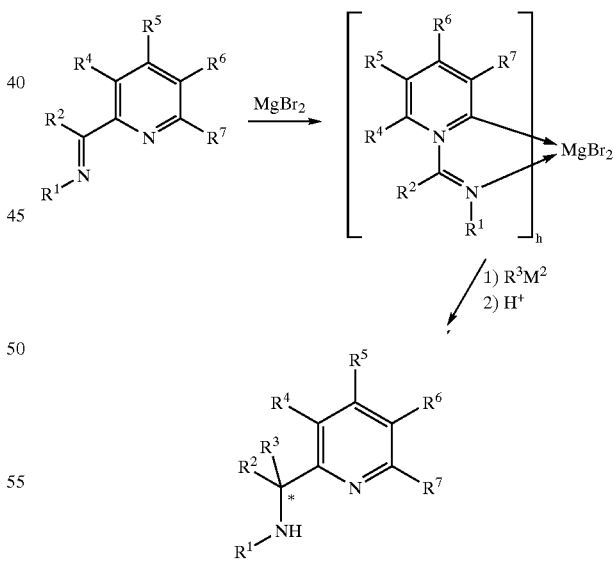

* = Chiral center where $R^2$ does not equal $R^3$

In scheme 2, h=1 or 2 and the bromine ions may or may not be bound to the magnesium. The effect of the complexation is to guide the subsequent nucleophilic attack by $R^3M^2$ to the imine carbon. Thus complexation may lead to a more selective reaction that may increase the yield of the desired ancillary ligands. Using this technique, selectivity is generally greater than about 50%, more preferably greater than about 70% and even more preferably greater than about 80%. Complexation may be particularly useful for the preparation of arrays of ancillary ligands of the type disclosed in the invention, where $R^3$ is a variable in the preparation of the ancillary ligand array. As shown in Scheme 2 by the *, where $R^2$ and $R^3$ are different, this approach also leads to the formation of a chiral center on the ancillary ligands of the invention. Under some circumstances $R^3M^2$ may be successfully added to the imine in the absence the complexing reagent. Ancillary ligands that possess chirality may be important in certain olefin polymerization reactions, particularly those that lead to a stereospecific polymer, see "Stereospecific Olefin Polymerization with Chiral Metallocene Catalysts", Brintzinger, et al., Angew. Chem. Int. Ed. Engl., 1995, Vol. 34, pp. 1143–1170, and the references therein; Bercaw et al., J. Am. Chem. Soc., 1999, Vol. 121, 564–573; and Bercaw et al., J. Am. Chem. Soc., 1996, Vol. 118, 11988–11989; each of which is incorporated herein by reference.

In the practice of high throughput methods or combinatorial materials science, introduction of diversity may be important in designing libraries or arrays. The synthetic schemes discussed herein will allow those of skill in the art to introduce diversity on the ligands, which may assist in optimizing the selection of a particular ligand for a particular polymerization reaction. Step 1 (see Scheme1) may be conducted with, for example, any combination of the pyridines and anilines shown in Tables 1 and 2 (shown in FIGS. 1 and 2, respectively). The compounds shown in Tables 1 and 2 are meant to be illustrative and non-limiting.

Compositions

Once the desired ligand is formed, it may be combined with a metal atom, ion, compound or other metal precursor compound. In some applications, the ligands of this invention will be combined with a metal compound or precursor and the product of such combination is not determined, if a product forms. For example, the ligand may be added to a reaction vessel at the same time as the metal or metal precursor compound along with the reactants, activators, scavengers, etc. Additionally, the ligand can be modified prior to addition to or after the addition of the metal precursor, e.g. through a deprotonation reaction or some other modification.

For formulas I, II, III, IV and V, the metal precursor compounds may be characterized by the general formula $Hf(L)_n$ where L is independently selected from the group consisting of halide (F, Cl, Br, I), alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, hydroxy, boryl, silyl, amino, amine, hydrido, allyl, diene, seleno, phosphino, phosphine, carboxylates, thio, 1,3-dionates, oxalates, carbonates, nitrates, sulphates, ethers, thioethers and combinations thereof; and optionally two or more L groups may be linked together in a ring structure. n is 1, 2, 3, 4, 5, or 6. The hafnium precursors may be monomeric, dimeric or higher orders thereof. It is well known that hafnium metal typically contains some amount of impurity of zirconium. Thus, this invention uses as pure hafnium as is commercially reasonable. Specific examples of suitable hafnium precursors include, but are not limited to $HfCl_4$, $Hf(CH_2Ph)_4$, $Hf(CH_2CMe_3)_4$, $Hf(CH_2SiMe_3)_4$, $Hf(CH_2Ph)_3Cl$, $Hf(CH_2CMe_3)_3Cl$, $Hf(CH_2SiMe_3)_3Cl$, $Hf(CH_2Ph)_2Cl_2$, $Hf(CH_2CMe_3)_2Cl_2$, $Hf(CH_2SiMe_3)_2Cl_2$, $Hf(NMe_2)_4$, $Hf(NEt_2)_4$, and $Hf(N(SiMe_3)_2)_2Cl_2$. Lewis base adducts of these examples are also suitable as hafnium precursors, for example, ethers, amines, thioethers, phosphines and the like are suitable as Lewis bases. Specific examples include $HfCl_4(THF)_2$, $HfCl_4(SMe_2)_2$ and $Hf(CH_2Ph)_2Cl_2(OEt_2)$.

For formulas IV and V, the metal precursor compounds may be characterized by the general formula $M(L)_n$, where M is hafnium or zirconium and each L is independently selected from the group consisting of halide (F, Cl, Br, I), alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, hydroxy, boryl, silyl, amino, amine, hydrido, allyl, diene, seleno, phosphino, phosphine, carboxylates, thio, 1,3-dionates, oxalates, carbonates, nitrates, sulphates, ethers, thioethers and combinations thereof. Optionally two or more L groups may be linked together in a ring structure. n is 4, typically. It is well known that hafnium metal typically contains some amount of impurity of zirconium. Thus, this invention uses as pure hafnium or zirconium as is commercially reasonable. Specific examples of suitable hafnium and zirconium precursors include, but are not limited to $HfCl_4$, $Hf(CH_2Ph)_4$, $Hf(CH_2CMe_3)_4$, $Hf(CH_2SiMe_3)_4$, $Hf(CH_2Ph)_3Cl$, $Hf(CH_2CMe_3)_3Cl$, $Hf(CH_2SiMe_3)_3Cl$, $Hf(CH_2Ph)_2Cl_2$, $Hf(CH_2CMe_3)_2Cl_2$, $Hf(CH_2SiMe_3)_2Cl_2$, $Hf(NMe_2)_4$, $Hf(NEt_2)_4$, and $Hf(N(SiMe_3)_2)_2Cl_2$; $ZrCl_4$, $Zr(CH_2Ph)_4$, $Zr(CH_2CMe_3)_4$, $Zr(CH_2SiMe_3)_4$, $Zr(CH_2Ph)_3Cl$, $Zr(CH_2CMe_3)_3Cl$, $Zr(CH_2SiMe_3)_3Cl$, $Zr(CH_2Ph)_2Cl_2$, $Zr(CH_2CMe_3)_2Cl_2$, $Zr(CH_2SiMe_3)_2Cl$, $Zr(NMe_2)_4$, $Zr(NEt_2)_4$, $Zr(NMe_2)_2Cl_2$, $Zr(NEt_2)_2Cl_2$, and $Zr(N(SiMe_3)_2)_2Cl_2$. Lewis base adducts of these examples are also suitable as hafnium precursors, for example, ethers, amines, thioethers, phosphines and the like are suitable as Lewis bases. Specific examples include $HfCl_4(THF)_2$, $HfCl_4(SMe_2)_2$ and $Hf(CH_2Ph)_2Cl_2(OEt_2)$.

The ligand to metal precursor compound ratio is typically in the range of about 0.01:1 to about 100:1, more preferably in the range of about 0.1:1 to about 10:1.

Metal-Ligand Complexes

This invention, in part, relates to new metal-ligand complexes. Generally, the ligand is mixed with a suitable metal precursor compound prior to or simultaneously with allowing the mixture to be contacted with the reactants (e.g., monomers). When the ligand is mixed with the metal precursor compound, a metal-ligand complex may be formed, which may be a catalyst or may need to be activated to be a catalyst. The metal-ligand complexes discussed herein are referred to as 2,1 complexes or 3,2 complexes, with the first number representing the number of coordinating atoms and second number representing the number of anionic sites on the ligand. The 2,1 complexes therefore have two coordinating atoms and a single anionic charge. Other embodiments of this invention are those complexes that have a general 3,2 coordination scheme to a metal center, with 3,2 referring to a ligand that occupies three coordination sites on the metal and two of those sites being anionic and the remaining site being a neutral Lewis base type coordination.

Looking first at the 2,1 metal-ligand complexes, the metal-ligand complexes may be characterized by the following general formula:

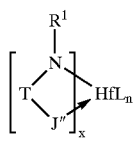

(VI)

wherein T, J'', R¹, L and n are as defined previously; and x is 1 or 2. The J'' heteroaryl may or may not datively bond, but is drawn as bonding. More specifically, the metal-ligand complexes may be characterized by the formula:

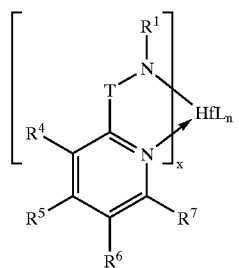

(VII)

wherein $R^1$, T, $R^4$, $R^5$, $R^6$, $R^7$, L and n are as defined previously; and x is 1 or 2. In one preferred embodiment x=1 and n=3. Additionally, Lewis base adducts of these metal-ligand complexes are also within the scope of the invention, for example, ethers, amines, thioethers, phosphines and the like are suitable as Lewis bases.

More specifically, the metal-ligand complexes of this invention may be characterized by the general formula:

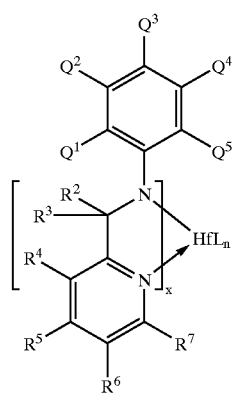

(VIII)

wherein the variables are generally defined above. Thus, e.g., $Q^2$, $Q^3$, $Q^4$, $R^2$, $R^3$, $R^4$, $R^5$, $R^6$ and $R^7$ are independently selected from the group consisting of hydrogen, alkyl, substituted alkyl, cycloalkyl, substituted cycloalkyl, heteroalkyl, substituted heteroalkyl, heterocycloalkyl, substituted hetercycloalkyl, aryl, substituted aryl, heteroaryl, substituted heteroaryl, alkoxyl, aryloxyl, silyl, boryl, phosphino, amino, thio, seleno, nitro, and combinations thereof; optionally, two or more $R^4$, $R^5$, $R^6$, $R^7$ groups may be joined to form a fused ring system having from 3–50 non-hydrogen atoms in addition to the pyridine ring, e.g. generating a quinoline group; also, optionally, any combination of $R^2$, $R^3$ and $R^4$ may be joined together in a ring structure; $Q^1$ and $Q^5$ are selected from the group consisting of alkyl, substituted alkyl, cycloalkyl, substituted cycloalkyl, aryl, substituted aryl, provided that $Q^1$ and $Q^5$ are not both methyl; and each L is independently selected from the group consisting of halide, alkyl, substituted alkyl, cycloalkyl, substituted cycloalkyl, heteroalkyl, substituted heteroalkyl heterocycloalkyl, substituted heterocycloalkyl, aryl, substituted aryl, heteroaryl, substituted heteroaryl, alkoxy, aryloxy, hydroxy, boryl, silyl, amino, amine, hydrido, allyl, diene, seleno, phosphino, phosphine, carboxylates, thio, 1,3-dionates, oxalates, carbonates, nitrates, sulphates, ethers, thioethers and combinations thereof; and optionally two L groups may be linked together in a ring structure; n is 1, 2, 3, 4, 5, or 6; and x=1 or 2.

In other embodiments, the 2,1 metal-ligand complexes can be characterized by the general formula:

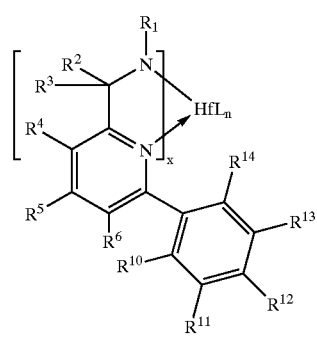

(IX)

wherein the variables are generally defined above.

In still other embodiments, the 2,1 metal-ligand complexes of this invention can be characterized by the general formula:

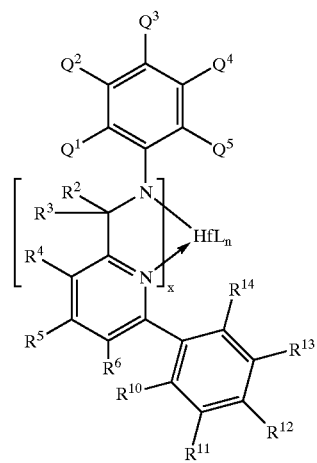

(X)

wherein the variables are generally defined above. The more specific embodiments of the metal-ligand complexes of formulas VI, VII, VIII, IX and X are explained above with regard to the specifics described for the ligands and metal precursors.

Lewis base adducts of these complexes are also suitable, for example, ethers, amines, thioethers, phosphines and the like are suitable as Lewis bases (note the definition of L).

Turning to the 3,2 metal-ligand complexes of this invention, the metal-ligand complexes in this aspect of this invention may be generally characterized by the general formula:

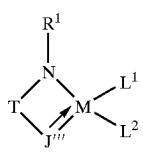
(XI)

where M is zirconium or hafnium;
$R^1$ and T are defined above;
J''' being selected from the group of substituted heteroaryls with 2 atoms bonded to the metal M, at least one of those 2 atoms being a heteroatom, and with one atom of J''' is bonded to M via a dative bond, the other through a covalent bond; and $L^1$ and $L^2$ are independently selected from the group consisting of halide, alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, hydroxy, boryl, silyl, amino, amine, hydrido, allyl, diene, seleno, phosphino, phosphine, carboxylates, thio, 1,3-dionates, oxalates, carbonates, nitrates, sulphates, and combinations thereof; and optionally the L groups may be linked together in a ring structure.

More specifically, the 3,2 metal-ligand complexes of this invention may be characterized by the general formula:

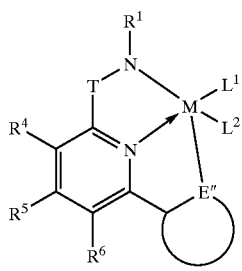
(XII)

where M is zirconium or hafnium;
T, $R^1$, $R^4$, $R^5$, $R^6$, $L^1$ and $L^2$ are defined above; and
E'' is either carbon or nitrogen and is part of an cyclic aryl, substituted aryl, heteroaryl, or substituted heteroaryl group.

Even more specifically, the 3,2 metal-ligand complexes of this invention may be characterized by the general formula:

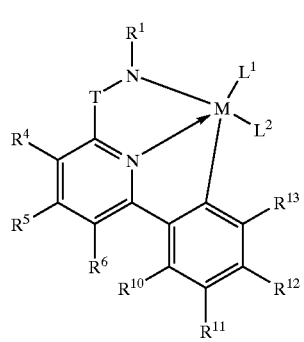
(XIII)

where M is zirconium or hafnium; and
T, $R^1$, $R^4$, $R^5$, $R^6$, $R^{10}$, $R^{11}$, $R^{12}$, $R^{13}$, $L^1$ and $L^2$ are defined above.

Still even more specifically, the 3,2 metal-ligand complexes of this invention may be characterized by the general formula:

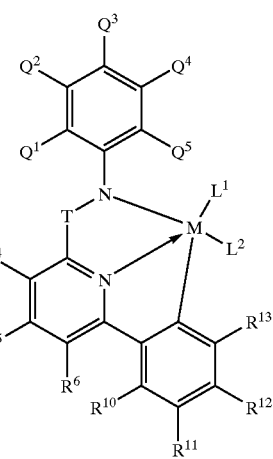
(XIV)

where M is zirconium or hafnium; and
T, $R^1$, $R^4$, $R^5$, $R^6$, $R^{10}$, $R^{11}$, $R^{12}$, $R^{13}$, $Q^1$, $Q^2$, $Q^3$, $Q^4$, $Q^5$, $L^1$ and $L^2$ are defined above.

The more specific embodiments of the metal-ligand complexes of formulas XI, XII, XIII and XIV are explained above with regard to the specifics described for the ligands and metal precursors. Lewis base adducts of these complexes are also suitable, for example, ethers, amines, thioethers, phosphines and the like are suitable as Lewis bases.

In addition, preferences for the substituents on the ligands for production of the particular polymers discussed above (e.g., isotactic polypropylene) apply to the metal-ligand complexes just described. For isotactic polypropylene it is currently preferred that M is hafnium, although this preference is only slight as compared to zirconium. By "slight" here, it is meant that zirconium metal based polymerization of propylene for isotactic polypropylene shows similar tacticity control as compared to hafnium metal based polymerization, however, the hafnium based catalysts tend to show better polymerization activity and performance overall.

For isotactic polypropylene production, it is currently preferred that $L^1$ and $L^2$ are the same and selected from the group consisting of alkyl and dialkyl amino, more specifically from the group consisting of methyl and dimethylamino.

As above, for production of isotactic polypropylene, $R^2$ and $R^3$ are not the same group, leading to a chiral center on the carbon atom from which $R^2$ and $R^3$ stem. In more specific embodiments, $R^2$ is hydrogen. In more specific embodiments for isotactic polypropylene production $R^3$ is selected from the group consisting of hydrogen, halide, alkyl, substituted alkyl, cycloalkyl, substituted cycloalkyl, heteroalkyl, substituted heteroalkyl, heterocycloalkyl, substituted hetercycloalkyl, aryl, substituted aryl, heteroaryl, substituted heteroaryl, alkoxy, aryloxy, silyl, boryl, phosphino, amino, thio, seleno, nitro, and combinations thereof. In more specific embodiments for isotactic polypropylene production $R^3$ is aryl, substituted aryl, heteroaryl or substituted heteroaryl. In more specific embodiments for isotactic polypropylene production $R^3$ is selected from the group consisting of benzyl, phenyl, 2-biphenyl, 2-dimethylaminophenyl, 2-methoxyphenyl, anthracenyl, mesityl, 2-pyridyl, 3,5-dimethylphenyl, o-tolyl and phenanthrenyl.

In the above formulas, $R^{10}$, $R^{11}$, $R^{12}$ and $R^{13}$ are independently selected from the group consisting of hydrogen, halide, alkyl, substituted alkyl, cycloalkyl, substituted cycloalkyl, heteroalkyl, substituted heteroalkyl, heterocycloalkyl, substituted hetercycloalkyl, aryl, substituted aryl, heteroaryl, substituted heteroaryl, alkoxy, aryloxy, silyl, boryl, phosphino, amino, thio, seleno, nitro, and combinations thereof; optionally, two or more $R^{10}$, $R^{11}$, $R^{12}$ and $R^{13}$ groups may be joined to form a fused ring system having from 3–50 non-hydrogen atoms. Particular embodiments include, for example, for isotactic polypropylene production, it is currently preferred that $R^{10}$, $R^{11}$, $R^{12}$, $R^{13}$, are each hydrogen; or one or more of $R^{10}$, $R^{11}$, $R^{12}$, $R^{13}$ are methyl, fluoro, trifluoromethyl, methoxy, or dimethylamino; or where $R^{10}$ and $R^{11}$ are joined to form a benzene ring and $R^{12}$ and $R^{13}$ are each hydrogen (thus forming a napthyl group with the existing phenyl ring).

Specific 2,1 and 3,2 metal complexes that are useful for the production of isotactic polypropylene include:

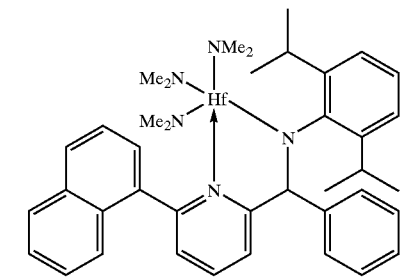

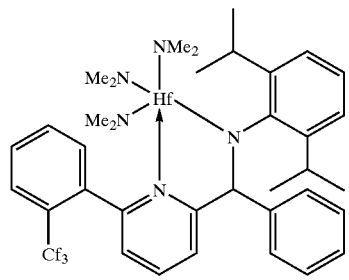

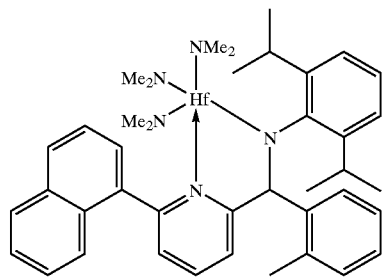

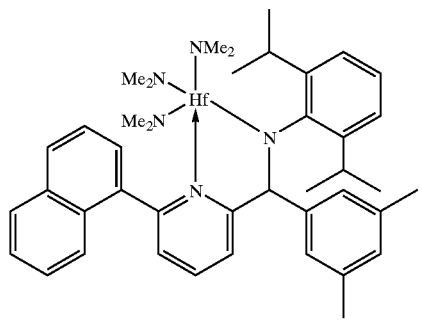

-continued

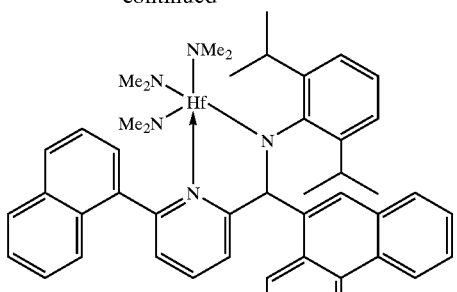

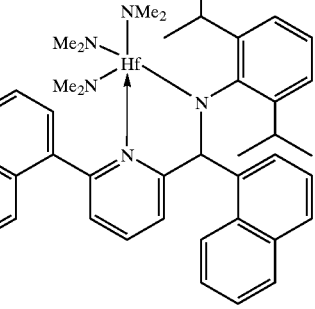

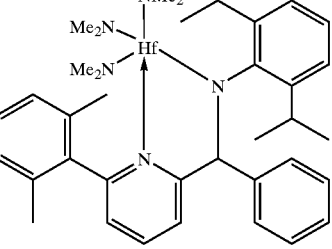

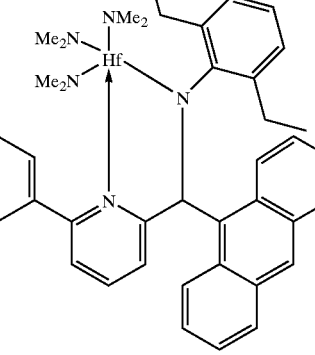

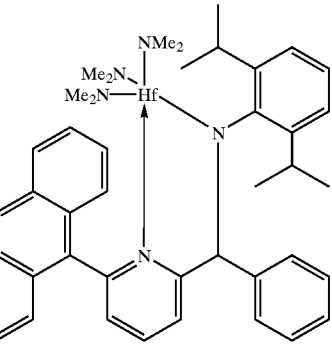

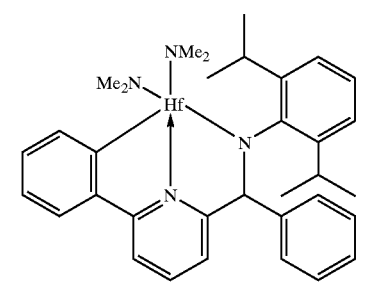
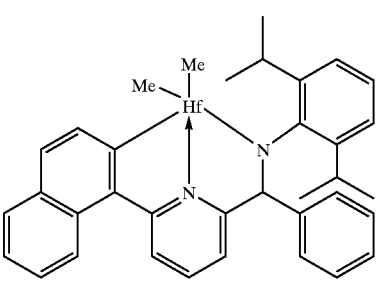
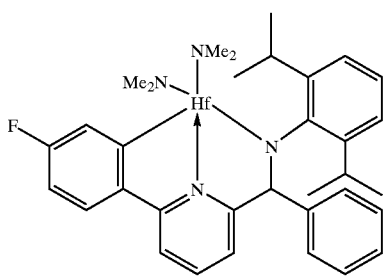
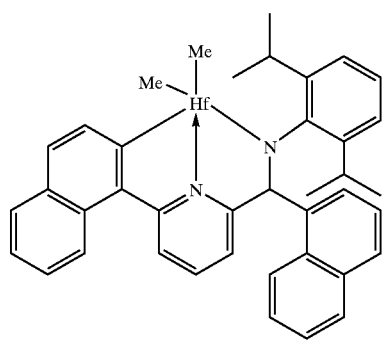
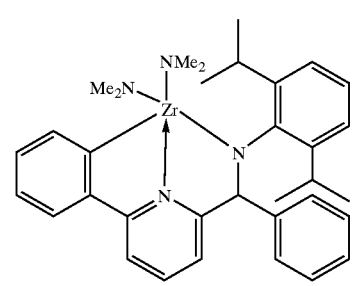
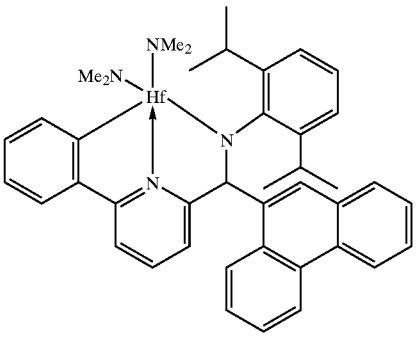
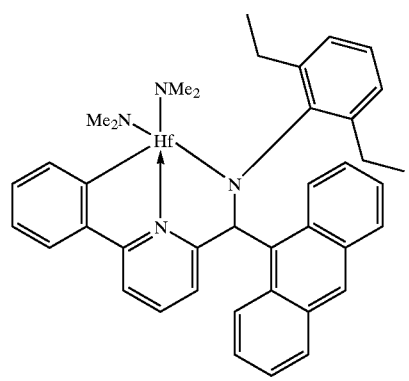
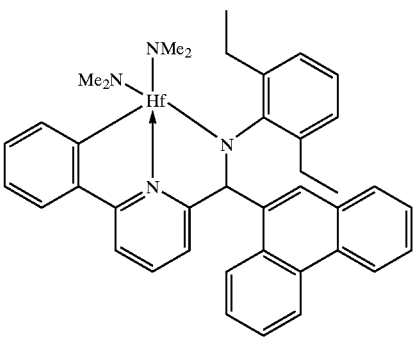
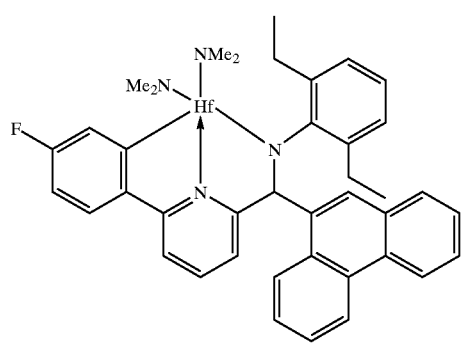
For the production of ethylene-styrene copolymers, there are different preferences depending on the type of polymer that is desired. In some embodiments, it is preferred that the above formulas for complexes are used, particularly with $R^7$ selected from the group consisting of aryl, substituted aryl, heteroaryl, and substituted heteroaryl. Specific 2,1 and 3,2 complexes that are preferred for ethylene-styrene copolymer production include:
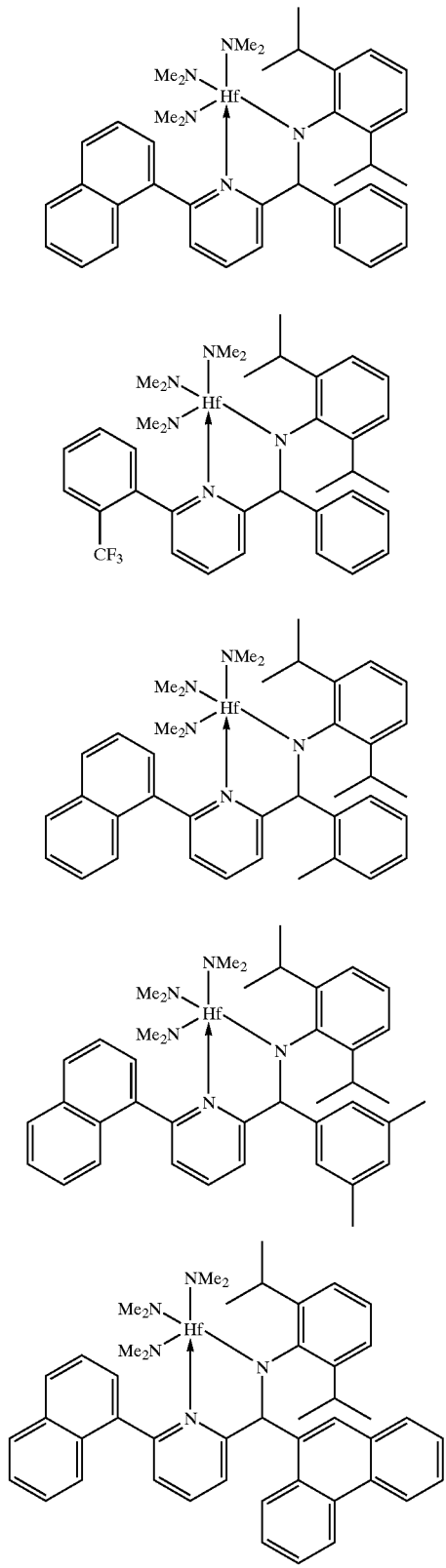
-continued
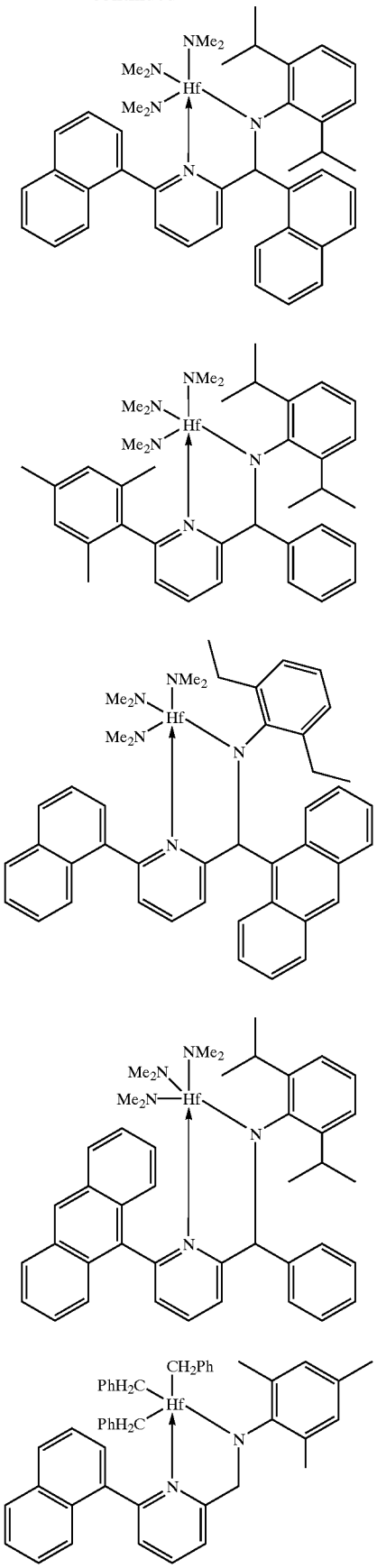

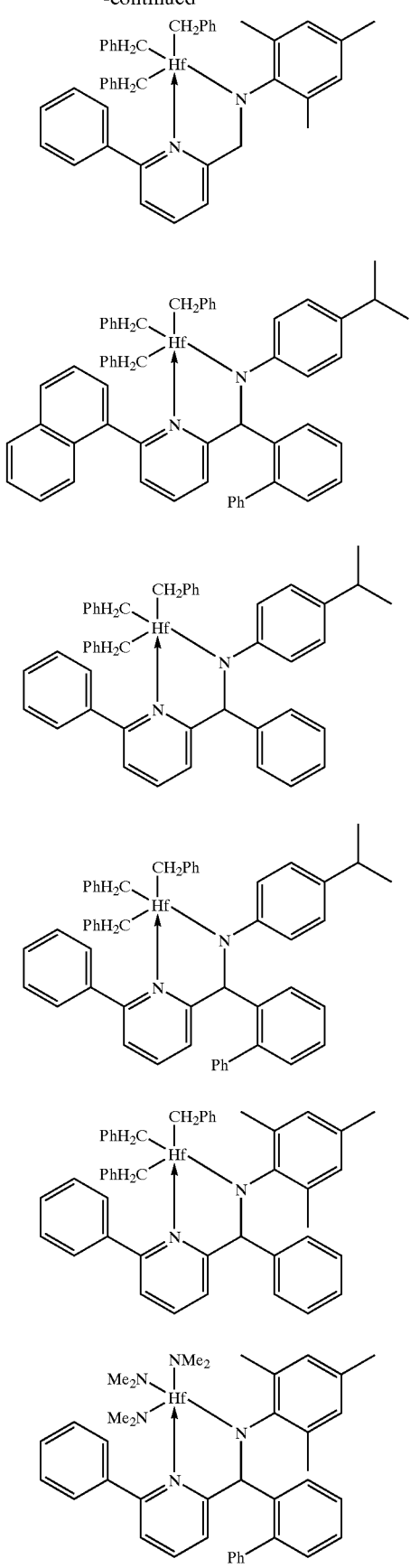
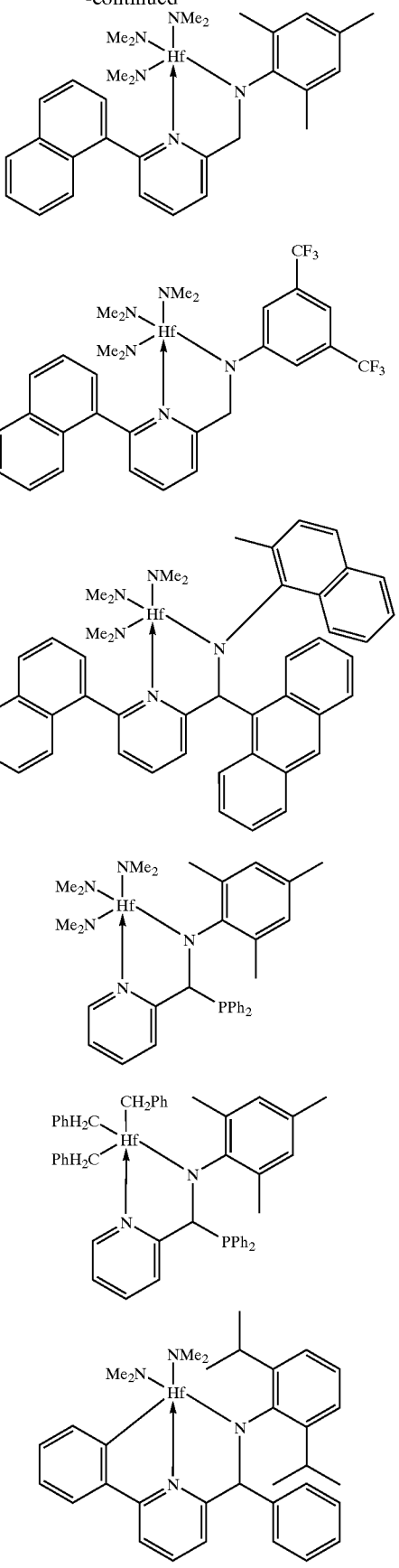

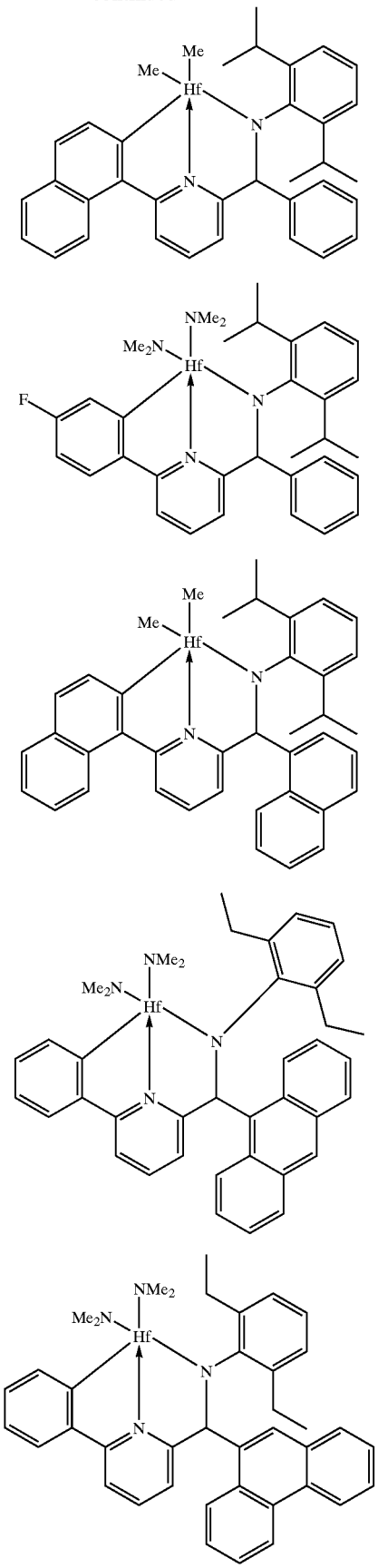

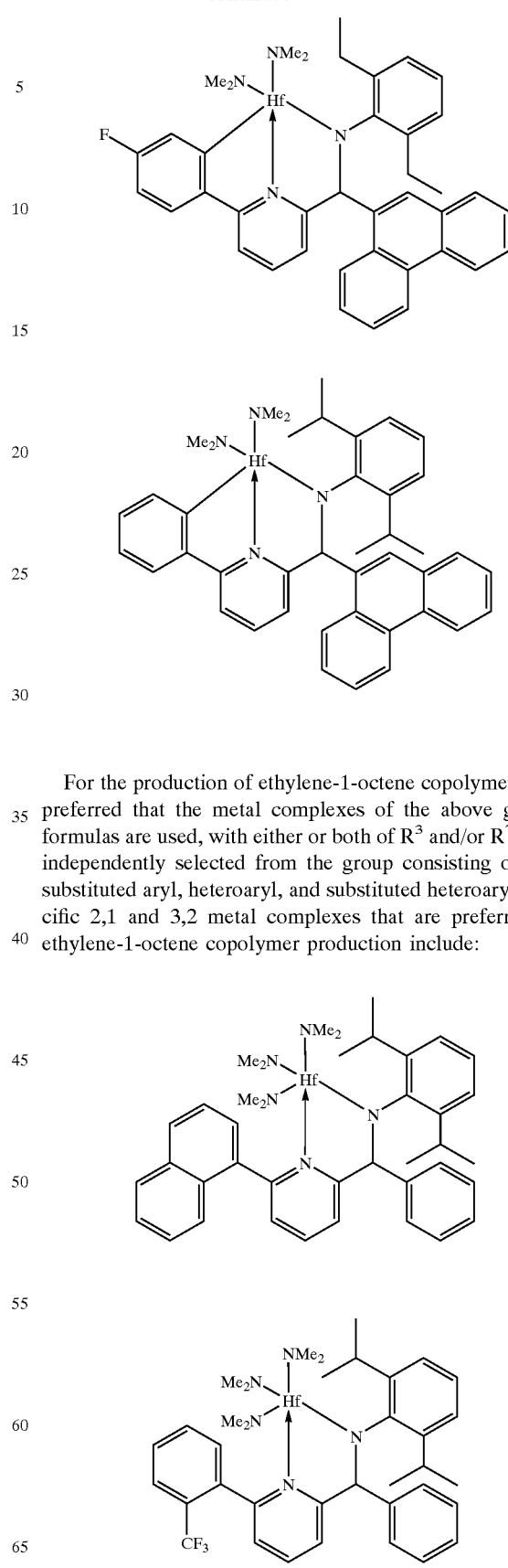

For the production of ethylene-1-octene copolymers, it is preferred that the metal complexes of the above general formulas are used, with either or both of $R^3$ and/or $R^7$ being independently selected from the group consisting of aryl, substituted aryl, heteroaryl, and substituted heteroaryl. Specific 2,1 and 3,2 metal complexes that are preferred for ethylene-1-octene copolymer production include:

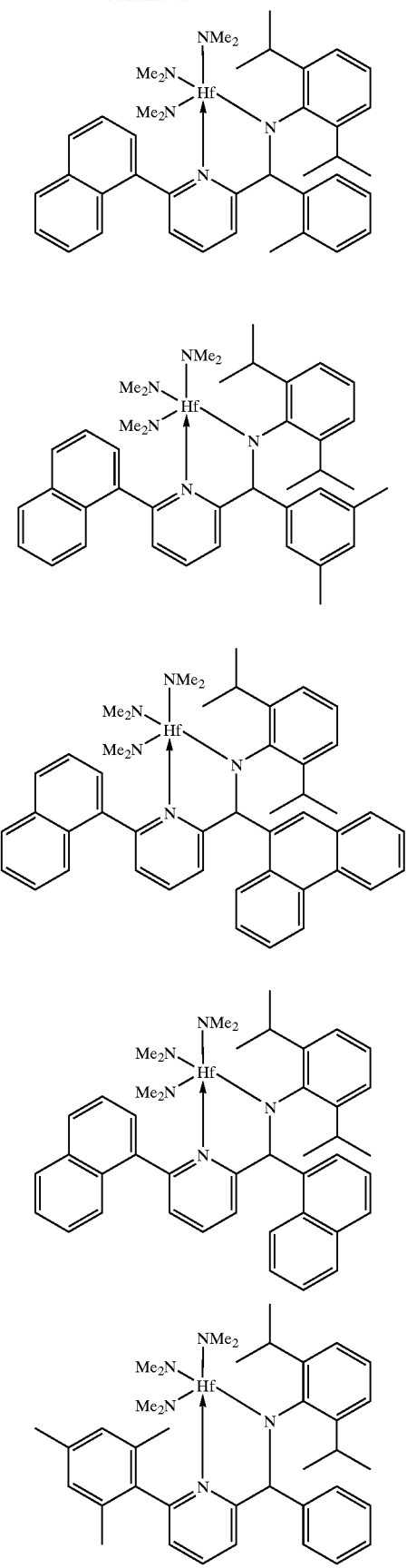
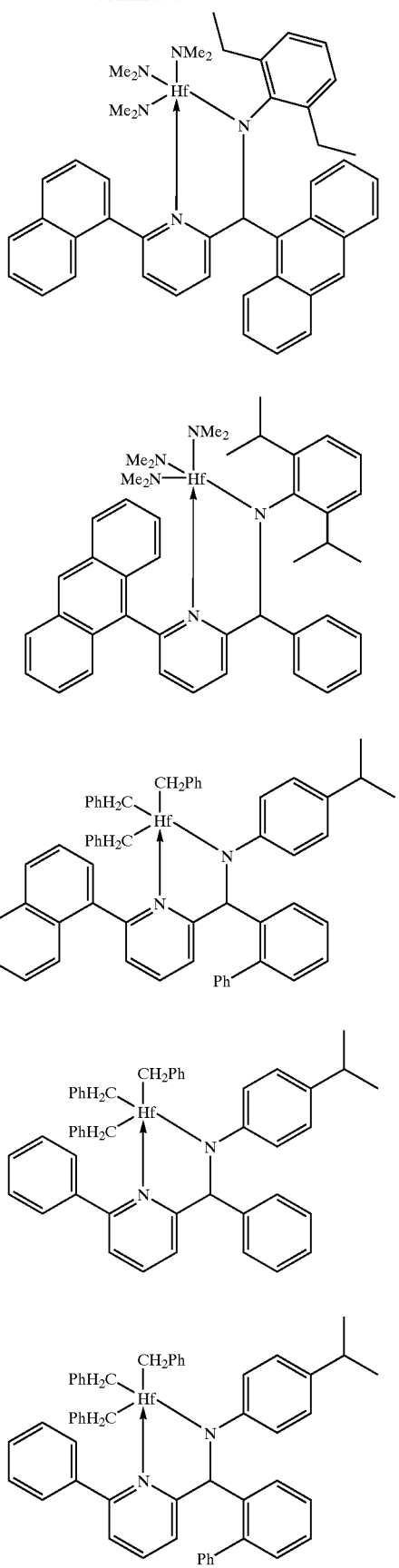

-continued
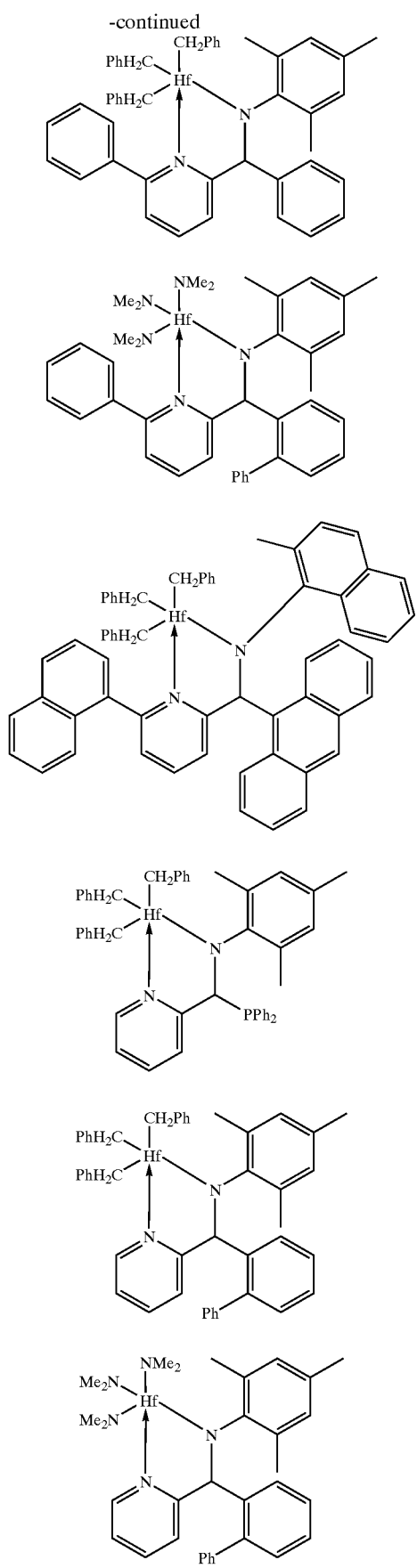
-continued
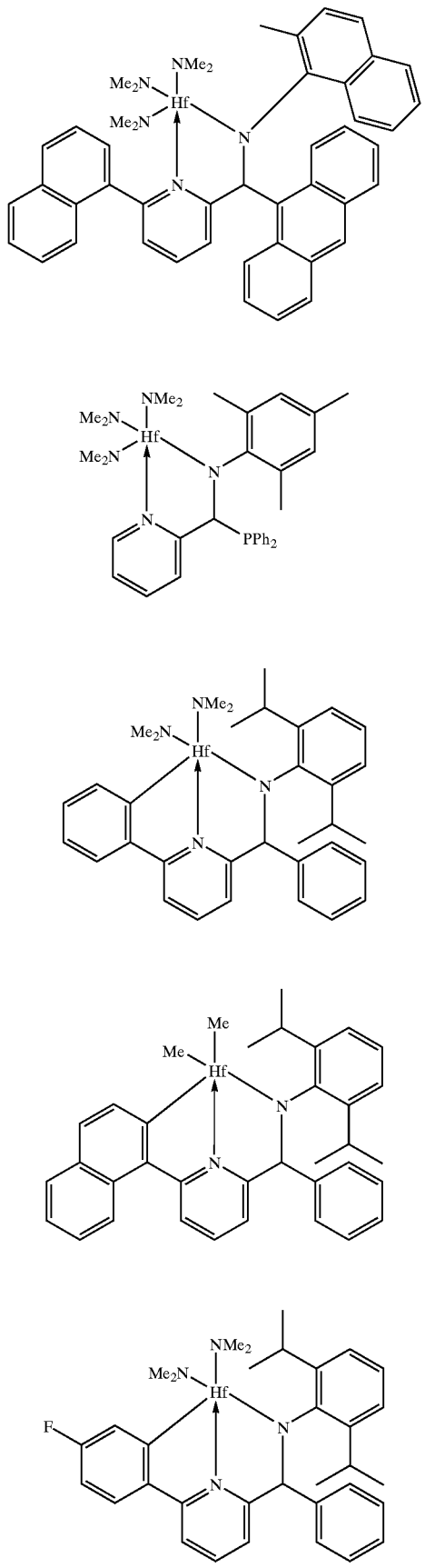

-continued

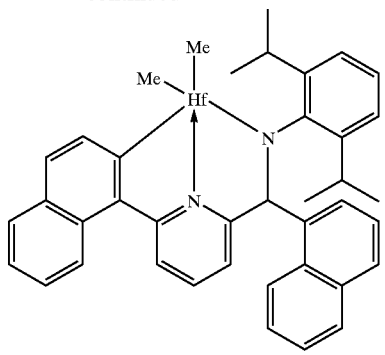

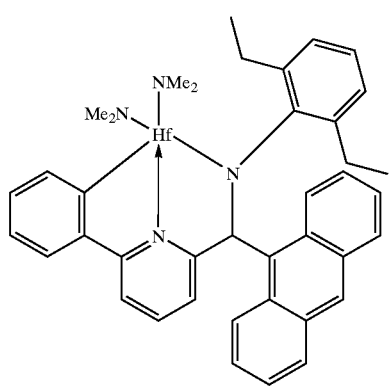

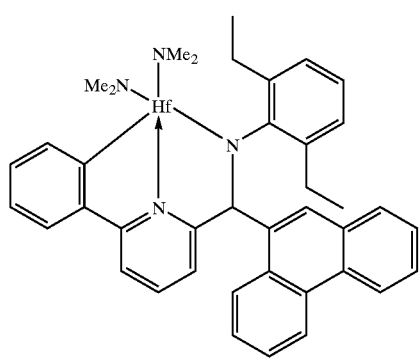

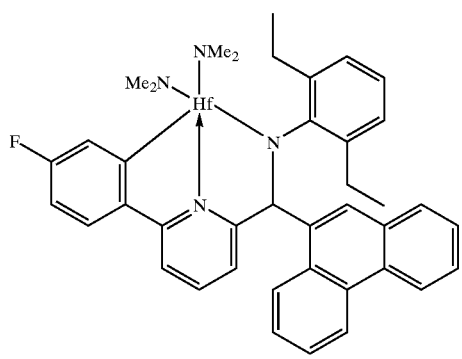

-continued

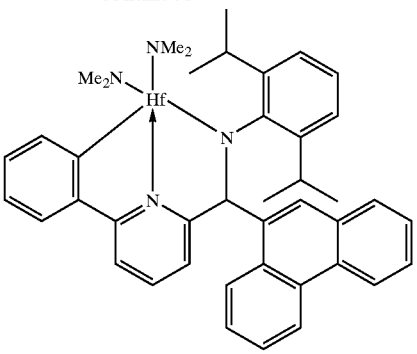

In addition, Lewis base adducts of the metal-ligand complexes in the above formulas are also suitable, for example, ethers, amines, thioethers, phosphines and the like are suitable as Lewis bases.

The metal-ligand complexes can be formed by techniques known to those of skill in the art, such as combinations of metal precursors and ligands under conditions to afford complexation. In some embodiments, $R^{14}$ is hydrogen and the metal-ligand complexes are formed by a metallation reaction (in situ or not) as shown below in scheme 3:

Scheme 3

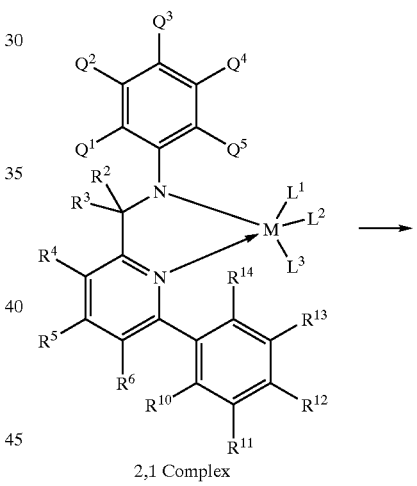

2,1 Complex

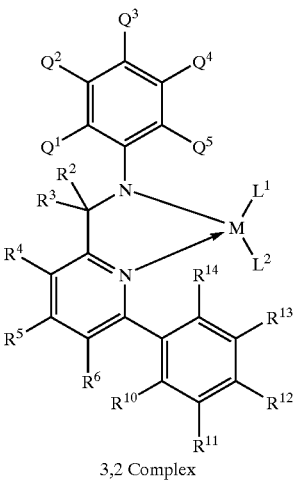

3,2 Complex

In scheme 3, $R^{14}$ is hydrogen (but see above for the full definition of $R^{14}$ in other embodiments of this invention). The metallation reaction to convert the 2,1 complex on the left to the 3,2 complex on the right can occur via a number of mechanisms, likely depending on the substituents chosen for $L^1$, $L^2$ and $L^3$ and the other substituents such as $Q^1$–$Q^5$, $R^2$–$R^6$, $R^{10}$ to $R^{13}$. In one embodiment, when $L^1$, $L^2$ and $L^3$ are each $N(CH_3)_2$, the reaction can proceed by heating the 2,1 complex to a temperature above about 100° C. In this embodiment, it is believed that $L^1$ and $L^2$ remain $N(CH_3)_2$ in the 3,2 complex. In another embodiment when $L^1$, $L^2$ and $L^3$ are each $N(CH_3)_2$, the reaction can proceed by adding a group 13 reagent (as described below) to the 2,1 complex at a suitable temperature (such as room temperature). Preferably the group 13 reagent for this purpose is di-isobutyl aluminum hydride, tri-isobutyl aluminum or trimethyl aluminum. In this embodiment, $L^1$ and $L^2$ are typically converted to the ligand (e.g., alkyl or hydride) stemming from the group 13 reagent (e.g., from trimethyl aluminum, $L^1$ and $L^2$ are each $CH_3$ in the 3,2 complex). The 2,1 complex in scheme 3 is formed by the methods discussed above.

In an alternative embodiment possibly outside the scope of scheme 3, for isotactic polypropylene production, it is currently preferred that $R^{14}$ is either hydrogen or methyl.

Various references disclose metal complexes that may appear to be similar; see for example, U.S. Pat. Nos. 6,103,657 and 5,637,660, both of which are incorporated herein by reference for all purposes. However, certain embodiments of the invention herein provide unexpectedly improved polymerization performance (e.g., higher activity and/or higher polymerization temperatures and/or higher comonomer incorporation) relative to the embodiments disclosed in those references. In particular, as shown in certain of the examples herein, the activity of the hafnium metal catalysts is far superior to that of the zirconium catalysts. Indeed, it also appears as if the zirconium metal centered catalysts have inferior performance with respect to incorporation of comonomer into an ethylene/comonomer type copolymer, especially for 1-octene, isobutylene and styrene comonomers.

The ligands, complexes or catalysts may be supported on an organic or inorganic support. Suitable supports include silicas, aluminas, clays, zeolites, magnesium chloride, polyethyleneglycols, polystyrenes, polyesters, polyamides, peptides and the like. Polymeric supports may be crosslinked or not. Similarly, the ligands, complexes or catalysts may be supported on similar supports known to those of skill in the art. In addition, the catalysts of this invention may be combined with other catalysts in a single reactor and/or employed in a series of reactors (parallel or serial) in order to form blends of polymer products.

Polymerization Activators/Additives

The metal-ligand complexes and compositions are active catalysts typically in combination with a suitable activator, combination of activators, activating technique or activating package, although some of the ligand-metal complexes may be active without an activator or activating technique. Broadly, the activator(s) may comprise alumoxanes, Lewis acids, Bronsted acids, compatible non-interfering activators and combinations of the foregoing. These types of activators have been taught for use with different compositions or metal complexes in the following references, which are hereby incorporated by reference in their entirety: U.S. Pat. Nos. 5,599,761, 5,616,664, 5,453,410, 5,153,157, 5,064,802, and EP-A-277,004. In particular, ionic or ion forming activators are preferred.

Suitable ion forming compounds useful as an activator in one embodiment of the present invention comprise a cation that is a Bronsted acid capable of donating a proton, and an inert, compatible, non-interfering, anion, $A^-$. Preferred anions are those containing a single coordination complex comprising a charge-bearing metal or metalloid core. Mechanistically, said anion should be sufficiently labile to be displaced by olefinic, diolefinic and unsaturated compounds or other neutral Lewis bases such as ethers or nitriles. Suitable metals include, but are not limited to, aluminum, gold and platinum. Suitable metalloids include, but are not limited to, boron, phosphorus, and silicon. Compounds containing anions that comprise coordination complexes containing a single metal or metalloid atom are, of course, well known and many, particularly such compounds containing a single boron atom in the anion portion, are available commercially.

Preferably such activators may be represented by the following general formula:

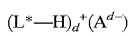

$(L^*—H)_d^+(A^{d-})$ wherein, $L^*$ is a neutral Lewis; $(L^*—H)^+$ is a Bronsted acid; $A^{d-}$ is a non-interfering, compatible anion having a charge of d–, and d is an integer from 1 to 3. More preferably $A^{d-}$ corresponds to the formula: $[M'^{3+}Q_h]^{d-}$ wherein h is an integer from 4 to 6; h–3=d; M' is an element selected from Group 13 of the Periodic Table of the Elements; and Q is independently selected from the group consisting of hydride, dialkylamido, halide, alkoxide, aryloxide, hydrocarbyl, and substituted-hydrocarbyl radicals (including halidesubstituted hydrocarbyl, such as perhalogenated hydrocarbyl radicals), said Q having up to 20 carbons. In a more preferred embodiment, d is one, i.e., the counter ion has a single negative charge and corresponds to the formula $A^-$.

Activators comprising boron or aluminum which are particularly useful in the preparation of catalysts of this invention may be represented by the following general formula:

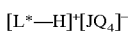

$[L^*—H]^+[JQ_4]^-$ wherein: $L^*$ is as previously defined; J is boron or aluminum; and Q is a fluorinated $C_{1-20}$ hydrocarbyl group. Most preferably, Q is independently selected from the group selected from the group consisting of fluorinated aryl group, especially, a pentafluorophenyl group (i.e., a $C_6F_5$ group) or a 3,5-bis($CF_3$)$_2C_6H_3$ group. Illustrative, but not limiting, examples of boron compounds which may be used as an activating cocatalyst in the preparation of the improved catalysts of this invention are tri-substituted ammonium salts such as: trimethylammonium tetraphenylborate, triethylammonium tetraphenylborate, tripropylammonium tetraphenylborate, tri(n-butyl)ammonium tetraphenylborate, tri(t-butyl)ammonium tetraphenylborate, N,N-dimethylanilinium tetraphenylborate, N,N-diethylanilinium tetraphenylborate, N,N-dimethylanilinium tetra-(3,5-bis (trifluoromethyl)phenyl)borate, N,N-dimethyl-(2,4,6-trimethylanilinium) tetraphenylborate, trimethylammonium tetrakis(pentafluorophenyl) borate, triethylammonium tetrakis(pentafluorophenyl) borate, tripropylammonium tetrakis(pentafluorophenyl) borate, tri(n-butyl)ammonium tetrakis(pentafluorophenyl) borate, tri(secbutyl)ammonium tetrakis(pentafluorophenyl) borate, N,N-dimethylanilinium tetrakis(pentafluorophenyl) borate, N,N-diethylanilinium tetrakis(pentafluorophenyl) borate, N,N-dimethyl-(2,4,6-trimethylanilinium) tetrakis(pentafluorophenyl) borate, trimethylammonium tetrakis-(2,3,4,6-tetrafluorophenylborate and N,N-dimethylanilinium tetrakis-(2,3,4,6-tetrafluorophenyl) borate; dialkyl ammonium salts such as:

di-(i-propyl)ammonium tetrakis(pentafluorophenyl) borate, and dicyclohexylammonium tetrakis(pentafluorophenyl) borate; and tri-substituted phosphonium salts such as: triphenylphosphonium tetrakis(pentafluorophenyl) borate, tri(o-tolyl)phosphonium tetrakis(pentafluorophenyl) borate, and tri(2,6-dimethylphenyl)phosphonium tetrakis(pentafluorophenyl) borate; and N,N-dimethylanilinium tetrakis(3,5-bis(trifluoromethyl)phenyl)borate. Preferred [L*—H]$^+$ cations are N,N-dimethylanilinium and tributylammonium. Preferred anions are tetrakis(3,5-bis(trifluoromethyl)phenyl)borate and tetrakis(pentafluorophenyl)borate. In some embodiments, the most preferred activator is PhNMe$_2$H+B(C$_6$F$_5$)$_4$$^-$.

Other suitable ion forming activators comprise a salt of a cationic oxidizing agent and a non-interfering, compatible anion represented by the formula:

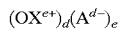

wherein: Ox$^{e+}$ is a cationic oxidizing agent having a charge of e+; e is an integer from 1to 3; and A$^{d-}$, and d are as previously defined. Examples of cationic oxidizing agents include: ferrocenium, hydrocarbyl-substituted ferrocenium, Ag$^+$, or Pb$^{+2}$. Preferred embodiments of A$^{d-}$ are those anions previously defined with respect to the Bronsted acid containing activating cocatalysts, especially tetrakis(pentafluorophenyl)borate.

Another suitable ion forming, activating cocatalyst comprises a compound that is a salt of a carbenium ion or silyl cation and a non-interfering, compatible anion represented by the formula:

wherein: ©$^+$ is a C$_{1-100}$ carbenium ion or silyl cation; and A$^-$ is as previously defined. A preferred carbenium ion is the trityl cation, i.e. triphenylcarbenium. The silyl cation may be characterized by the formula Z$^1$Z$^2$Z$^3$Si$^+$ cation, where each of Z$^1$, Z$^2$, and Z$^3$ is independently selected from the group consisting of alkyl, substituted alkyl, cycloalkyl, heterocycloalkyl, heterocyclic, aryl, substituted aryl, heteroaryl, substituted heteroaryl and combinations thereof. In some embodiments, a most preferred activator is Ph$_3$C$^+$ B(C$_6$F$_5$)$_4$$^-$.

Other suitable activating cocatalysts comprise a compound that is a salt, which is represented by the formula (A$^{*+a}$)$_b$(Z*J*$_j$)$^{-c}$$_d$ wherein A* is a cation of charge +a; Z* is an anion group of from 1to 50, preferably 1 to 30 atoms, not counting hydrogen atoms, further containing two or more Lewis base sites; J* independently each occurrence is a Lewis acid coordinated to at least one Lewis base site of Z*, and optionally two or more such J* groups may be joined together in a moiety having multiple Lewis acidic functionality; j is a number form 2 to 12; and a, b, c, and d are integers from 1to 3, with the proviso that a×b is equal to c×d. See, WO 99/42467, which is incorporated herein by reference. In other embodiments, the anion portion of these activating cocatalysts may be characterized by the formula ((C$_6$F$_5$)$_3$M''''—LN—M''''(C$_6$F$_5$)$_3$)$^-$ where M'''' is boron or aluminum and LN is a linking group, which is preferably selected from the group consisting of cyanide, azide, dicyanamide and imidazolide. The cation portion is preferably a quaternary amine. See, e.g., LaPointe, et al., *J. Am. Chem. Soc.* 2000, 122, 9560–956 1, which is incorporated herein by reference.

In addition, suitable activators include Lewis acids, such as those selected from the group consisting of tris(aryl) boranes, tris(substituted aryl)boranes, tris(aryl)alanes, tris (substituted aryl)alanes, including activators such as tris (pentafluorophenyl)borane.

Other useful ion forming Lewis acids include those having two or more Lewis acidic sites, such as those described in WO 99/06413 or Piers, et al. "New Bifunctional Perfluoroaryl Boranes: Synthesis and Reactivity of the ortho-Phenylene-Bridged Diboranes 1,2-[B(C$_6$F$_5$)$_2$]$_2$C$_6$X4(X=H, F)", *J. Am. Chem. Soc.*, 1999, 121, 3244–3245, both of which are incorporated herein by reference. Other useful Lewis acids will be evident to those of skill in the art. In general, the group of Lewis acid activators is within the group of ion forming activators (although exceptions to this general rule can be found) and the group tends to exclude the group 13 reagents listed below. Combinations of ion forming activators may be used.

Other general activators or compounds useful in a polymerization reaction may be used. These compounds may be activators in some contexts, but may also serve other functions in the polymerization system, such as alkylating a metal center or scavenging impurities. These compounds are within the general definition of "activator," but are not considered herein to be ion-forming activators. These compounds include a group 13 reagent that may be characterized by the formula G$^{13}$R'$_{3-p}$D$_p$ where G$^{13}$ is selected from the group consisting of B, Al, Ga, In and combinations thereof, p is 0, 1 or 2, each R' is independently selected from the group consisting of alkyl, substituted alkyl, cycloalkyl, heterocycloalkyl, heterocyclic and combinations thereof, and each D is independently selected from the group consisting of halide, hydride, alkoxy, aryloxy, amino, thio, phosphino and combinations thereof. In other embodiments, the group 13 activator is an oligomeric or polymeric alumoxane compound, such as methylalumoxane and the known modifications thereof. In other embodiments, a divalent metal reagent may be used that is defined by the general formula M'R'$_{2-p}$D$_p$ and p' is 0 or 1in this embodiment and R' and D are as defined above. M' is the metal and is selected from the group consisting of Mg, Ca, Sr, Ba, Zn, Cd and combinations thereof. In still other embodiments, an alkali metal reagent may be used that is defined by the general formula M''R' and in this embodiment R$^1$ is as defined above. M'' is the alkali metal and is selected from the group consisting of Li, Na, K, Rb, Cs and combinations thereof. Additionally, hydrogen and/or silanes may be used in the catalytic composition or added to the polymerization system. Silanes may be characterized by the formula SiR'$_{4-q}$D$_q$ where R' is defined as above, q is 1, 2, 3 or 4 and D is as defined above, with the proviso that there is at least one D that is a hydride.

The molar ratio of metal:activator (whether a composition or complex is employed as a catalyst) employed preferably ranges from 1:10,000 to 100:1, more preferably from 1:5000 to 10:1, most preferably from 1:10 to 1:1. In a preferred embodiment of the invention mixtures of the above compounds are used, particularly a combination of a group 13 reagent and an ion-forming activator. The molar ratio of group 13 reagent to ion-forming activator is preferably from 1:10,000 to 1000:1, more preferably from 1:5000 to 100:1, most preferably from 1:100 to 100:1. In a preferred embodiment, the ion forming activators are combined with a tri-alkyl aluminum, specifically trimethylaluminum, triethylaluminum, tri-n-octylaluminum, or triisobutylaluminum or with a di-alkyl aluminum hydride such as di-isobutyl aluminum hydride. A most preferred combination is about 1 equivalent of N,N-dimethylanilinium tetrakis (pentafluorophenyl) borate, and 5–30 equivalents of a Group 13 reagent. For ethylene-isobutylene copolymerization the group 13 reagent should be present in at least an amount that is 0.1 equivalents of the metal (e.g., the metal presecur compound) and preferably in an amount that is between 1 and 10 equivalents of the metal.

In other applications, the ligand will be mixed with a suitable metal precursor compound prior to or simultaneous with allowing the mixture to be contacted to the reactants. When the ligand is mixed with the metal precursor compound, a metal-ligand complex may be formed, which may be a catalyst. In connection with the metal-ligand complex and depending on the ligand or ligands chosen, the metal-ligand complex may take the form of dimers, trimers or higher orders thereof or there may be two or more metal atoms that are bridged by one or more ligands. Furthermore, two or more ligands may coordinate with a single metal atom. The exact nature of the metal-ligand complex(es) or compound(s) formed depends on the chemistry of the ligand and the method of combining the metal precursor and ligand, such that a distribution of metal-ligand complexes may form with the number of ligands bound to the metal being greater or less than the number of equivalents of ligands added relative to an equivalent of metal precursor.

Monomers/Polymers

The compositions, complexes and/or catalysts of this invention are particularly effective at polymerizing α-olefins (such as propylene, 1-butene, 1-pentene, 1-hexene, 1-heptene, 1-octene, and styrene), copolymerizing ethylene with α-olefins (such as propylene, 1-butene, 1-pentene, 1-hexene, 1-heptene, 1-octene, and styrene), and copolymerizing ethylene with 1,1-disubstituted olefins (such as isobutylene). These compositions might also polymerize monomers that have polar functionalities in homopolymerizations or copolymerizations and/or homopolymerize 1,1-disubstituted olefins. Also, diolefins in combination with ethylene and/or α-olefins or 1,1-disubstituted olefins may be copolymerized. The new catalyst compositions can be prepared by combining a metal precursor with a suitable ligand and, optionally, an activator or combination of activators.

In general monomers useful herein may be olefinically or unsaturated monomers having from 2 to 20 carbon atoms either alone or in combination. Generally, monomers may include olefins, diolefins and unsaturated monomers including ethylene and $C_3$ to $C_{20}$ □α-olefin such as propylene, 1-butene, 1-hexene, 1-octene, 4-methyl-1-pentene, 1-norbornene, styrene and mixtures thereof; additionally, 1,1-disubstituted olefins, such as isobutylene, 2-methyl-1-butene, 2-methyl-1-pentene, 2-ethyl-1-pentene, 2-methyl-1-hexene, 3-trimethylsilyl-2-methyl-1-propene, α-methylstyrene, either alone or with other monomers such as ethylene or $C_3$ to $C_{20}$ α-olefins and/or diolefins. The α-olefins listed above may be polymerized in a stereospecific manner e.g. to generate isotactic or syndiotactic or hemiisotactic polypropylene. Additionally the α-olefins may be polymerized to produce a polymer with differing tacticity sequences within the polymer chain, such as polypropylene containing atactic and isotactic sequences within the same polymer chain. These definitions are intended to include cyclic olefins. Diolefins generally comprise 1,3-dienes such as (butadiene), substituted 1,3-dienes (such as isoprene) and other substituted 1,3-dienes, with the term substituted referring to the same types of substituents referred to above in the definition section. Diolefins also comprises 1,5-dienes and other non-conjugated dienes. The styrene monomers may be unsubstituted or substituted at one or more positions on the aryl ring. The use of diolefins in this invention is typically in conjunction with another monomer that is not a diolefin. In some embodiments, acetylenically unsaturated monomers may be employed.

More specifically, it has been found that the catalysts of the present invention are particularly active for certain monomers, particularly α-olefins. Thus, the catalysts of the present invention may provide higher comonomer incorporation for copolymers of ethylene and co-monomers having three or more carbon atoms.

In addition, the catalysts of the present invention may polymerize vinyl chloride alone (e.g., in a homopolymerization) or with other monomers (such as ethylene or $C_3$ to $C_{20}$ α-olefins). Furthermore, vinyl monomers with functional groups may also be polymerized alone (e.g., in a homopolymerization) or with other monomers (such as ethylene or $C_3$ to $C_{20}$ α-olefins). Such functional group containing vinyl monomers can be characterized by the general formula $H_2C=CH-FG$, where FG is the functional group that contains at least one heteroatom (using the previous definition) or halogen (e.g., Cl, F, Br, etc.). Functional monomers include $C_1-C_{20}$ acrylates, $C_1-C_{20}$ methacrylates, $C_1-C_{20}$ vinylacetates, acrylic acid, methacrylic acid, maleic anhydride, vinyl acetate, vinyl ethers, acrylonitrile, acrylamide, vinyl chloride and mixtures thereof.

Novel polymers, copolymers or interpolymers may be formed having unique physical and/or melt flow properties. Such novel polymers can be employed alone or with other polymers in a blend to form products that may be molded, cast, extruded or spun. End uses for the polymers made with the catalysts of this invention include films for packaging, trash bags, bottles, containers, foams, coatings, insulating devices and household items. Also, such functionalized polymers are useful as solid supports for organometallic or chemical synthesis processes.

More specifically, the catalysts of this invention have prepared novel copolymers of ethylene and isobutylene. These novel polymers have high molecular weight combined with high incorporation of isobutylene. Others have broadly claimed such copolymers. See e.g., U.S. Pat. Nos. 5,866,665 and 5,763,556, which are both incorporated herein by reference. However, the combination of these properties has not been previously exemplified and is commercially promising. More specifically, the novel copolymers have a number average molecular weight of at least 50,000 and a weight percent incorporation of isobutylene of at least about 30 wt. %.

Also, it has been found that the catalytic performance at high temperature of particular catalysts of the present invention for the polymerization of olefins in general, including the co-polymerization of ethylene and α-olefins, is unexpectedly good. In particular, it has been found that varying the ligand substituents (R and Q groups) discussed herein allows one to increase the polymerization performance and polymer molecular weight for olefin polymerizations at high temperatures, particularly for polymerization temperatures above 120° C. In particular, when $R^3$ is aryl or substituted aryl, the high temperature polymerization catalytic performance is improved compared to when $R^3$ is hydrogen or alkyl. Also, the steric bulk of the $R^1$ and $R^7$ groups can affect polymeization performance. In particular, improved high temperature polymerization performance is observed when $Q^1$ and $Q^5$ are both not hydrogen.

It has been found that particular catalysts of the present invention co-polymerize ethylene and styrene (or substituted styrenes), forming ethylene-styrene copolymers. In particular, it has been found that varying the ligand substituents (R and Q groups) discussed herein allows one to vary the ratio of styrene to ethylene incorporated in the copolymer, and the ethylene-styrene copolymerization activity and Mw of the resulting ethylene-styrene copolymer. In particular, when $R^7$ is aryl or substituted aryl, the ratio of styrene to ethylene incorporated in the copolymer is significantly higher than when $R^7$ is hydrogen or alkyl. The higher level of styrene incorporation when $R^7$ is aryl or substituted aryl is unexpected.

The α-olefins listed above may be polymerized in a stereospecific manner e.g. to generate isotactic or syndiotactic or hemiisotactic poly-α-olefins. Additionally the α-olefins may be polymerized to produce a polymer with differing tacticity sequences within the polymer chain, such as polypropylene containing atactic and isotactic sequences within the same polymer chain. The stereoregularity may be interrupted by stereoerrors, in particular isolated stereoerrors have been observed, which is an indication of enantiomorphic side control. Also regioerrors might be present in the isotactic polypropylene polymer as it is described in the literature. In particular isolated 2-1 insertions may be observed. (see, e.g., Resconi et al., "Selectivity in Propene Polymerization with Metallocene Catalysts," Chem. Rev. 2000, 100, 1253–1345).

More specifically, it has been found that particular catalysts of the present invention polymerize propylene to isotactic or crystalline polypropylene, forming polymers with novel properties. This polymerization activity for isotactic polypropylene has surprising performance in a solution process. In particular, it has been found that varying the R and Q groups discussed herein allows one to vary the crystallinity index of the crystalline polypropylene formed. In general, reducing the steric bulk of the $R^1$ group results in a polymer having a lower crystallinity index, such that when $Q^1$ and $Q^5$ are both methyl, tacticity may be insufficient to provide a crystalline polymer. Also, the steric bulk of the $R^3$ and $R^7$ group can affect the crystallinity index.

The isotactic polypropylene polymers formed from these catalysts in a solution polymerization process have a crystallinity index of between about 0.35 and about 0.95, more specifically between about 0.65 and 0.95 and in some embodiments preferably above about 0.8, under the polymerization conditions employed. The crystallinity index is determined using FTIR as is known to those of skill in the art and calibrated based on a relative scale. In one embodiment, the crystallinity index value can be determined using commercially available FTIR equipment (such as a Bruker Equinox 55 with an IR Scope II in reflection mode using Pike MappIR software). The crystallinity index is obtained from the ratio of band heights at 995 $cm^{-1}$ and 972 $cm^{-1}$. Atactic polypropylene has a ratio of band heights or crystallinity index of 0.2. Greater than 98% isotactic polypropylene has a crystallinity index ratio of greater than 0.95. Generally, the amount of error in crystallinity index measurements is ±10.05. Polymer blends of various compositions show a linear relationship between % isotacticity and crystallinity index. See, for example, J. P. Luongo, *J. Appl. Polym. Sci.*, 3 (1960) 302–309 and T. Sundell, H. Fagerholm, H. Crozier, *Polymer* 37 (1996) 3227–3231, each of which is incorporated herein by reference.

As those of skill in the art will recognize, isotacticity can also be represented by percent pentads (%mmmm) as determined by $^{13}C$ NMR spectroscopy. Proton decoupled $^{13}C$ NMR spectroscopy can be performed using commercially available equipment (such as a Bruker 300 MHz at 100° C. probe temperature) to determine the degree of tacticity as %mmmm pentads (for assignment of $^{13}C$ signals see the review Brintzinger H. H. et al., *Angew. Chem. Int. Ed. Eng.* 1995, 34, 1143, which is incorporated herein by reference). For example, a 15–30 mg polymer sample is dissolved in a 1:1 mixture of $C_2D_2Cl_4$ and $C_2Cl_4$ by heating the sample to ca. 100° C. The %mmmm is determined by the ratio of peak integral from 23.5 to 21.5 ppm and peak integral 23.5 to 19 ppm. Proton decoupled $^{13}C$ NMR spectroscopy can be also performed to determine the frequency of and nature of stereoerrors and regioerrors.

In addition, the melting point of the crystalline polypropylene is generally in the range of from about 115° C. to about 160° C., more specifically between about 120° C. and 155° C., and in some embodiments preferably above about 135° C. Melting points are determined by differential scanning calorimetry, as is known in the art (see also the example section, herein). Surprisingly, the tacticity level and melting point are relatively level throughout different polymerization temperatures.

The weight average molecular weight of the crystalline polypropylene according to this application ranges from about 15,000 to about 4,500,000 and for some embodiments more specifically between about 50,000 to about 500,000 for the polymerization condition of a polymerization temperature at or above about 110° C. The polydispersity of the crystalline polypropylene of this invention ($M_w/M_n$) is generally about 2.5 or lower and in alternative embodiments is between about 2.0 and 3.5. Molecular weight and polydispersity index is determined according to method known to those of skill in the art, based, generally on polystyrene standards. As those of skill in the art will recognize, error in molecular weight measurements can range from 10–20%.

Novel polymers, copolymers or interpolymers may be formed having unique physical and/or melt flow properties. Polymers that can be prepared according to the present invention include propylene copolymers with at least one $C_4$–$C_{20}$ α-olefin, particularly 1-butene, 1-hexene, 4-methyl-1-pentene and 1-octene. The copolymers of propylene with at least one $C_4$–$C_{20}$ α-olefin comprise from about 0.1 wt. % higher olefin to about 60 wt. % higher olefin, more specifically from about 0.2 wt. % higher olefin to about 50 wt. % higher olefin and still more specifically from about 2 wt. % higher olefin to about 30 wt. % higher olefin. For certain embodiments of this invention, crystalline copolymers include those of propylene and a comonomer selected from the group consisting of ethylene, 1-butene, 1-hexene, and 1-octene comprise from about 0.2 to about 30 wt. % comonomer, more specifically from about 1 to about 20 wt. % comonomer, even more specifically from about 2 to about 15 wt. % comonomer and most specifically from about 5 to about 12 wt. % comonomer.

The novel polymers (such as isotactic polypropylene) disclosed herein can be employed alone or with other natural or synthetic polymers in a blend. Such other natural or synthetic polymers can be polyethylene (including linear low density polyethylene, low density polyethylene, high density polyethylene, etc.), atactic polypropylene, nylon, EPDM, ethylene-propylene elastomer copolymers, polystyrene (including syndiotactic polystryene), ethylene-styrene copolymers and terpolymers of ethylene-styrene and other $C_3$–$C_{20}$ olefins (such as propylene).

Melt flow rate (MRF) for polypropylene and copolymer of propylene and one or more $C_4$–$C_{20}$ α-olefins is measured according to ASTM D-1238, condition L (2.16 kg, 230° C.). In some embodiments of this invention, the MFR is in the range of 0.005–1,000, more specifically 0.01–500 and even more specifically 0.1–100. Flex modulus for polypropylene and copolymer of propylene and one or more $C_4$–$C_{20}$ α-olefins is measured according to ASTM D-790. In some embodiments of this invention, the flex modulus ranges from 20,000–400,000 psi, more specifically from 20,000–300,000 psi and even more specifically from 100,000–200,000 psi. Notch izod impact for polypropylene and copolymer of propylene and one or more $C_4$–$C_{20}$ α-olefins is measured according to ASTM D-256A. In some embodiments of this invention, the notch izod impact ranges from 0.1 to no break in ft-lbs/in.

The novel polypropylene and copolymer of propylene and one or more $C_4$–$C_{20}$ α-olefins disclosed in the present invention are useful for a wide variety of applications, including films (such as blown and cast film, clarity film and multi-layer films), thermoforming (such as cups, plates, trays and containers), injection moulding, blow-moulding, foams (such as structural foams), pipe (such as potable water pipe and high pressure pipe), automotive parts, and other applications that will be evident to those of skill in the art.

Melt strength (measured in cN) and melt drawability (measured in mm/s) tests are conducted by pulling ("taking-up") strands of the molten polymers or blends at constant acceleration until breakage occurs. An experimental set-up comprises a capillary rheometer and a Rheotens apparatus as a take-up device. The molten strands are drawn uniaxially to a set of accelerating nips located 100 mm below the die. The force required to uniaxially extend the strands is recorded as a function of the take-up velocity or the nip rolls. In the case of polymer melts exhibiting draw resonance (indicated by the onset of a periodic oscillation of increasing amplitude in the measured force profile), the maximum force and wheel velocity before the onset of draw resonance are taken as the melt strength and melt drawability, respectively. In the absence of draw resonance, the maximum force attained during testing is defined as the melt strength and the velocity at which breakage occurs is defined as the melt drawability. These tests are typically run under the following conditions:

| | |
|---|---|
| Mass flow rate | 1.35 grams/min |
| Temperature | 190° C. |
| Equilibration time at 190° C. | 10 minutes |
| Die | 20:1 (with entrance angle of approximately 45 degrees) |
| Capillary length | 41.9 mm |
| Capillary diameter | 2.1 mm |
| Piston diameter | 9.54 mm |
| Piston velocity | 0.423 mm/s |
| Shear rate | 33.0 s$^{-1}$ |
| Draw-down distance (die exit to take-up sheels) | 100 mm |
| Cooling conditions | Ambient air |
| Acceleration | 2.4 mm/s$^2$ |

For some aspects of the present invention the novel polymers are useful to produce foams having improved properties. For foams and other applications requiring melt strength, the MFR is typically in the range of 0.1–10, more specifically in the range of 0.3–3 and most specifically in the range of 0.5–2. The melt strength is typically greater than 5 cN, more specifically greater than 9 cN and most specifically greater than 12 cN.

The drawability is typically greater than 15 mm/sec, more specifically greater than 25 mm/sec and most specifically greater than 35 mm/sec.

In some aspects of the present invention, the novel polymers disclosed herein are useful for a wide variety of applications where certain optical properties are beneficial. Gloss is measured according to ASTM D-1746. Haze is measured according to ASTM D-1003 and clarity is measured according to ASTM D-2457. The novel polymers disclosed herein in some aspects are films having haze of less than 10%. In addition films having clarity of greater than 91% may be beneficially obtained.

Polymerization Systems

Polymerization can be carried out in the Ziegler-Natta or Kaminsky-Sinn methodology, including temperatures of from −100° C. to 300° C. and pressures from atmospheric to 3000 atmospheres. Suspension, solution, slurry, gas phase or high-pressure polymerization processes may be employed with the catalysts and compounds of this invention. Such processes can be run in a batch, semi-batch or continuous mode. Examples of such processes are well known in the art. A support for the catalyst may be employed, which may be inorganic (such as alumina, magnesium chloride or silica) or organic (such as a polymer or cross-linked polymer). Methods for the preparation of supported catalysts are known in the art. Slurry, suspension, gas phase and high-pressure processes as known to those skilled in the art may also be used with supported catalysts of the invention.

Other additives that are useful in a polymerization reaction may be employed, such as scavengers, promoters, modifiers and/or chain transfer agents, such as hydrogen, aluminum alkyls and/or silanes.

As discussed herein, catalytic performance can be determined a number of different ways, as those of skill in the art will appreciate. Catalytic performance can be determined by the yield of polymer obtained per mole of metal complex, which in some contexts may be considered to be activity. Table 3 (FIG. 3) and Table 4 (FIG. 4) display the results of ethylene-1-octene copolymerizations using ancillary ligands of the invention in combination with hafnium and zirconium precursors, respectively. In the case of zirconium, Table 4 illustrates that the yield of copolymer obtained from the experiments is the highest when the zirconium precursor $(Zr(CH_2C_6H_5)_4)$ is employed without the use of an ancillary ligand (Table 4 in FIG. 4; Cell A3: 369 mg). This illustrates that the presence of the ancillary ligand may not necessarily enhance the catalytic activity of the zirconium metal center. In the case of hafnium, the yields are unexpected high. In contrast to zirconium, the yield of copolymer obtained when the hafnium precursor $(Hf(CH_2C_6H_5)_4)$ is employed without the use of an ancillary ligand is very low (Table 3 in FIG. 3; Cell A3: 47 mg).

Another measure of catalyst polymerization performance is co-monomer incorporation. As is well known in the art, many ethylene copolymers are prepared using ethylene and at least one other monomer. These copolymers or higher order polymers in some applications require higher amounts of additional co-monomer(s) than have been practical with known catalysts. Since ethylene tends to be the most reactive monomer, obtaining higher co-monomer incorporations is a benefit that is examined for polymerization catalysts. Two useful co-monomers are 1-octene and styrene. This invention offers the possibility of higher incorporation of co-monomers such as 1-octene and styrene. As shown herein, the ethylene/l-octene copolymers obtained from the combination of ancillary ligands and zirconium precursors all possess lower weight % 1-octene values (<11 wt. %) (Table 4 in FIG. 4), than the weight % 1-octene values for the ethylene/1-octene copolymers obtained from the combination of ancillary ligands and hafnium precursors.

Figure 3:
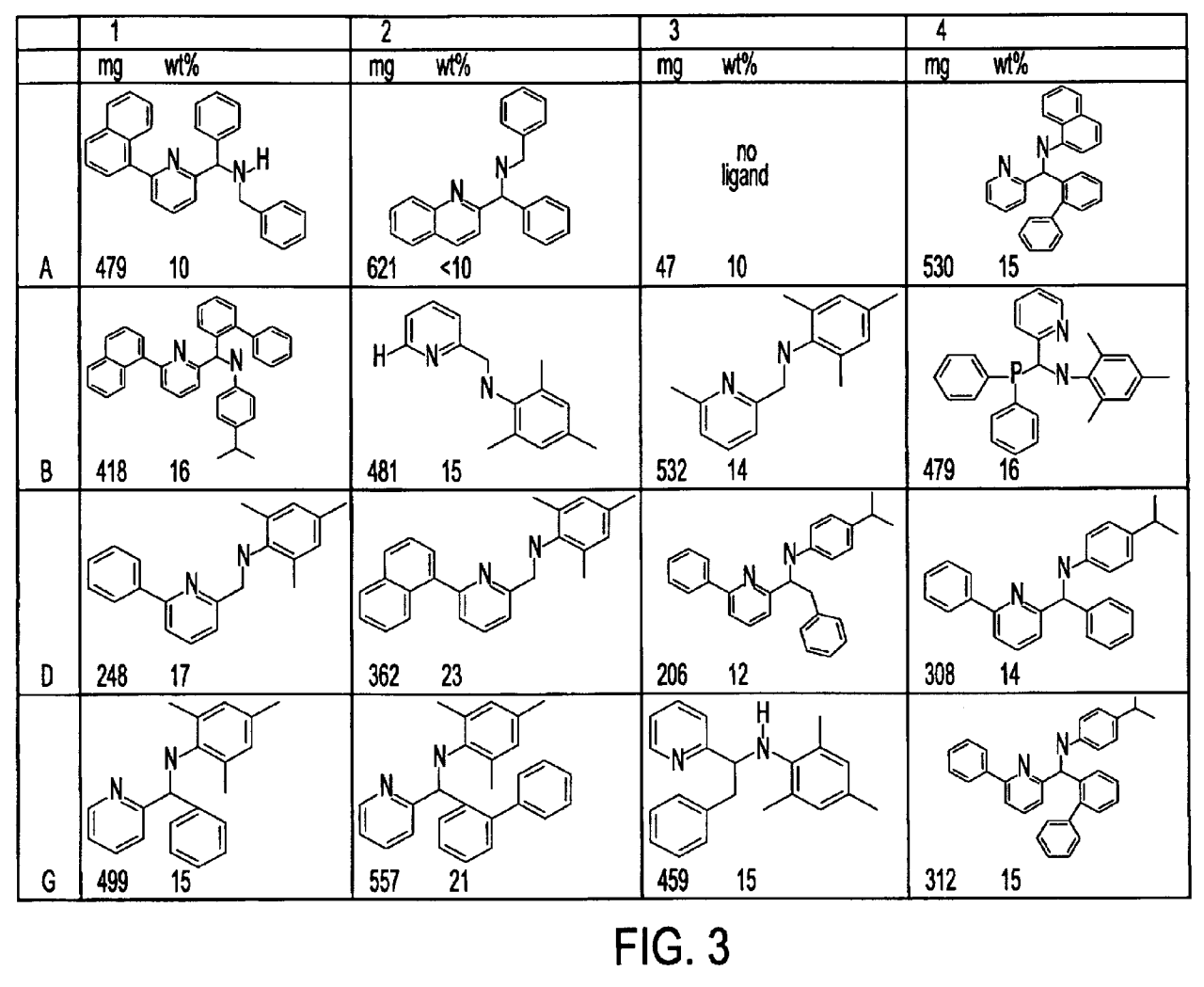

The results of the ethylene-1-octene copolymerizations using ancillary ligands of the invention in combination with a hafnium metal precursor are surprising (Table 3 in FIG. 3). In contrast to zirconium, the yield of copolymer obtained when the hafnium precursor $(Hf(CH_2C_6H_5)_4)$ is employed without the use of an ancillary ligand is very low (cell A3: 47 mg). Surprisingly, in the presence of certain ancillary ligands, the yields of copolymers obtained are enhanced dramatically relative to cell A3. In addition, the copolymers obtained typically possess higher wt. % 1-octene values relative to the values shown in Table 4. Additionally the wt. % 1-octene values for the copolymers obtained span a wider range (<10 wt. % to 23 wt. %). In contrast to Table 4, the results in Table 3 illustrate the ability of the ancillary ligand to tailor the catalytic performance of the hafnium metal center, both in terms of catalytic activity and the ability to incorporate 1-octene.

Tables 5 and 5a display the results of ethylene-styrene copolymerizations using ancillary ligands of the invention in combination with hafnium and zirconium precursors. The results in Tables 5 and 5 a illustrate that certain combinations of ancillary ligands with hafnium precursors are more productive in the copolymerization of ethylene with styrene than are combinations of the same ancillary ligands with zirconium precursors. Additionally the results illustrate combinations of ancillary ligands with hafnium precursors to produce copolymers with a higher styrene incorporation (wt % styrene by NMR in Table 5 and mol % styrene by FTIR in Table 5a) than the styrene incorporation in the products produced by the combinations of the same ancillary ligands with zirconium precursors.

As stated herein, a solution process is specified for certain benefits, with the solution process being run at a temperature above 90° C., more specifically at a temperature above 100° C., further more specifically at a temperature above 110° C. and even further more specifically at a temperature above 130° C. Suitable solvents for polymerization are non-coordinating, inert liquids. Examples include straight and branched-chain hydrocarbons such as isobutane, butane, pentane, isopentane, hexane, isohexane, heptane, octane, Isopar-E® and mixtures thereof, cyclic and alicyclic hydrocarbons such as cyclohexane, cycloheptane, methylcyclohexane, methylcycloheptane, and mixtures thereof, perhalogenated hydrocarbons such as perfluorinated $C_{4-10}$ alkanes, chlorobenzene, and aromatic and alkylsubstituted aromatic compounds such as benzene, toluene, mesitylene, and xylene. Suitable solvents also include liquid olefins which may act as monomers or comonomers including ethylene, propylene, 1-butene, butadiene, cyclopentene, 1-hexene, 1-pentene, 3-methyl-1-pentene, 4-methyl-1-pentene, 1,4-hexadiene, 1-octene, 1-decene, isobutylene, styrene, divinylbenzene, allylbenzene, and vinyltoluene (including all isomers alone or in admixture). Mixtures of the foregoing are also suitable.

In some embodiments, a solution process is specified for crystalline polypropylene production. The solution process to prepare isotactic polypropylene comprises adding a catalyst and propylene monomer to a reactor and subjecting the contents to polymerization conditions, such that polypropylene is obtained that has a crystallinity index value that does not vary by more than about 0.1, when the temperature of the solution process is varied from a temperature below 90° C. to a temperature above 100° C. In some embodiments in this section, the lower temperature is between about 70° C. and about 90° C. (or between about 75° C. and about 95° C. or between about 80° C. and about 95° C.) and the higher temperature is between about 100° C. and 110° C. (or between about 105° C. and about 115° C., or between about 100° C. and about 115° C.). In this context, the solution process can be run at a temperature and pressure that produce a desired product, but generally, the solution process temperature is above 100° C. and more specifically above 110° C., while maintaining a high crystallinity index value and high molecular weight. This solution polymerization process also maintains the melting point of the polypropylene, such that it does not vary by more than 10° C., when the temperature of the solution process is varied from a temperature below 90° C. to a temperature above 100° C. In this context, the solution process can be run at a temperature and pressure that produce a desired product, but generally, the solution process temperature is above 100° C. and more specifically above 110° C., while maintaining a melting point above 135° C. (and if desired below about 155° C.). Also, in this solution process, the process temperature may be at least 110° C. while producing polypropylene that has a weight average molecular weight of at least 100,000, more preferably at least about 300,000. In alternative embodiments the stated properties of the polymer are maintained when the temperature of the solution process is varied from a temperature below about 95° C. to a temperature above 105° C. or from a temperature below 85° C. to a temperature above 105° C. As with the above, these alternative embodiments have a lower temperature limit of about 70° C. and an upper temperature limit of about 115° C. The polypropylene properties are made in a process that does not require separation or fractionation of a product into component products (such as separation of atactic polypropylene from crystalline polypropylene, as is known in the art). Thus, in addition, the properties are measured on the bulk sample. Otherwise, the solution process may be run in accord with methods known to those of skill in the art.

Combinatorial Methodology

The ligands, metal-ligand complexes and compositions of this invention can be prepared and tested for catalytic activity in one or more of the above reactions in a combinatorial fashion. Combinatorial chemistry generally involves the parallel or rapid serial synthesis and/or screening or characterization of compounds and compositions of matter. U.S. Pat. Nos. 5,985,356, 6,030,917 and WO 98/03521, all of which are incorporated herein by reference, generally disclose combinatorial methods. In this regard, the ligands, metal-ligand complexes or compositions may be prepared and/or tested in rapid serial and/or parallel fashion, e.g., in an array format. When prepared in an array format, ligands, metal-ligand complexes or compositions may be take the form of an array comprising a plurality of compounds wherein each compound can be characterized by any of the above general formulas (i.e., I, A, II, III, IV, V, VI, VII, VIII, IX, X, XI, XII, XIII or XIV). An array of ligands may be synthesized using the procedures outlined previously. The array may also be of metal precursor compounds, the metal-ligand complexes or compositions characterized by the previously described formulae and/or description. Typically, each member of the array will have differences so that, for example, a ligand or activator or metal precursor or R group in a first region of the array may be different than the ligand or activator or metal precursor or R group in a second region of the array. Other variables may also differ from region to region in the array.

In such a combinatorial array, typically each of the plurality of compositions or complexes has a different composition or stoichiometry, and typically each composition or complex is at a selected region on a substrate such that each compound is isolated from the other compositions or complexes. This isolation can take many forms, typically depending on the substrate used. If a flat substrate is used, there may simply be sufficient space between regions so that there cannot be interdiffusion between compositions or complexes. As another example, the substrate can be a microtiter or similar plate having wells so that each composition or complex is in a region separated from other compounds in other regions by a physical barrier. The array may also comprise a parallel reactor or testing chamber.

The array typically comprises at least 8 compounds, complexes or compositions each having a different chemical formula, meaning that there must be at least one different atom or bond differentiating the members in the array or different ratios of the components referred to herein (with components referring to ligands, metal precursors, activators, group 13 reagents, solvents, monomers, supports, etc.). In other embodiments, there are at least 20 compounds, complexes or compositions on or in the substrate each having a different chemical formula. In still other embodiments, there are at least 40 or 90 or 124 compounds, complexes or compositions on or in the substrate each having a different chemical formula. Because of the manner of forming combinatorial arrays, it may be that each compound, complex or composition may not be worked-up, purified or isolated, and for example, may contain reaction by-products or impurities or unreacted starting materials.

The catalytic performance of the compounds, complexes or compositions of this invention can be tested in a combinatorial or high throughput fashion. Polymerizations can also be performed in a combinatorial fashion, see, e.g., U.S. patent application Ser. No. 09/239,223, filed Jan. 29, 1999; U.S. Pat. No. 6,306,658 and WO 00/09255, each of which is herein incorporated by reference.

EXAMPLES

General: All reactions were performed under a purified argon or nitrogen atmosphere in a Vacuum Atmospheres glove box. All solvents used were anhydrous, de-oxygenated and purified according to known techniques. All ligands and metal precursors were prepared according to procedures known to those of skill in the art, e.g., under inert athmosphere conditions, etc. Ethylene/styrene and ethylene/1-octene copolymerizations and propylene polymerizations were carried out in a parallel pressure reactor, which is fully described in pending U.S. patent applications Ser. No. 09/177,170, filed Oct. 22, 1998, Ser. No. 09/239,223, filed Jan. 29, 1999, and WO 00/09255, and U.S. Pat. No. 6,306,658 each of which is incorporated herein by reference.

High temperature Size Exclusion Chromatography was performed using an automated "Rapid GPC" system as described in U.S. Pat. Nos. 6,175,409, 6,260,407, and 6,294,388 each of which is incorporated herein by reference. In the current apparatus, a series of two 30 cm×7.5 mm linear columns, with one column containing PLgel 10 um, MixB and the other column containing PLgel 5 um, MixC (available from Polymer Labs). The GPC system was calibrated using narrow polystyrene standards. The system was operated at a eluent flow rate of 1.5 mL/min and an oven temperature of 160° C. o-dichlorobenzene was used as the eluent. The polymer samples were dissolved 1,2,4-trichlorobenzene at a concentration of about 1 mg/mL. Between 40 µL and 200 µL of a polymer solution were injected into the system. The concentration of the polymer in the eluent was monitored using an evaporative light scattering detector. All of the molecular weight results obtained are relative to linear polystyrene standards.

The ratio of 1-octene to ethylene incorporated in the ethylene-octene copolymer products was determined by FTIR. FTIR was performed on a Bruker Equinox 55+IR Scope II in reflection mode using a Pike MappIR accessory with 16 scans. The ratio of 1-octene to ethylene incorporation was represented as the weight % (wt. %) of 1-octene incorporated in the polymer (wt. % 1-octene). Wt. % 1-octene was obtained from ratio of band heights at 1378 $cm^{-1}$ and 4335 $cm^{-1}$. This method was calibrated using a set of ethylene/1-octene copolymers with a range of known wt. % 1-octene content.

Crystallinity in polypropylene was determined by FTIR spectroscopy. FTIR spectra of thin films deposited from solution onto gold coated Si wafers are acquired at 4 $cm^{-1}$ resolution and with 16 scans in reflection-absorption mode on a Bruker Equinox 55 FTIR spectrometer equipped with a Pike MappIR accessory. The height ratio of two bands at 995 $cm^{-1}$ (C—H bending and $CH_3$ rocking mode from regular crystalline isotactic helices) and 972 $cm^{-1}$ (coupled C—C stretching and $CH_3$ rocking mode, independent of crystallinity) is determined as a measure of isotacticity (as known in the art, see, e.g., J. P. Luongo, *J. Appl. Polym. Sci* 3 (1960) 302–309, and T. Sundell, H. Fagerholm, H. Crozier, *Polymer* 37 (1996) 3227–3231, each of which is incorporated herein by reference). For blends of atactic and isotactic polypropylene (PP) with 0–70% isotactic PP, the IR ratio is proportional to the percentage of isotactic PP. For greater than 98% isotactic PP the ratio is greater than 0.95, for amorphous PP the ratio is 0.2.

The ratio of styrene to ethylene incorporated in the polymer products, represented as the mol % of styrene incorporated in the polymer (mol % styrene) was determined using FTIR spectroscopy. The IR spectra (16 scans at 4 $cm^{-1}$ resolution) analyzed by Partial Least Squares (PLS) analysis with PLSplus/IQ V3.04 for GRAMS/32 (Galactic Industries) software, using the following training set for calibration.

Training Set

The analysis based on a training set consisting of 180 spectra of blends of ethylene-styrene copolymers with known styrene incorporation, and atactic homo-polystyrene. The 16 known copolymers had between 1 and 47 mol % incorporated styrene. The atactic homo-polystyrene content in the blends ranged from 0 to 90% of the total styrene content of the blend. Most blends are prepared from copolymers with up to 20 mol % incorporation. Multiple spectra per blend were included in the training set.

Preprocessing of the Spectra

Mean centering; linear baseline correction based on average absorbances at 2074 $cm^{-1}$–2218 $cm^{-1}$ and 3224 $cm^{-1}$–3465 $cm^{-1}$; thickness correction based on band area from 1483 $cm^{-1}$ to 1504 $cm^{-1}$ with baseline from 1389 $cm^{-1}$–1413 $cm^{-1}$ to 1518 $cm^{-1}$–1527 $cm^{-1}$.

Analysis

PLS-1 algorithm; spectral regions 499 $cm^{-1}$ to 2033 $cm^{-1}$ and 3577 $cm^{-1}$ to 4495 $cm^{-1}$. Prediction of number ratios of atactic homo-polystyrene to total styrene ($\propto$ % atactic homo-polystyrene to total styrene) with 10 factors and ethylene to total styrene ($\propto$ mol % total styrene) with 7 factors and calculation of mol % incorporated styrene from these 2 numbers.

The ratio of styrene to ethylene incorporated in the polymer products, represented as the weight % (wt. %) of styrene incorporated in the polymer (wt. % styrene) can also be determined using $^1$H NMR spectroscopy.

Differential Scanning Calorimetry (DSC) measurements were performed on a TA instrument DSC 2920 to determine the melting point of polymers. The sample was equilibrated at 200° and held for 4 minutes. The sample was cooled with a rate of 10° C. per minute to 55° C. where it was held for 10 minutes. The sample was cooled further to –50° C. with a rate of 10° C./min and held at –50° C. for 4 minutes. Then, the sample was heated to 200° C. at a rate of 1° C./min and data were collected during that heating period.

Ethylene/isobutylene copolymerizations were carried out in a parallel pressure reactor equipped with a magnetic stirrer hotplate. The ratio of isobutylene to ethylene incorporated in the polymer products, represented as the weight % (wt. %) of isobutylene incorporated in the polymer (wt. % IB) was determined using $^1$H NMR spectroscopy.
The following ligands are used in some of these examples:
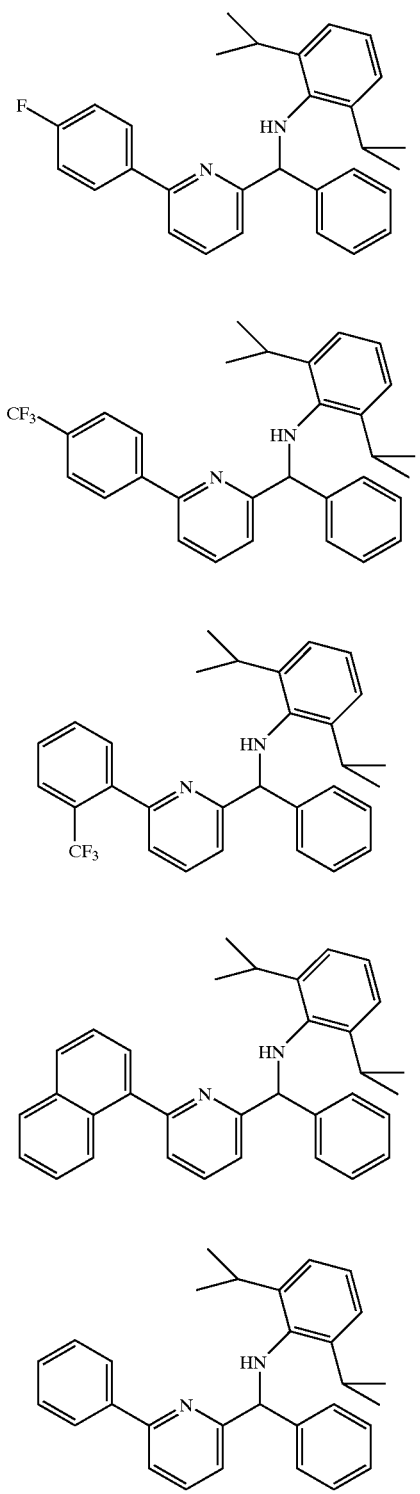
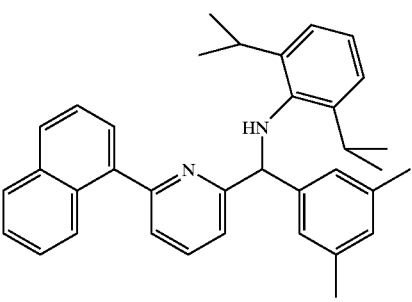
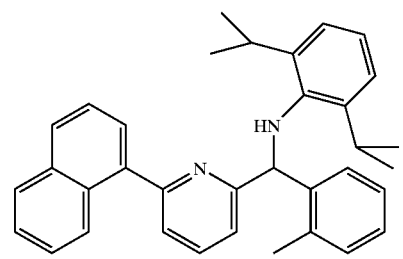
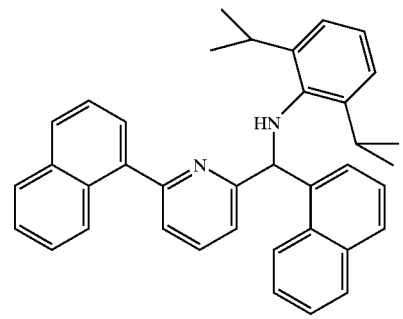
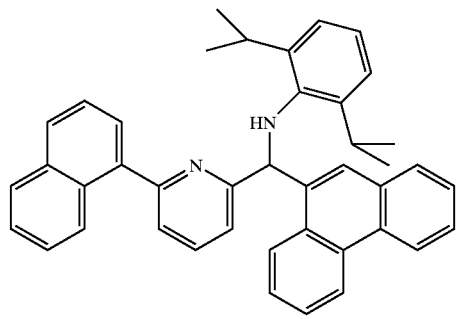
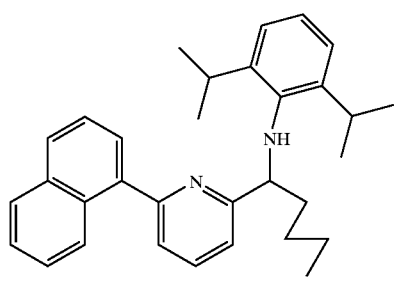

L11
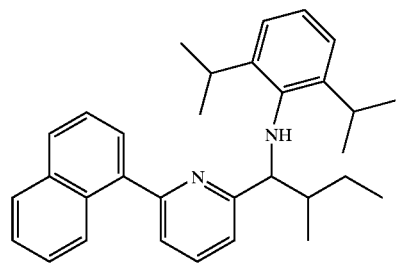
L12
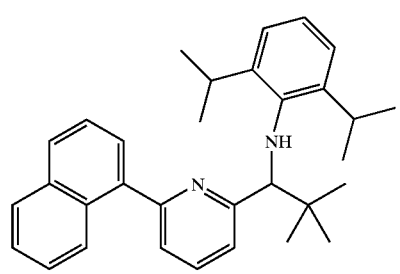
L13
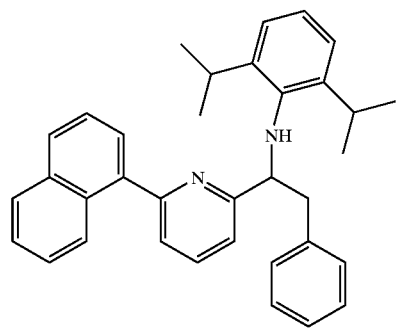
L14
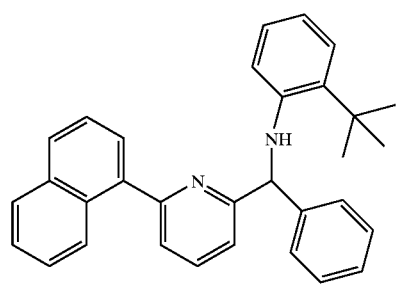
L15
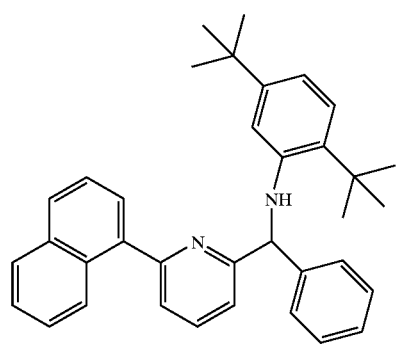
L16
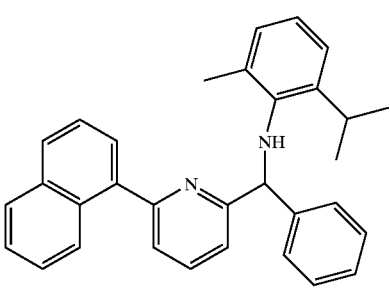
L17
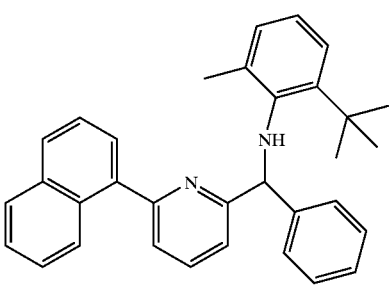
L18
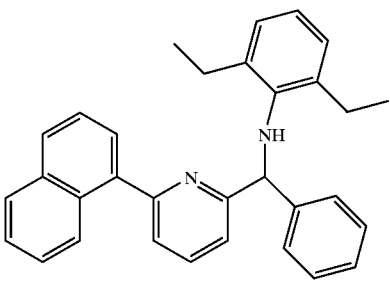
L19
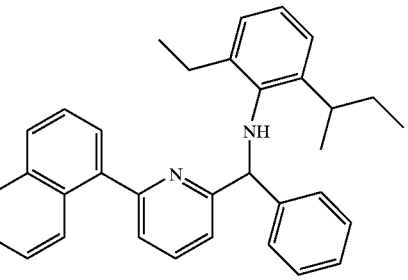
L20
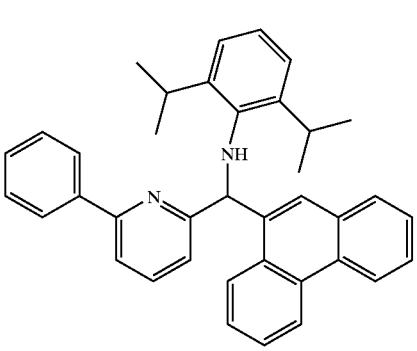

L21
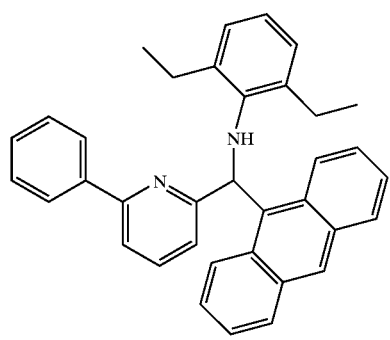
L22
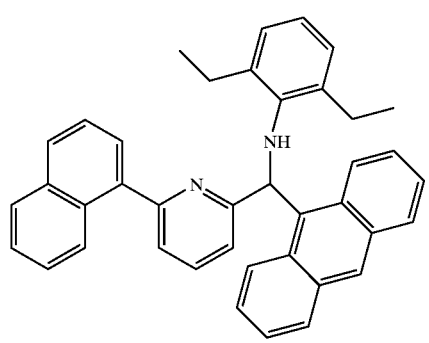
L23
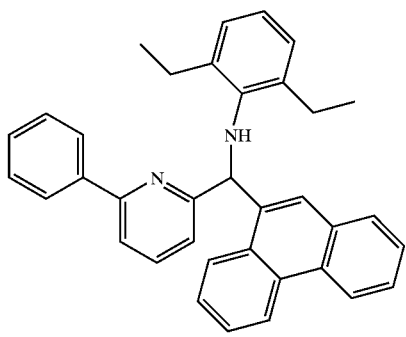
L24
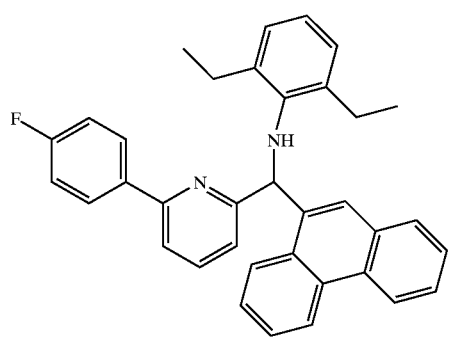
L25
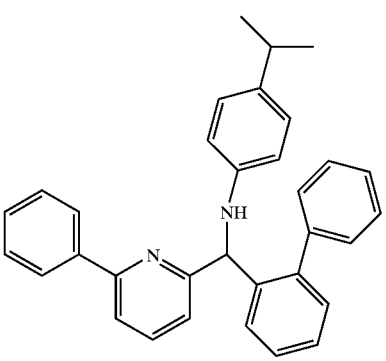
L26
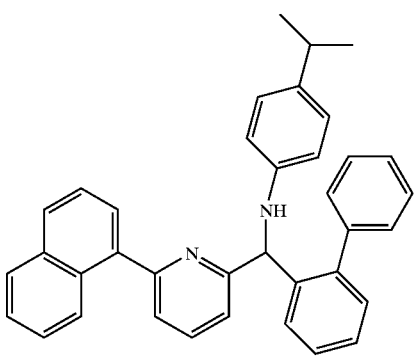
L27
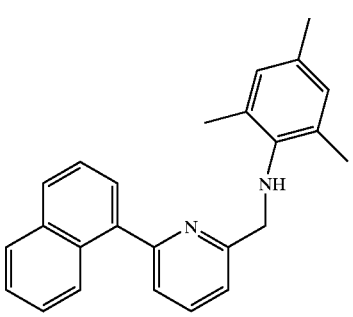
L28

93

-continued

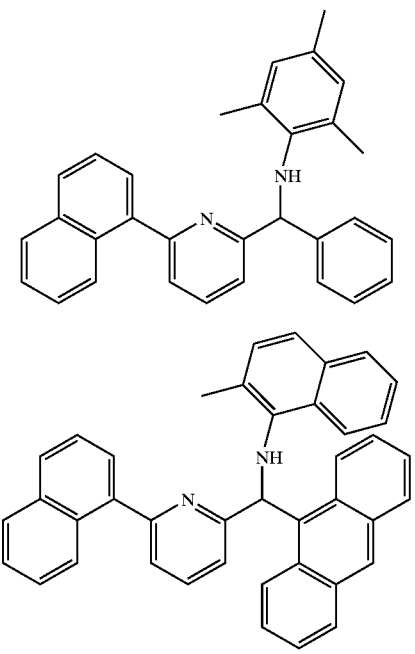

L29

L30

These ligands were prepared using techniques known to those of skill in the art, for example, using the following general experimental:

Part A: Synthesis of 2-bromo-6-formylpyridine

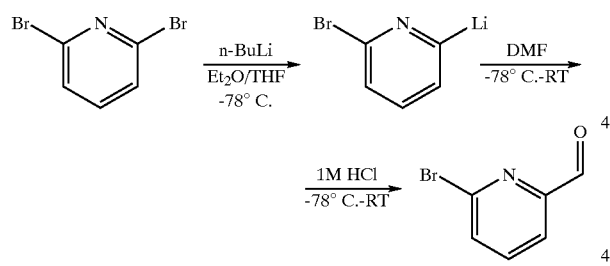

To a solution of 23.7 g (100 mmol) of 2,6-dibromopyridine in 150 mL of anhydrous, degassed THF cooled to −78° C. was added dropwise under $N_2$ a solution of 11.0 mL (110 mmol) of 10.0 M "BuLi in 150 mL of anhydrous, degassed $Et_2O$. After 2 h at −78° C., 24.2 mL (300 mmol) of anhydrous, degassed DMF was added dropwise with rapid stirring. This solution was stirred at −78° C. for 2 h, then allowed to warm to RT overnight.

The solution was cooled to −78° C. and 100 mL of 1.0 M aq. HCl was added slowly. The organic phase was separated and the aqueous phase was washed with 3×50 mL $Et_2O$. The organic washes were combined and washed with 3×50 mL $H_2O$ and 3×50 mL brine, then dried over $Na_2SO_4$. The volatiles were removed in vacuo to provide an orange oil. The oil was triturated with hexanes to give a pale orange solid that was washed with cold pentane and dried under vacuum overnight.

94

Part B: Synthesis of 2-formyl-6-naphthylpyridine

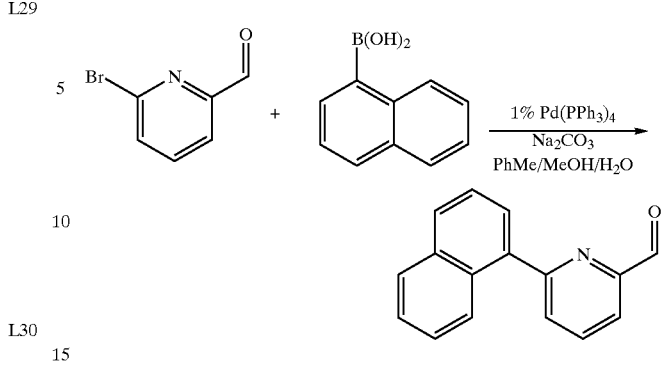

Naphthylboronic acid (2.06 g, 12 mmol) and $Na_2CO_3$ (2.65 g, 25 mmol) were dissolved in 60 mL of degassed 4:1 $H_2O$/MeOH. This solution was added via cannula to a solution of 1.86 g (10 mmol) of 2-bromo-6-formylpyridine and 116 mg (0.10 mmol) of $Pd(PPh_3)_4$ in 50 mL of degassed toluene. The biphasic solution was vigorously stirred and heated to 70° C. under $N_2$ for 4 h. On cooling to RT, the organic phase was separated and washed with 3×25 mL of $Et_2O$. The combined organic extracts were washed with 3×25 mL of $H_2O$ and 1×20 mL of brine and dried over $Na_2SO_4$. After removing the volatiles in vacuo, the resultant brown oil was chromatographed on silica with 0–50% hexanes/$CH_2Cl_2$. The early fractions contained naphthalene and binaphthyl and were discarded. The remaining fractions were combined and the volatiles were removed to provide 2-formyl-6-naphthlypyridine as a white solid.

Part C: Synthesis of 6-naphthylpyridine-2-(2,6-diisopropylphenyl)imine

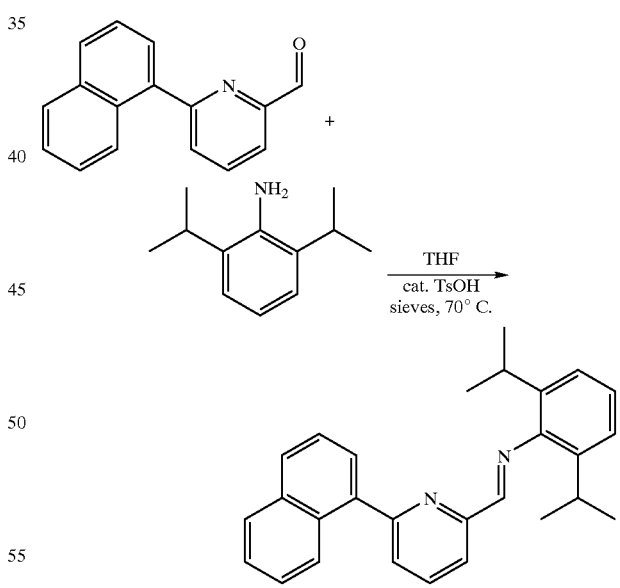

A solution of 1.17 g (0.5 mmol) of 2-formyl-6-naphtlypyridine and 0.98 g (0.55 mmol) of 2,6-diisopropylaniline in 50 mL of anhydrous THF containing 3 Å sieves and a catalytic amount of TsOH was heated to reflux under $N_2$ for 12 h. After filtration and removal of the volitiles in vacuo, the crude material was passed through a 4×6 cm plug of neutral alumina with 1:1 hexanes/$CH_2Cl_2$ eluent. Removal of the volitiles provided 6-naphthylpyridine-2-(2,6-diisopropylphenyl)imine as yellow crystals.

Part D: Synthesis of (6-naphthyl-2-pyridyl)-N-(2,6-diisopropylphenyl)benzylamine (Ligand L4)

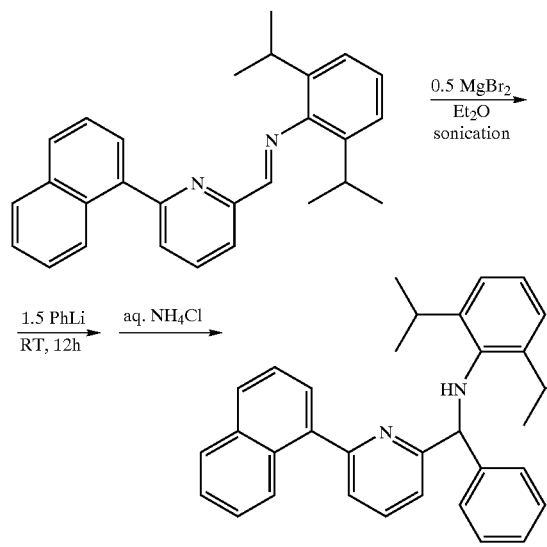

Synthesis with MgBr₂ Precomplexation

To a well-stirred slurry of powdered MgBr₂ (184 mg, 1 mmol) in 2 mL of anhydrous, degassed Et₂O was added under N₂ a solution of 6-naphthylpyridine-2-(2,6-diisopropylphenyl)imine (392 mg, 1 mmol) in 2 mL of Et₂O. The mixture was sonicated until the yellow color of the imine dissipated and a free-flowing pale yellow powder was formed. To this suspension was added with vigorous stirring a solution of phenyllithium (833 uL of 1.8 M in cyclohexane, 1.5 mmol). After stirring at RT for 12 h, the reaction was quenched with aq. NH₄Cl. The organic layer was separated, washed with brine and H₂O, then dried over Na₂SO₄. Following chromatography (silica gel, 3% THF/hexanes), the product was isolated as a colorless oil.

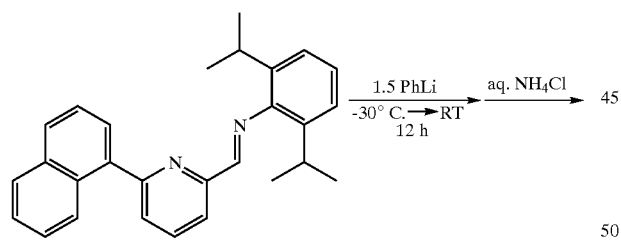

Synthesis without MgBr₂ Precomplexation

To a solution of 6-naphthylpyridine-2-(2,6-diisopropylphenyl)imine (392 mg, 1 mmol) in 5 mL of anhydrous, degassed Et₂O cooled to −30° C. under N₂ was added a solution of phenyllithium (833 uL of 1.8 M in cyclohexane, 1.5 mmol). After warming to RT over 1 h. the soln. was stirred at RT for 12 h. The reaction was then quenched with aq. NH₄Cl, and worked-up as above.

This same procedure is followed for the different ligands, but with the following different starting materials for the different ligands:

In part B:

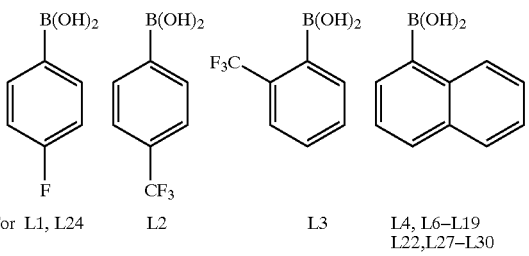

In Part C:

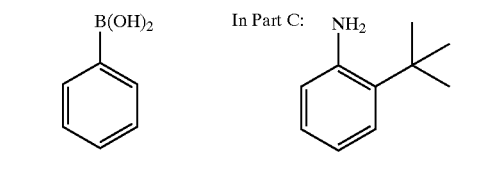

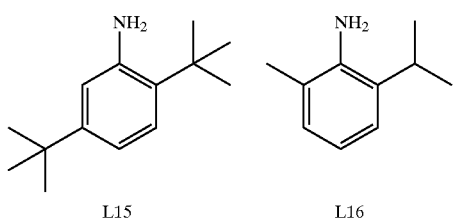

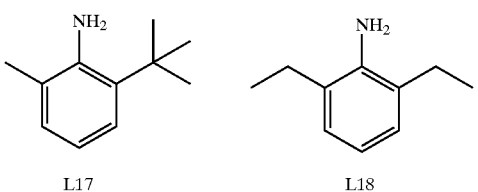

In part D:

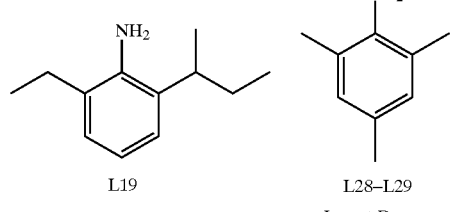

-continued

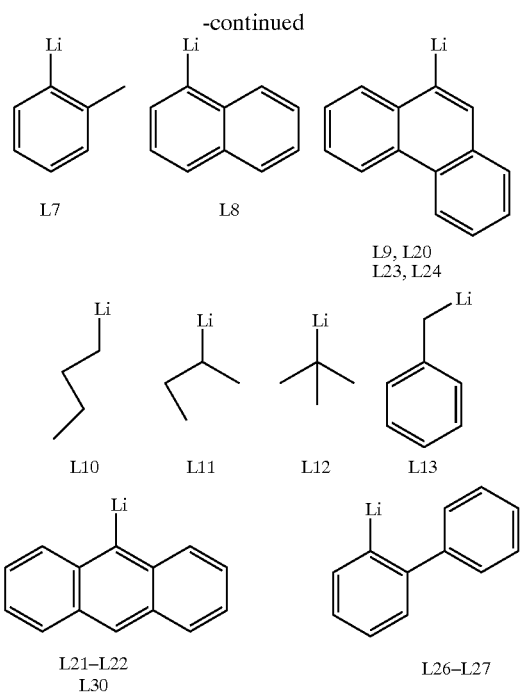

For ligand L28, the last step in the reaction sequence (part D) is a reduction reaction using sodiumtriacetozyborohydride (Na(Oac)$_3$BH) in THF for 1–3 days following aq. NH$_4$Cl quench and work-up as it is described in Part D above.

Example 1

Synthesis of Ligand

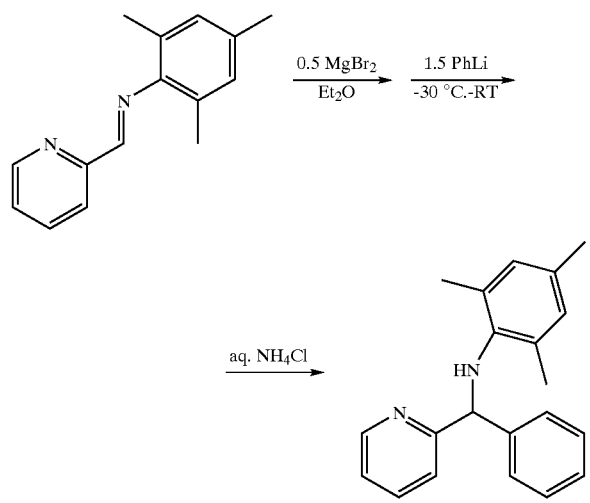

Both Parts to this Example Make the Same Ligand, Shown Above, With and Without the Presence of Complexing Agent.

Part A: Synthesis without MgBr$_2$ Complexation

To a solution of 2-pyridyl-N-mesitylimine (224 mg, 1 mmol) in 5 mL of anhydrous, degassed Et$_2$O cooled to −30° C.,□was□added□under□argon□a□solution□of□ phenyllithium (833 μL of 1.8 M in cyclohexane, 1.5 mmol). After warming to room temperature over 1 hour, the solution was stirred for a further 12 hours. The reaction was then quenched with aqueous NH$_4$Cl, the layers were separated, and the organic layer was dried over Na$_2$SO$_4$. GC-MS analysis showed a mixture of the C- and N-alkylated products. The C- to N-alkylation ratio was 4:1 as determined by $^1$H NMR.

Part B: Synthesis with MgBr$_2$ Complexation

To a stirred slurry of powdered MgBr$_2$ (92 mg, 0.5 mmol) in 1 mL of anhydrous, degassed Et$_2$O was added under argon a solution of 2-pyridyl-N-mesitylimine (224 mg, 1 mmol) in 5 mL of Et$_2$O. The mixture was stirred for 2 hours until the yellow color of the imine dissipated and a pale yellow solid was formed. After cooling to −30° C.,□a□solution□ of phenyllithium (833 μL of 1.8 M in cyclohexane, 1.5 mmol) was added with stirring. After warming to room temperature over 1 hour, the solution was stirred for a further 12 hours. The reaction was worked up as above. GC-MS analysis showed exclusive formation of the C-alkylated product. Following chromatography (silica, 10% ethyl acetate/hexanes), the product was isolated as a colorless solid (266 mg, 88%).

Examples 2–3

Preparation of the polymerization reactor prior to injection of catalyst composition; Ethylene-1-octene Polymerizations: A pre-weighed glass vial insert and disposable stirring paddle were fitted to each reaction vessel of the reactor. The reactor was then closed, 0.100 mL of a 0.02 M solution of triisobutylaluminium (TIBA) in toluene, then 2.375 mL of toluene, then 0.250 mL of 1-octene, then 2.375 mL of toluene, were injected into each pressure reaction vessel through a valve. The temperature was then set to 130° C., and the toluene/1-octene mixture was exposed to ethylene gas at 100 psi pressure. An ethylene pressure of 100 psi in the pressure cell and the temperature setting were maintained, using computer control, until the end of the polymerization experiment.

Preparation of the polymerization reactor prior to injection of catalyst composition; Ethylene-Styrene Polymerizations: A pre-weighed glass vial insert and disposable stirring paddle were fitted to each reaction vessel of the reactor. The reactor was then closed, 0.100 mL of a 0.02 M solution of triisobutylaluminium (TIBA) in toluene, then 4.50 mL of toluene, were injected into each pressure reaction vessel through a valve. The temperature was then set to 110° C., and the toluene mixture was exposed to ethylene gas at 100 psi pressure. An ethylene pressure of 100 psi in the pressure cell and the temperature setting were maintained, using computer control, until the end of the polymerization experiment.

Ethylene-1-octene and Ethylene-Styrene Polymerizations: The polymerization reactions were allowed to continue for 30 minutes, during which time the temperature and pressure were maintained at their pre-set levels by computer control. After 30 minutes, the ethylene flow to the reactor vessel was stopped. The temperature was then allowed to drop to below 80° C. and the ethylene pressure in the cell was vented.

Product work up: Ethylene-1-octene Polymerizations After the polymerization reaction, the glass vial insert, containing the polymer product and solvent, was removed from the pressure cell and removed from the inert atmosphere dry box, and the volatile components were removed using a centrifuge vacuum evaporator. After most of the volatile components had evaporated, the vial contents were dried thoroughly by evaporation at elevated temperature under reduced pressure. The vial was then weighed to determine the yield of polymer product. The polymer product was then analyzed by rapid GPC, as described above to determine the molecular weight of the polymer produced, and by FTIR spectroscopy to determine the ratio of 1-octene to ethylene incorporated in the polymer product, represented as the weight % of 1-octene incorporated in the polymer.

Product work up: Ethylene-Styrene Polymerizations After the polymerization reaction, the glass vial insert, containing the polymer product and solvent, was removed from the pressure cell and removed from the inert atmosphere dry box, and the volatile components were removed using a centrifuge vacuum evaporator. After most of the volatile components had evaporated, the vial contents were dried thoroughly by evaporation at elevated temperature under reduced pressure. The vial was then weighed to determine the yield of polymer product. The polymer product was then analyzed by rapid GPC, as described above to determine the molecular weight of the polymer produced, and by $^1$H NMR spectroscopy to determine the ratio of styrene to ethylene incorporated in the polymer product, represented as the weight % of styrene incorporated in the copolymer.

Presentation of results: Tables 3–5 present results from libraries of polymerizations, using the following key (Tables 3 and 4 are in FIGS. 3 and 4, respectively):

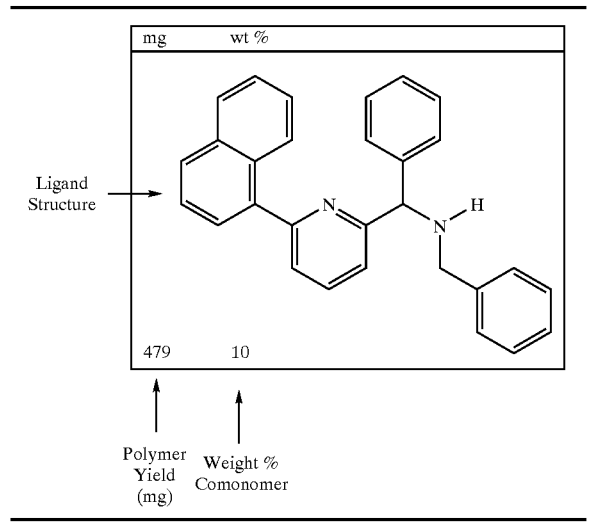

Example 2

Ethylene-1-octene Polymerizations Using Hafnium-Ligand Compositions

Preparation of Stock Solutions: The "group 13 reagent solution" is a 0.20 M solution of triisobutylaluminium (TIBA). The "activator solution" is a 10 mM solution of N,N'-dimethylanilinium tetrakis(pentafluorophenyl)borate in toluene (160 mg in 20 mL toluene), heated to approximately 85° C. to fully dissolve the N,N'-dimethylanilinium tetrakis(pentafluorophenyl)borate.

In situ preparation of Hafnium-ligand compositions: Stock solutions were prepared as follows: The "metal precursor solution" is a 25 mM solution of Hf(CH$_2$C$_6$H$_5$)$_4$ in toluene (34 mg in 2.50 mL toluene; HfCl$_4$ was purchased from Strem Chemicals, Inc., Newburyport, Mass. (99.95%+ Hf) and modified with 4 equivalents of benzyl Gringard at −30° C. in ether). The "ligand solutions" are a 25 mM solution the respective ligands in toluene, prepared in an array of 1 mL glass vials by adding 0.060 mL of toluene to 1.5 μmol of the ligand in a 1 mL glass vial. To each 1 mL glass vial containing ligand/toluene solution was added 0.060 mL of the metal precursor solution (1.5 μmol), to form the metal-ligand combination solution. To each metal-ligand combination solution was then added 0.060 mL of a 0.5 M 1-octene solution in toluene (30 μmol of 1-octene). The resultant solutions we allowed to sit at room temperature for 1 hour prior to addition of TIBA solution and injection into the reactor, as described below. Table 3 illustrates the hafnium-ligand solutions prepared in this example.

Injection of solutions into the pressure reactor vessel: After the toluene/1-octene mixture was saturated with ethylene at 100 psi pressure, 0.075 mL (15 μmol) of the group 13 reagent solution was added to the 1 mL vial. About 30 seconds later, 0.100 mL (1.0 μmol) of the "activator solution" followed immediately by 0.400 mL of toluene, were injected into the reaction vessel. About another 30 seconds later, 0.170 mL of the 1 mL vial contents, followed immediately by 0.330 mL of toluene, were injected into the reaction vessel. Results are presented in Table 3, which is presented in FIG. 3.

Comparative Example

Ethylene-1-octene Polymerizations Using Zirconium-Ligand Compositions

Preparation of Stock Solutions: The "group 13 reagent solution" is a 0.20 M solution of triisobutylaluminium (TIBA). The "activator solution" is a 10 mM solution of N,N'-dimethylanilinium tetrakis(pentafluorophenyl)borate in toluene (160 mg in 20 mL toluene), heated to approximately 85° C. to fully dissolve the N,N'-dimethylanilinium tetrakis(pentafluorophenyl)borate.

In situ preparation of Zirconium-ligand compositions: Stock solutions were prepared as follows: The "metal precursor solution" is a 25 mM solution of Zr(CH$_2$C$_6$H$_5$)$_4$ in toluene (28.5 mg in 2.50 mL toluene). The "ligand solutions" are a 25 mM solution the respective ligands in toluene, prepared in an array of 1 mL glass vials by adding 0.060 mL of toluene to 1.5 μmol of the ligand in a 1 mL glass vial. To each 1 mL glass vial containing ligand/toluene solution was added 0.060 mL of the metal precursor solution (1.5 μmol), to form the metal-ligand combination solution. To each metal-ligand combination solution was then added 0.060 mL of a 0.5 M 1-octene solution in toluene (30 μmol of 1-octene). The resultant solutions were allowed to sit at room temperature for 1 hour prior to addition of TIBA solution and injection into the reactor, as described below. Table 4 illustrates the zirconium-ligand solutions prepared in this comparative example.

Injection of solutions into the pressure reactor vessel: After the toluene/1-octene mixture was saturated with ethylene at 100 psi pressure, 0.075 mL (15 μmol) of the group 13 reagent solution was added to the 1 mL vial. About 30 seconds later, 0.100 mL (1.0 μmol) of the "activator solution" followed immediately by 0.400 mL of toluene, were injected into the reaction vessel. About another 30 seconds later, 0.170 mL of the 1 mL vial contents, followed immediately by 0.330 mL of toluene, were injected into the reaction vessel. Results are presented in Table 4, which is presented in FIG. 4.

Example 3

Ethylene-Styrene Polymerizations Using Hafnium-Ligand Compositions

Preparation of Stock Solutions: The "group 13 reagent solution" is a 0.20 M solution of triisobutylaluminium (TIBA). The "activator solution" is a 10 mM solution of N,N'-dimethylanilinium tetrakis(pentafluorophenyl)borate in toluene (160 mg in 20 mL toluene), heated to approximately 85° C. to fully dissolve the N,N'-dimethylanilinium tetrakis(pentafluorophenyl)borate.

In situ preparation of Hafnium-ligand compositions: Stock solutions were prepared as follows: The "metal precursor solution" is a 25 mM solution of $Hf(CH_2C_6H_5)_4$ in toluene (34 mg in 2.50 mL toluene; $HfCl_4$ was purchased from Strem Chemicals, Inc., Newburyport, Mass. (99.95%+ Hf) and modified with 4 equivalents of benzyl Gringard at −30° C. in ether). The "ligand solutions" are a 25 mM solution the respective ligands in toluene, prepared in an array of 1 mL glass vials by adding 0.060 mL of toluene to 1.5 μmol of the ligand in a 1 mL glass vial. To each 1 mL glass vial containing ligand/toluene solution was added 0.060 mL of the metal precursor solution (1.5 μmol), to form the metal-ligand combination solution. To each metal-ligand combination solution was then added 0.060 mL of a 0.5 M 1-octene solution in toluene (30 μmol of 1-octene). The resultant solutions were allowed to sit at room temperature for 1 hour prior to addition of TIBA solution and injection into the reactor, as described below. Table 5 illustrates the hafnium-ligand solutions prepared.

Injection of solutions into the pressure reactor vessel: After the toluene mixture was saturated with ethylene at 100 psi pressure, 0.500 mL of styrene followed immediately by 0.500 mL of toluene, were injected into the pressure reaction vessel. About 30 seconds later, 0.075 mL (15 μmol) of the group 13 reagent solution was added to the 1 mL vial. About another 30 seconds later, 0.100 mL (1.0 μmol) of the "activator solution" followed immediately by 0.400 mL of toluene, were injected into the reaction vessel. About another 30 seconds later, 0.170 mL of the 1 mL vial contents, followed immediately by 0.330 mL of toluene, were injected into the reaction vessel. Results are presented in Table 5.

Comparative Example

Ethylene-Styrene Polymerizations Using Zirconium-Ligand Compositions

Preparation of Stock Solutions: The "group 13 reagent solution" is a 0.20 M solution of triisobutylaluminium (TIBA). The "activator solution" is a 10 mM solution of N,N'-dimethylanilinium tetrakis(pentafluorophenyl)borate in toluene (160 mg in 20 mL toluene), heated to approximately 85° C. to fully dissolve the N,N'-dimethylanilinium tetrakis(pentafluorophenyl)borate.

In situ preparation of zirconium-ligand compositions: Stock solutions were prepared as follows: The "metal precursor solution" is a 25 mM solution of $Zr(CH_2C_6H_5)_4$ in toluene (28.5 mg in 2.50 mL toluene). The "ligand solutions" are a 25 mM solution the respective ligands in toluene, prepared in an array of 1 mL glass vials by adding 0.060 mL of toluene to 1.5 μmol of the ligand in a 1 mL glass vial. To each 1 mL glass vial containing ligand/toluene solution was added 0.060 mL of the metal precursor solution (1.5 μmol), to form the metal-ligand combination solution. To each metal-ligand combination solution was then added 0.060 mL of a 0.5 M 1-octene solution in toluene (30 μmol of 1-octene). The resultant solutions was allowed to sit at room temperature for 1 hour prior to addition of TIBA solution and injection into the reactor, as described below. Table 5 illustrates the zirconium-ligand solutions prepared:

Injection of solutions into the pressure reactor vessel: After the toluene mixture was saturated with ethylene at 100 psi pressure, 0.500 mL of styrene followed immediately by 0.500 mL of toluene, were injected into the pressure reaction vessel. About 30 seconds later, 0.075 mL (15 μmol) of the group 13 reagent solution was added to the 1 mL vial. About another 30 seconds later, 0.100 mL (1.0 μmol) of the "activator solution" followed immediately by 0.400 mL of toluene, were injected into the reaction vessel. About another 30 seconds later, 0.170 mL of the 1 mL vial contents, followed immediately by 0.330 mL of toluene, were injected into the reaction vessel. Results are presented in Table 5.

TABLE 5

$Hf(CH_2C_6H_5)_4$ and $Zr(CH_2C_6H_5)_4$-Ligand Compositions: Ethylene-Styrene Copolymerization Results:

| | $Zr(CH_2C_6H_5)_4$ | | $Hf(CH_2C_6H_5)_4$ | |
| --- | --- | --- | --- | --- |
| Ligand | Yield (mg) | wt. % Styrene by NMR | Yield (mg) | wt. % Styrene by NMR |
| 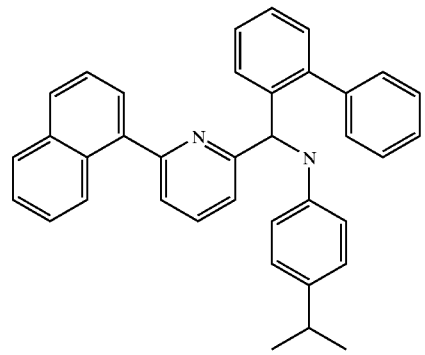 | 152 | 6 | 469 | 14 |

TABLE 5-continued

Hf(CH$_2$C$_6$H$_5$)$_4$ and Zr(CH$_2$C$_6$H$_5$)$_4$-Ligand Compositions: Ethylene-Styrene Copolymerization Results:

| Ligand | Zr(CH$_2$C$_6$H$_5$)$_4$ | | Hf(CH$_2$C$_6$H$_5$)$_4$ | |
|---|---|---|---|---|
| | Yield (mg) | wt. % Styrene by NMR | Yield (mg) | wt. % Styrene by NMR |
| 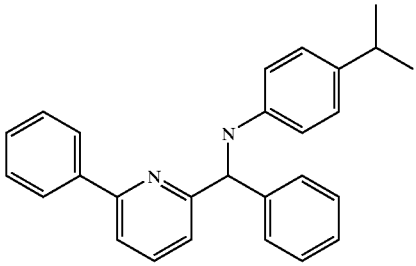 | 209 | 7 | 326 | 15 |
| 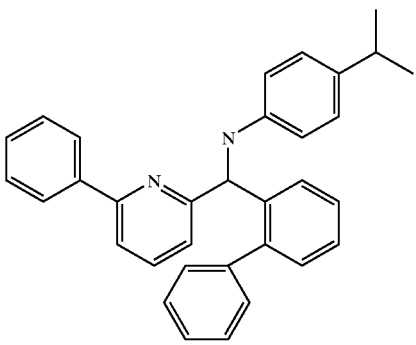 | 138 | 7 | 295 | 15 |
| 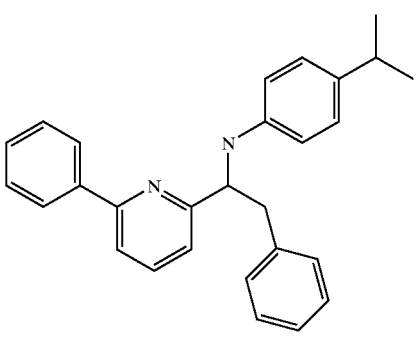 | 163 | 7 | 278 | 10 |
| 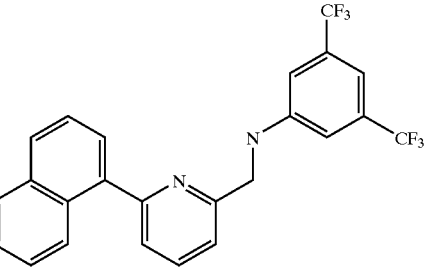 | 134 | 6 | 153 | 15 |

Example 3A

Ethylene-Styrene Polymerizations Using Hafnium-Ligand Compositions

This example comprises four polymerization reactions carried out with different ligand/hafnium compositions for the copolymerization of ethylene and styrene. The results are summarized in Table 5A, along with four comparative examples of polymerization reactions carried out with different ligand/zirconium compositions for the copolymerization of ethylene and styrene.

Preparation of the polymerization reactor prior to injection of catalyst composition: A pre-weighed glass vial insert and disposable stirring paddle were fitted to each reaction vessel of the reactor. The reactor was then closed, 0.10 mL of a 0.02 M solution of diisobutylaluminiumhydride ("DIBAL") in toluene and 3.8 mL of toluene were injected into each pressure reaction vessel through a valve. The temperature was then set to 110° C., and the stirring speed was set to 800 rpm, and the mixture was exposed to ethylene at 100 psi pressure. An ethylene pressure of 100 psi in the pressure cell and the temperature setting were maintained, using computer control, until the end of the polymerization experiment.

Preparation of the group 13 reagent and activator stock solutions: The "activator solution" is a 5 mM solution of N,N'-dimethylanilinium tetrakis (pentafluorophenyl) borate in toluene ("ABF20"). The solution is heated to approximately 85° C. to dissolve the reagent. The group 13 reagent solution is a 0.2 M solution of diisobutylaluminiumhydride ("DIBAL") in toluene.

In situ preparation of metal-ligand compositions: Stock solutions were prepared as follows: The "metal precursor solution" is a 10 mM solution of $Hf(NMe_2)_4$ in toluene. The "ligand solutions" are 25 mM solutions of the representative ligands in toluene, prepared in an array of 1 mL glass vials by dispensing 0.030 mL of a 25 mM ligand solution in a 1 mL glass vial. To each 1 mL glass vial containing ligand/toluene solution was added 0.075 mL of the metal precursor solution (0.75 μmol), to form the metal-ligand combination solution. The reaction mixtures we allowed to sit at 80° C. for 2–3 hours during which time most of the solvent evaporates. The reaction mixtures were dried completely by blowing a stream of Argon over the 1 mL vial. Prior to addition of alkylation and activator solution, a small amount of solvent (0.020 mL) was added to the dry composition.

Activation and Injection of solutions into the pressure reactor vessel: To the ligand metal composition, 0.037 mL of a 500 mM solution of 1-octene in toluene and 0.020 mL of toluene and 0.112 mL of the group 13 reagent solution was added to the 1 mL vial. Around 11 min later, 0.420 mL of styrene followed immediately by 0.380 mL of toluene, were injected into the prepressurized reaction vessel. Another 1 min later, 0.165 mL (0.845 μmol) of the "activator solution" was added to the 1 mL vial. About another 30 seconds later, 0.181 mL of the 1 mL vial contents, followed immediately by 0.619 mL of toluene, were injected into the reaction vessel.

Polymerization: The polymerization reaction was allowed to continue for the 217–601 seconds, during which time the temperature and pressure were maintained at their pre-set levels by computer control. The polymerization times were the lesser of the maximum desired polymerization reaction time or the time taken for a predetermined amount of monomer gas to be consumed in the polymerization reaction. The specific times for each polymerization are shown in table 5B the column titled $Hf(NMe_2)_4$. After the reaction time elapsed, the reaction was quenched by addition of an overpressure of carbon dioxide.

Product work up: ethylene/styrene copolymerizations After the polymerization reaction, the glass vial insert, containing the polymer product and solvent, was removed from the pressure cell and removed from the inert atmosphere dry box, and the volatile components were removed using a centrifuge vacuum evaporator. After most of the volatile components had evaporated, the vial contents were dried thoroughly by evaporation at elevated temperature under reduced pressure. The vial was then weighed to determine the yield of polymer product. The polymer product was then analyzed by rapid GPC, as described above to determine the molecular weight of the polymer produced, and by FTIR spectroscopy to determine the styrene incorporation. Results are presented in Table 5A in the column titled $Hf(NMe_2)_4$.

Comparative Example

Ethylene-Styrene Polymerizations Using Zirconium-Ligand Compositions:

Preparation of the polymerization reactor prior to injection of catalyst composition: This part of the experiment was performed as described above for Example 3A using Hafnium-ligand compositions.

Preparation of the group 13 reagent and activator stock solutions: This part of the experiment was performed as described above for Example 3A using Hafnium-ligand compositions.

In situ preparation of metal-ligand compositions: This part of the experiment was performed as described above for Example 3A using Hafnium-ligand compositions except that the "metal precursor solution" is a 10 mM solution of $Zr(NMe_2)_4$ in toluene.

Activation and Injection of solutions into the pressure reactor vessel: This part of the experiment was performed as described above for Example 3A using Hafnium-ligand compositions.

Polymerization: This part of the experiment was performed as described above for Example 3A using Hafnium-ligand compositions, except that the polymerization reaction was allowed to continue for the 399–600 seconds. The specific times for each polymerization are shown in table 5B in the column titled $Zr(NMe_2)_4$.

Product work up: ethylene/styrene copolymerizations: This part of the experiment was performed as described above for Example 3A using Hafnium-ligand compositions. Results are presented in Table 5A in the column titled $Zr(NMe_2)_4$.

TABLE 5A $Hf(NMe_2)_4$ and $Zr(NMe_2)_4$-Ligand Compositions:
Ethylene-Styrene Copolymerization Results (Example 3A):

| | $Hf(NMe_2)_4$ | | $Zr(NMe_2)_4$ | |
|---|---|---|---|---|
| Ligand | Activity | mol% styrene (FTIR) | Activity | mol% styrene (FTIR) |
| L29 | 57 | 2.8 | 23 | 0.8 |
| L30 | 158 | 3.0 | 77 | 2.0 |
| L4 | 111 | 3.1 | 35 | 1.6 |
| L5 | 57 | 3.3 | 41 | 1.9 |

In Table 5A, Activity is shown in units of mg polymer per minute per μmol of Hf or Zr, mol % styrene is as determined by FTIR using PLS analysis, as described above.

TABLE 5B

Polymerization times in seconds for example 3A

| Ligand | $Hf(NMe_2)_4$ Polymerization time | $Zr(NMe_2)_4$ Polymerization time |
|---|---|---|
| L29 | 601 | 600 |
| L30 | 217 | 399 |
| L4 | 293 | 600 |
| L5 | 601 | 601 |

Example 4

Ethylene-Isobutylene Copolymerizations Using Hafnium-Ligand Compositions

Preparation of Stock Solutions: The "group 13 reagent solution" is a 20 mM solution of triethylaluminum (TEAL). The "activator solution" is a 5 mM solution of N,N'-dimethylanilinium tetrakis(pentafluorophenyl)borate in toluene (75 mg in 20 mL toluene), heated to approximately 85° C. to fully dissolve the N,N'-dimethylanilinium tetrakis (pentafluorophenyl)borate. The "metal precursor solution" is a 20 mM solution of $Hf(CH_2C_6H_5)_4$ in toluene (33 mg in 2.0 mL toluene). The "ligand solutions" are 20 mM solutions of the ligand shown below in Table 6 in toluene.

Ethylene-Isobutylene Copolymerizations: Pre-weighed glass vials each containing a disposable magnetic stir bar were placed into the positions of the reactor block. Using a liquid dispensing robot, 2.9 mL of toluene are added to these glass vials, followed by 0.180 mL of "ligand solution" and 0.200 mL of $Hf(CH_2C_6H_5)_4$ in toluene. These solutions were stirred for 30 minutes at room temperature after which 0.02 mL of a 20 mM solution of triethylaluminum (TEAL) in toluene were dispensed into each reaction vessel. Following a 10 minute waiting period, 0.700 mL of a 5 mM solution of N,N'-dimethylanilinium tetrakis(pentafluorophenyl)borate in toluene were added to each vial. The reactor was then closed, exposed to an ethylene/isobutylene gas mixture (ethylene feed 5 psi/isobutylene feed 10 psi pressure) and placed on a stirrer hotplate maintained at 50° C. for the duration of the experiment. After 60 minutes, the reactor was removed from the stirrer hotplate. The gases were vented from the reactor, the reactor opened and the glass vials removed.

Product work up: Ethylene-Isobutylene Polymerizations: The glass vials, containing the polymer product and solvent, were removed from the reactor and removed from the inert atmosphere dry box, and the volatile components were allowed to evaporate at room temperature in the air. After most of the volatile components had evaporated, the vial contents were dried thoroughly by evaporation under vacuo. The vial was then weighed to determine the yield of polymer product. The polymer product was then analyzed by $^1H$ NMR spectroscopy to determine the ratio of isobutylene to ethylene incorporated in the polymer product, represented as the weight % of isobutylene incorporated in the copolymer. Table 6 shows a summary of the results:

TABLE 6

$Hf(CH_2C_6H_5)_4$-Ligand Compositions: Ethylene-Isobutylene Copolymerization Results:

| Ligand | Yield (mg) | Wt. % IB |
|---|---|---|
| (structure) | 97 | 33 |

Example 5–10

Synthesis of Ligand/Metal Complexes 1–21.

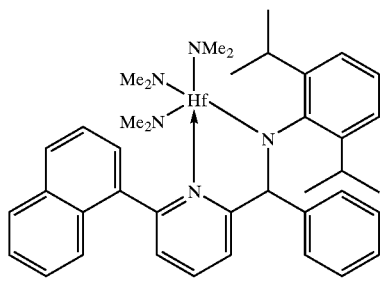

C1

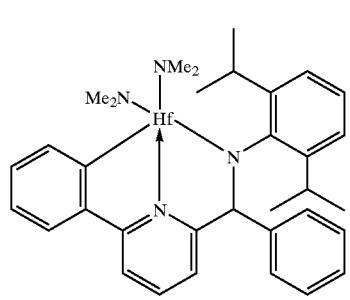

C2

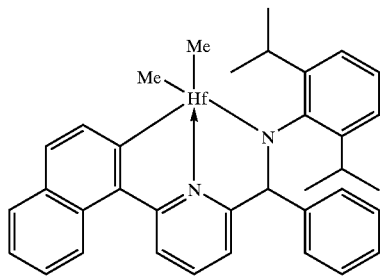

C3

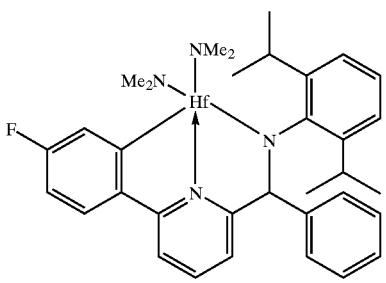

C4

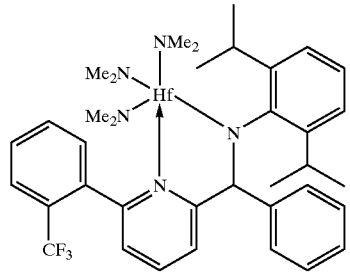

C5

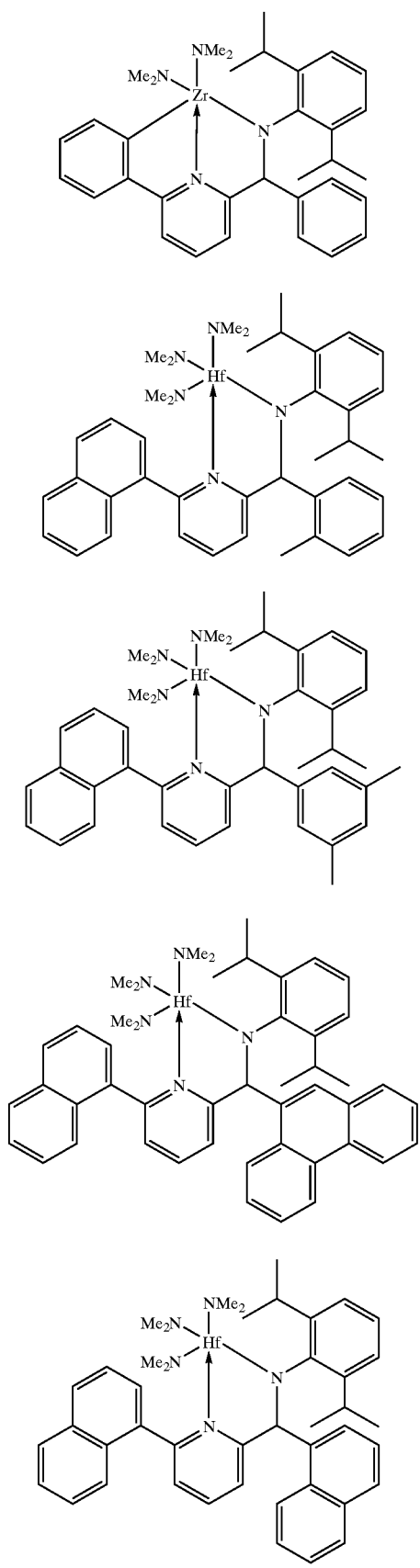
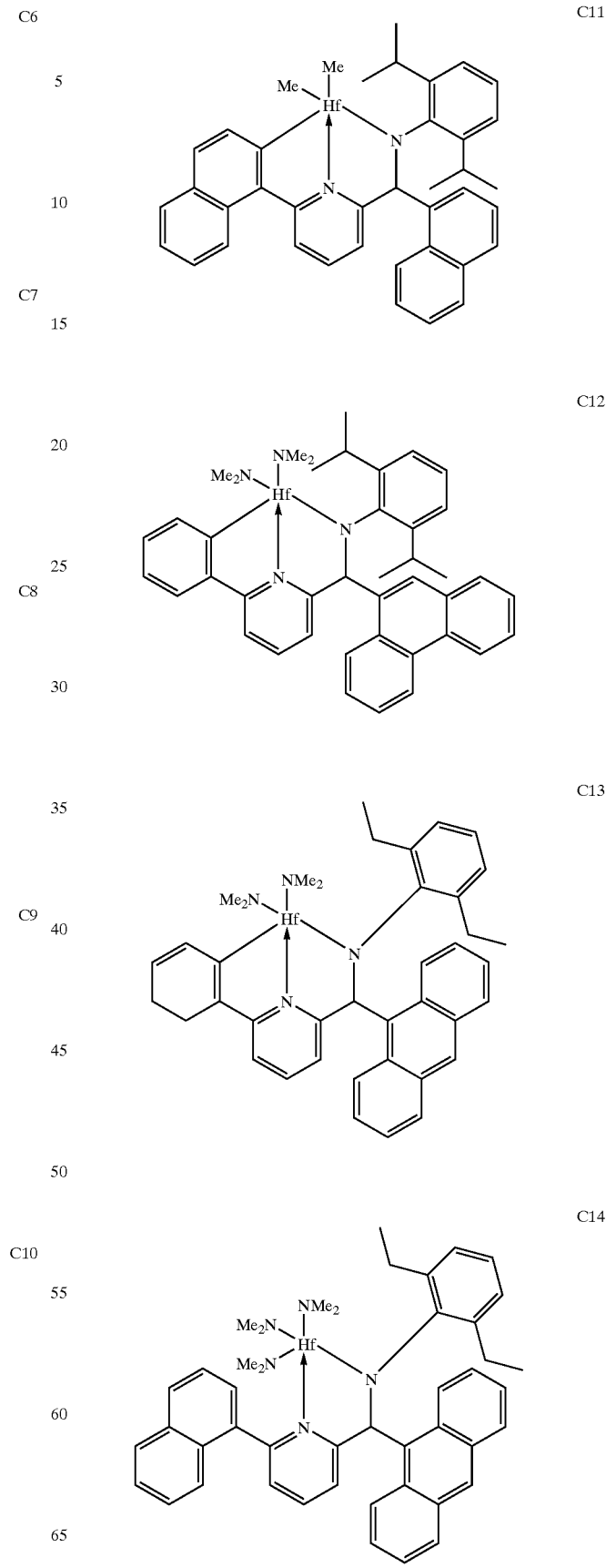

-continued

C15
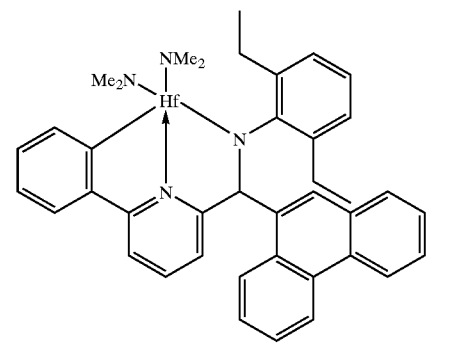

C16
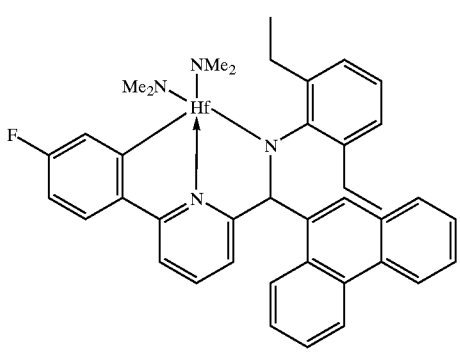

C17
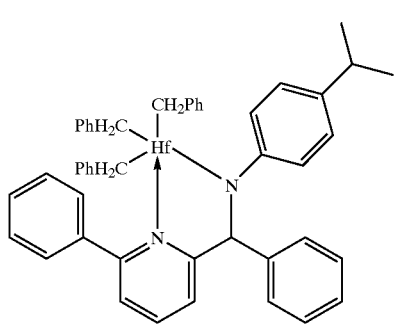

C18
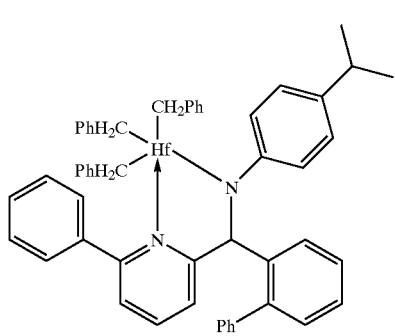

C19
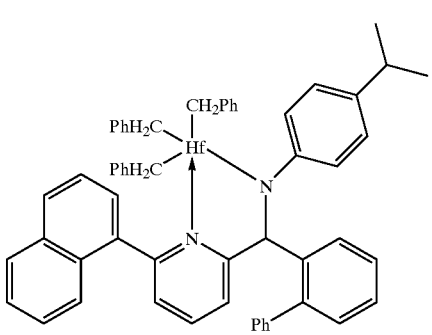

-continued

C20
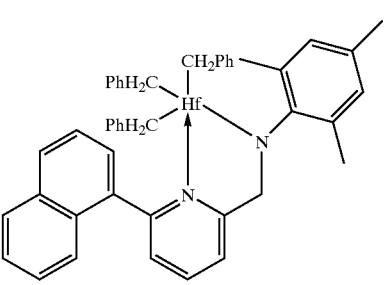

C21
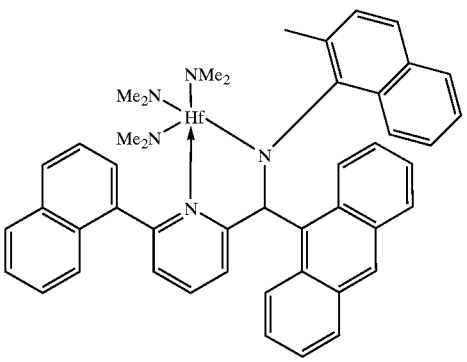

Example 5

Synthesis of Complex 1 (C 1)

The ligand L4 used in this example was prepared in the manner described above.

Hf(NMe$_2$)$_4$ (291 mg, 0.82 mmol) and L4, from above, (358 mg, 0.76 mmol) were combined in 5 mL C$_6$D$_6$. The reaction was heated to 70° C. and vented occasionally. Aliquots were analyzed by $^1$H NMR every hour until the reaction was complete (3 hours). Solvent was then removed, yielding a yellow glassy solid, which was extracted with hot pentane (20 mL) and filtered. The volume of the filtrate was reduced to 5 mL and then cooled to −35° C. A yellow microcrystalline powder was collected (439 mg, 74%) $^1$H NMR (δ C$_6$D$_6$). 6.55–7.75 (overlapping m, 17H total, Ar), 5.93, (s, 1H, CHpy), 3.65 (sept, 1H, CH-iPr), 3.31 (sept, 1H, CH-iPr), 2.83 (br s, 6, NMe$_2$), 2.67 (br s, 6, NMe$_2$), 2.22 (br s, 6, NMe$_2$), 1.64 (d, 3H, CHMe$_2$), 1.53 (d, 3H, CHMe$_2$), 1.23 (d, 3H, CHMe$_2$), 0.26 (d, 3H, CHMe$_2$). Crystals suitable for X-ray analysis were obtained by re-crystallization from hot hexane and submitted for single crystal X-ray analysis, which confirmed the structure shown above.

Example 6

Synthesis of Complex 2 (C 2)

The ligand L5 used in the example was prepared in the manner described above.

Hf(NMe$_2$)$_4$ (121 mg, 0.34 mmol) and L5, from above, (130 mg, 0.31 mmol) were combined in 5 mL toluene. The reaction was heated to 110° C. and vented occasionally. Aliquots were analyzed by $^1$H NMR until the reaction was complete (24 hours). Solvent was then removed, yielding a yellow glassy solid, which was extracted with hot pentane (20 mL) and filtered. The volume of the filtrate was reduced to 5 mL and then cooled to −35° C. A yellow microcrystalline powder was collected (150 mg; 71%). $^1$H NMR (δ

$C_6D_6$). 8.36, 7.69 (d, 1H each, Ar) 6.9–7.5 (overlapping m, 12H total, Ar), 6.55 (d, 1H, Ar) 6.10, (s, 1H, CHpy), 3.50 (sept, 1H, CH-iPr), 3.18 (s, 6, $NMe_2$), 2.88 (s, 6, $NMe_2$), 1.52 (d, 3H, $CHMe_2$), 1.39 (d, 3H, $CHMe_2$), 1.17 (d, 3H $CHMe_2$), 0.49 (d, 3H, $CHMe_2$). Crystals suitable for x-ray diffraction were obtained by recrystallization from hot pentane and submitted for single crystal X-ray analysis, which confirmed the structure shown above.

Examples 7A and 7B

7A Synthesis of complex 3 (C 3): Complex 1, from Example 5 above, (51 mg, 0.065 mmol) was dissolved in 7 mL pentane. The mixture was cooled to −35° C. and a 2.0 M solution of $AlMe_3$ in toluene (330 μL, 0.66 mmol, 10 eq.) was added. A yellow precipitate formed and then redissolved as the reaction was allowed to warm to room temperature. The mixture was stirred at room temperature for 1 hour, and then the solvent was removed. The resulting yellow powder was recrystallized from pentane at −35° C. Yellow microcrystals (25 mg) were collected and dried. A second crop yielded an additional 7 mg of crystals. (combined yield= 73%) $^1$H NMR ($C_6D_6$). 8.56, 8.23, 7.80, 7.72, 7.46 (d, 1 H each, Ar) 7.0–7.4 (overlapping m, 10H total), 6.40 (d, 1H, Ar), 5.92, (s, 1H, CHpy), 3.82 (sept, 1H, CH-iPr), 3.27 (sept, 1H, CH-iPr), 1.38 (overlapping two d, 6H total, $CHMe_2$), 1.15 (d, 3H, CHMe2), 0.93 (s, 3H, Hf-Me), 0.65 (s, 3H, Hf-Me), 0.38 (d, 3H, $CHMe_2$).

7B Synthesis of complex 11 (C 11): In a manner similar to that described in example 7A, complex 11 was synthesized from complex 10.

Examples 8A–8F

8A: Synthesis of complex 4 (C 4): The ligand used in the example was prepared in the manner generally described above for L1, shown above.

In a manner similar to that described in example 6, the complex was prepared from L1, from above, (48 mg, 0.11 mmol) and $Hf(NMe_2)_4$ (0.12 mmol) in $C_6D_6$. The mixture was heated to 100° C. for 24 hours, and then recrystalized from pentane (44 mg, 58%). $^1$H NMR was consistent with the formation of the complex whose structure is shown above.

8B: Synthesis of complex 6 (C6): The ligand used in the example was prepared in the manner generally described above for L5, shown above.

In a manner similar to that described in example 7, complex 6 whose structure is shown above was prepared from L5, from above, (20 mg, 0.05 mmol) and $Zr(NMe_2)_4$ (13 mg, 0.05 mmol) in $C_6D_6$. After heating to 100° C. for 24 hours, yellow crystals were obtained by recrystallization from pentane. (yield=15 mg, 50%). $^1$H NMR was consistent with the formation of the complex.

8C: Synthesis of complex 12 (C 12): In a manner similar to that described in example 7, complex 12 whose structure is shown above was prepared from L20, from above.

8D: Synthesis of complex 13 (C 13): In a manner similar to that described in example 7, complex 13 whose structure is shown above was prepared from L21, from above.

8E: Synthesis of complex 15 (C 15): In a manner similar to that described in example 7, complex 12 whose structure is shown above was prepared from L23, from above.

8F: Synthesis of complex 16 (C 16): In a manner similar to that described in example 7, complex 12 whose structure is shown above was prepared from L24, from above.

Examples 9A–9F

9A Synthesis of complex 5: The ligand used in the example was prepared in the manner generally described above for L4, shown above. In a manner similar to that described in example 5, the complex whose structure is shown above was prepared from L3, from above, (43 mg, 0.09 mmol) and $Hf(NMe_2)_4$ (56 mg, 0.16 mmol) in $C_6D_6$. The mixture was heated to 100° C. for 48 hours, and then recrystalized from pentane (46 mg, 66%). $^1$H NMR was consistent with the formation of the complex.

9B Synthesis of complex 7: The ligand used in the example was prepared in the manner generally described above for L4, shown above. In a manner similar to that described in example 5, the complex whose structure is shown above was prepared from L7, from above.

9C Synthesis of complex 8: The ligand used in the example was prepared in the manner generally described above for L4, shown above. In a manner similar to that described in example 5, the complex whose structure is shown above was prepared from L6, from above.

9D Synthesis of complex 9: The ligand used in the example was prepared in the manner generally described above for L4, shown above. In a manner similar to that described in example 5, the complex whose structure is shown above was prepared from L9, from above.

9E Synthesis of complex 10: The ligand used in the example was prepared in the manner generally described above for L4, shown above. In a manner similar to that described in example 5, the complex whose structure is shown above was prepared from L8, from above.

9F Synthesis of complex 14: The ligand used in the example was prepared in the manner generally described above for L4, shown above. In a manner similar to that described in example 5, the complex whose structure is shown above was prepared from L22, from above.

9G Synthesis of complex 21: The ligand used in the example was prepared in the manner generally described above for L4, shown above. In a manner similar to that described in example 5, the complex whose structure is shown above was prepared from L30, from above.

Examples 10A–10D

Synthesis of Hafnium Benzyl Complexes C17–C20

10A Synthesis of complex 17 (C 17): The ligand used in the example was prepared in a manner generally described above for L4, shown above. Ligand L25 (202 mg, 0.53 mmol) was dissolved in 4 mL toluene and solid $Hf(Bz)_4$ (306 mg, 0.56 mmol) was added. The solution was stirred for 1 hour. $^1$H NMR of an aliquot of the reaction mixture revealed that the reaction was complete. The volume was reduced to 1 mL, and pentane (10 mL) was added. A yellow precipitate was collected, washed with pentane and dried. $^1$H NMR was consistent with the proposed formula 10B Synthesis of complex 18 (C 18): The ligand used in the example was prepared in a manner generally described above for L4, shown above. In a manner similar to that descibed in example 10A, the complex whose structure is shown above was prepared from L26 and $Hf(CH_2Ph)_4$ in $C_6D_6$.

10C Synthesis of complex 19 (C 19): The ligand used in the example was prepared in a manner generally described above for L4, shown above. In a manner similar to that descibed in example 10A, the complex whose structure is shown above was prepared from L27 and $Hf(CH_2Ph)_4$ in $C_6D_6$.

10D Synthesis of complex 20 (C 20): The ligand used in the example was prepared in a manner generally described above for L4, shown above. In a manner similar to that descibed in example 10A, the complex whose structure is shown above was prepared from L28 and Hf(CH$_2$Ph)$_4$ in C$_6$D$_6$.

Examples 11–14, 16–24

Presentation of the Results

In the following Examples 11–14 and 16–24, the polymerizations carried out for the particular example are represented in the first table within each example. This first table within each example describes the identity of either ligand (L#) or metal complex (C#) used in each experiment represented as entry in the grid framed by the rows and columns labeled with letters and numbers respectively. Additional experimental details described in the paragraphs: "Preparation of the polymerization reactor prior to injection of catalyst composition" and "Activation and Injection of solutions into the pressure reactor vessel" such as "group 13 reagent", $t_1$, $t_2$, Injection fraction, Polym. Temp. (abbreviation for polymerization temperature), Premix Temperature and Activator are given in the first table. Experimental details which apply to each experiment in a row of the grid are listed to the right of the row to which they refer. Experimental details which apply to each experiment in a column of the grid are listed below the column to which they refer.

For example the experiment 11.B.2. employs complex C1, and for this example the "group 13 reagent" is TMA, $t_1$ is 0.5 minutes, $t_2$ is 10 minutes, Injection fraction is 0.066, Polym. Temp. (abbreviation for polymerization temperature) is 110° C., Premix temperature is 24° C. and Activator is ABF20.

The data in the subsequent tables of each example are also represented in grid format as entries in grids framed by the rows and columns labeled with letters and numbers respectively, such that the data in each lettered row and numbered column corresponds to the experiments described in the corresponding lettered and numbered rows and columns in the first table of each example. For example the experiment 11.B.2. the reaction time is 217 seconds, the activity is 877 mg polymer per minute per $\mu$mol, the crystallinity index is 0.83 and the weight average molecular weight is 163,000 (represented in the table as 163 k).

Example 11

Propylene Polymerizations at 110° C.

Sixteen polymerization experiments were carried out in this example, using different metal complexes, activator amounts, group 13 reagents and activating conditions.

Preparation of the polymerization reactor prior to injection of catalyst composition: A pre-weighed glass vial insert and disposable stirring paddle were fitted to each reaction vessel of the reactor. The reactor was then closed, 0.10 mL of a 0.02 M solution of group 13 reagents in toluene and 3.9 mL of toluene were injected into each pressure reaction vessel through a valve. The temperature was then set to the appropriate setting (with specific temperatures for each polymerization being listed in table 7, below), and the stirring speed was set to 800 rpm, and the mixture was exposed to propylene at 100 psi pressure. A propylene pressure of 100 psi in the pressure cell and the temperature setting were maintained, using computer control, until the end of the polymerization experiment.

Preparation of the group 13 reagent and activator stock solutions: The "activator solution" is a 5 mM solution of N,N'-dimethylanilinium tetrakis (pentafluorophenyl) borate in toluene ("ABF20"). The solution is heated to approximately 85° C. to dissolve the reagent. The "group 13 reagent" solution is either a 0.2 M solution of diisobutylaluminiumhydride ("DIBAL") or a 0.2 M solution of triethylboron ("BEt3") or a 0.2 M solution of trimethylaluminium ("TMA") or a solution that is 0.133 M in triethyl boron and 0.066M in diisobutyl aluminium hydride ("DIBAL/BEt3"), all "group 13 reagent" solutions were solutions in toluene.

Activation and Injection of solutions into the pressure reactor vessel: First, an appropriate amount of the 0.2 M group 13 reagent solution was dispensed into a 1 mL vial that was kept at a constant premix temperature as specified in the table 7. 0.100 mL (0.5 $\mu$mol) of the metal complex solution (5 mM in toluene) was added to the 1 mL vial. This mixture was held at a premix temperature for a time period of $t_1$ as indicated in table 7. Then, 0.110 mL (0.55 $\mu$mol) of the "activator solution" was added to the 1 mL vial. After the time period $t_2$ elapsed (time listed in table 7), a fraction of the total 1 mL vial contents (listed in table 7), followed immediately by approximately 0.3 mL of toluene, were injected into the reaction vessel. The array of experiments with values for equivalents of group 13 reagent, $t_1$, $t_2$ and injection fraction is described in table 7.

Polymerization: The polymerization reaction was allowed to continue for times shown in table 7A, during which time the temperature and pressure were maintained at their preset levels by computer control. After the reaction time elapsed, the reaction was quenched by addition of an overpressure of carbon dioxide sent to the reactor. The polymerization times were the lesser of the maximum desired polymerization reaction time or the time taken for a predetermined amount of monomer gas to be consumed in the polymerization reaction.

Product work up: Propylene Polymerizations After the polymerization reaction, the glass vial insert, containing the polymer product and solvent, was removed from the pressure cell and removed from the inert atmosphere dry box, and the volatile components were removed using a centrifuge vacuum evaporator. After most of the volatile components had evaporated, the vial contents were dried thoroughly by evaporation at elevated temperature under reduced pressure. The vial was then weighed to determine the yield of polymer product. The polymer product was then analyzed by rapid GPC, as described above to determine the molecular weight of the polymer produced, and by FTIR spectroscopy to determine the crystallinity index. Results are presented in the tables 8–10.

TABLE 7

Description of array of polymerization experiments (examples 11.A.1.–11.D.4.)

|   | 1 | 2 | 3 | 4 | group 13 reagent[a] | group 13 reagent[b] |
|---|---|---|---|---|---|---|
| A | C 1 | C 1 | C 1 | C 1 | 10 DIBAL/ 20 BEt3 | BEt3 |
| B | C 1 | C 1 | C 1 | C 1 | 10 TMA | TMA |
| C | C 3 | C 3 | C 3 | C 3 | 10 DIBAL/ 20 BEt3 | BEt3 |

TABLE 7-continued

Description of array of polymerization experiments (examples 11.A.1.–11.D.4.)

|   | 1 | 2 | 3 | 4 | group 13 reagent[a] | group 13 reagent[b] |
|---|---|---|---|---|---|---|
| D | C 3 | C 3 | C 3 | C 3 | 10 TMA | TMA |
| $t_1$ (min) | 10 | 0.5 | 10 | 0.5 | | |
| $t_2$ (min) | 0.5 | 10 | 0.5 | 0.5 | | |
| Injection fraction | 0.066 | 0.066 | 0.066 | 0.066 | | |
| Polym. Temp (° C.) | 110 | 110 | 110 | 110 | | |
| Premix Temp (° C.) | 24 | 24 | 52 | 52 | | |
| Activator | ABF20 | ABF20 | ABF20 | ABF20 | | |

[a]Number of equivalents and identity of group 13 reagent added to metal complex as described in activation steps.
[b]Group 13 reagent, which was placed in reaction vessel prior to catalyst injection (0.02 M solution was used).

TABLE 7A reaction times in seconds of experiments 11.A.1.–11.D.4.

|   | 1 | 2 | 3 | 4 |
|---|---|---|---|---|
| A | 490 | 601 | 601 | 600 |
| B | 214 | 217 | 264 | 213 |
| C | 406 | 601 | 555 | 374 |
| D | 208 | 243 | 264 | 254 |

TABLE 8

Activity (mg polymer per minute per μmol) of examples 11.A.1.–11.D.4.

|   | 1 | 2 | 3 | 4 |
|---|---|---|---|---|
| A | 320 | 198 | 253 | 254 |
| B | 864 | 877 | 648 | 780 |
| C | 503 | 319 | 300 | 457 |
| D | 872 | 722 | 651 | 649 |

TABLE 9

Crystallinity index of examples 11.A.1.–11.D.4.

|   | 1 | 2 | 3 | 4 |
|---|---|---|---|---|
| A | 0.81 | 0.77 | 0.79 | 0.78 |
| B | 0.77 | 0.83 | 0.78 | 0.79 |
| C | 0.77 | 0.77 | 0.79 | 0.74 |
| D | 0.78 | 0.75 | 0.79 | 0.79 |

TABLE 10

Weight average molecular weight (k) of examples 11.A.1.–11.D.4.

|   | 1 | 2 | 3 | 4 |
|---|---|---|---|---|
| A | 174 | 187 | 184 | 196 |
| B | 143 | 163 | 162 | 155 |
| C | 174 | 184 | 178 | 186 |
| D | 155 | 165 | 168 | 167 |

Example 12

Propylene Polymerization Using Metal Complex 1 at Different Polymerization Temperatures In this example, forty-eight polymerization reactions were carried out. The reactor was prepared as in Example 11, above. In addition, the polymerization was run in the same manner and the polypropylene polymer was worked up in the same manner as in Example 11, above.

Preparation of the group 13 reagent and activator stock solutions: The "activator solution" is a 5 mM solution of N,N'-dimethylanilinium tetrakis (pentafluorophenyl) borate in toluene ("ABF20") or a toluene solution which is 5 mM in N,N'-dimethylanilinium tertakis(pentafluorophenyl) borate and 10 mM in tris(pentafluorophenyl) borane (referred to in table 5 as "cocktail"). Both solutions are heated to approximately 85° C. to dissolve the reagent. The group 13 reagent solution is either a 0.2 M solution of diisobutylaluminiumhydride ("DIBAL") or a 0.2 M solution of triethylboron ("BEt3") or a 0.2 M solution of triisobutylaluminium ("TIBA") or a solution which is 0.133 M in triethyl boron and 0.033M in diisobutyl aluminium hydride ("DIBAL/BEt3") or a solution which is 0.133 M in triethyl boron and 0.066M in triisobutylaluminium ("TIBA/BEt3").

Activation and Injection of solutions into the pressure reactor vessel: An appropriate amount based on the equivalents presented in table 11 of a 0.2M solution of the group 13 reagent is dispensed into a 1 mL vial. 0.100 mL of a 5 mM solution of metal complex 1 is added. After 9 minutes, 0.110 mL solution of the "activator solution" in toluene was added to the 1 mL vial, with the appropriate activator solution being identified in table 11. About another 30 seconds later a fraction of the total 1 mL vial contents (with the fractional amount being identified in table 11, such that e.g., 0.2 refers to 20% by volume), followed immediately by around 0.300 mL of toluene, were injected into the reaction vessel. The array of experiments is described in table 11. The specific times for each polymerization are shown in table 11a. The results are presented in tables 12–15.

TABLE 11

Description of polymerization experiments using Complex 1 (examples 12.A.1–12.H.6):

| | 1 | 2 | 3 | 4 | 5 | 6 | group 13 reagent[a] | Group 13 reagent[b] |
|---|---|---|---|---|---|---|---|---|
| A | C 1 | C 1 | C 1 | C 1 | C 1 | C 1 | 30 DIBAL | DIBAL |
| B | C 1 | C 1 | C 1 | C 1 | C 1 | C 1 | 10 DIBAL | $BEt_3$ |
| C | C 1 | C 1 | C 1 | C 1 | C 1 | C 1 | 10 DIBAL/ 20 $BEt_3$ | $BEt_3$ |
| D | C 1 | C 1 | C 1 | C 1 | C 1 | C 1 | 30 TIBA | TIBA |
| E | C 1 | C 1 | C 1 | C 1 | C 1 | C 1 | 10 TIBA | $BEt_3$ |
| F | C 1 | C 1 | C 1 | C 1 | C 1 | C 1 | 10 TIBA/ 20 $BEt_3$ | $BEt_3$ |
| G | C 1 | C 1 | C 1 | C 1 | C 1 | C 1 | 30 $BEt_3$ | $BEt_3$ |
| H | C 1 | C 1 | C 1 | C 1 | C 1 | C 1 | 60 $BEt_3$ | $BEt_3$ |
| Injection Fraction | 0.2 | 0.2 | 0.2 | 0.1 | 0.2 | 0.2 | | |
| Polym. Temp. (° C.) | 75 | 75 | 90 | 75 | 75 | 110 | | |
| Activator | ABF20 | ABF20 | ABF20 | ABF20 | Cocktail | Cocktail | | |

[a] Number of equivalents and identity of group 13 reagent added to Metal Complex as described in activation steps
[b] Group 13 reagent, which was placed in reaction vessel prior of catalyst injection (0.02 M solution was used).

TABLE 11A polymerization times in seconds for examples 12.A.1.–12.H.6.

| | 1 | 2 | 3 | 4 | 5 | 6 |
|---|---|---|---|---|---|---|
| A | 679 | 621 | 296 | 860 | 826 | 313 |
| B | 486 | 480 | 889 | 567 | 520 | 382 |
| C | 385 | 400 | 472 | 378 | 608 | 225 |
| D | 902 | 901 | 612 | 901 | 901 | 901 |
| E | 900 | 900 | 901 | 901 | 901 | 901 |
| F | 516 | 507 | 773 | 594 | 689 | 900 |
| G | 900 | 900 | 900 | 900 | 607 | 900 |
| H | 655 | 457 | 900 | 900 | 464 | 900 |

TABLE 12

Activity (mg polymer per minute per μmol) of examples 12.A.1.–12.H.6.

| | 1 | 2 | 3 | 4 | 5 | 6 |
|---|---|---|---|---|---|---|
| A | 390 | 365 | 312 | 473 | 255 | 192 |
| B | 381 | 356 | 237 | 389 | 195 | 150 |
| C | 681 | 605 | 420 | 1212 | 288 | 285 |
| D | 108 | 102 | 94 | 145 | 23 | 18 |
| E | 74 | 64 | 61 | 34 | 20 | 47 |
| F | 403 | 378 | 231 | 588 | 157 | 37 |
| G | 62 | 80 | n/d | 10 | 158 | 4 |
| H | 176 | 396 | 208 | 36 | 236 | 4 | n/d: no data

TABLE 13

Crystallinity index of examples 12.A.1.–12.H.6.

| | 1 | 2 | 3 | 4 | 5 | 6 |
|---|---|---|---|---|---|---|
| A | 0.87 | 0.85 | 0.84 | 0.86 | 0.85 | 0.85 |
| B | 0.84 | 0.84 | 0.81 | 0.84 | 0.84 | 0.82 |
| C | 0.85 | 0.77 | 0.83 | 0.85 | 0.84 | 0.81 |
| D | 0.89 | 0.88 | 0.82 | 0.89 | 0.90 | 0.81 |
| E | 0.86 | 0.86 | 0.82 | 0.82 | 0.81 | 0.74 |
| F | 0.85 | 0.82 | 0.83 | 0.84 | 0.84 | 0.75 |
| G | 0.84 | 0.83 | nd | nd | 0.80 | nd |
| H | 0.83 | 0.78 | 0.86 | 0.80 | 0.81 | nd | nd: not determined

TABLE 14

Weight average molecular weight (k) of examples 12.A.1.–12.H.6.

| | 1 | 2 | 3 | 4 | 5 | 6 |
|---|---|---|---|---|---|---|
| A | 1348 | 1356 | 708 | 1728 | 1419 | 166 |
| B | 2748 | 2934 | 1112 | 3852 | 4469 | 283 |
| C | 1301 | 1437 | 714 | 2022 | 2844 | 214 |
| D | 2568 | 2381 | 1210 | 3011 | 2085 | nd |
| E | 3819 | 4071 | 2109 | 3675 | 3944 | 331 |
| F | 2034 | 2179 | 1076 | 2678 | 3269 | 271 |
| G | 4641 | 4524 | nd | nd | 4008 | nd |
| H | 3390 | 2858 | 1046 | 3059 | 3421 | nd | nd: not determined

TABLE 15

Melting points in ° C. of examples 12.A.1., 12.A.3., 12.A.6., 12.C.1., 12.C.3. and 12.C.6.

| | 1 | 2 | 3 | 4 | 5 | 6 |
|---|---|---|---|---|---|---|
| A | 143 | | 141 | | | 138 |
| B | | | | | | |
| C | 140 | | 139 | | | 137 |

Example 13

Ethylene/Styrene Copolymerization Using Metal Complexes

Twenty-three polymerization reactions were run with different metal complexes, temperatures, activators and activating conditions for copolymerization of ethylene and styrene.

Preparation of the polymerization reactor prior to injection of catalyst composition: A pre-weighed glass vial insert and disposable stirring paddle were fitted to each reaction vessel of the reactor. The reactor was then closed, 0.10 mL of a 0.02 M group 13 reagent solution in toluene and 3.8 mL of toluene were injected into each pressure reaction vessel through a valve (see table 16 for the reagents used). The identity of the group 13 reagent solution is given in table 16. The temperature was then set to 110° C., and the stirring speed was set to 800 rpm, and the mixture was exposed to ethylene at 100 psi pressure. An ethylene pressure of 100 psi in the pressure cell and the temperature setting were maintained, using computer control, until the end of the polymerization experiment.

Preparation of the group 13 reagent and activator stock solutions: The "activator solution" is a 5 mM solution of N,N'-dimethylanilinium tetrakis (pentafluorophenyl) borate in toluene ("ABF20"). The solution is heated to approximately 85° C. to dissolve the reagent. The group 13 reagent solution is either a 0.2 M solution of diisobutylaluminium-hydride ("DIBAL") or a 0.2 M solution of trimethylaluminium ("TMA"), both in toluene.

Activation and Injection of solutions into the pressure reactor vessel: First, an appropriate amount of the 0.2 M group 13 reagent solution was dispensed in a 1 mL vial which was kept at a constant premix temperature as specified in the table 16. Then 0.100 mL of the metal complex solution (5 mM in toluene) was added. This mixture was held at a premix temperature for a time $t_1$ as indicated in table 16, during which time, 0.420 mL of styrene followed immediately by 0.380 mL of toluene, were injected into the prepressurized reaction vessel. Then, 0.110 mL (0.55 μmol) of the "activator solution" was added to the 1 mL vial. After the time period $t_2$ elapsed, a fraction (as indicated in table 16) of the total 1 mL vial contents, followed immediately by approximately 0.3 mL of toluene were injected into the reaction vessel. The array of experiments is described in table 16.

Polymerization: The polymerization reaction was allowed to continue for the 400–600 seconds, during which time the temperature and pressure were maintained at their pre-set levels by computer control, with the specific times for polymerization listed in table 16A. The polymerization times were the lesser of the maximum desired polymerization reaction time or the time taken for a predetermined amount of monomer gas to be consumed in the polymerization reaction. After the reaction time elapsed, the reaction was quenched by addition of an overpressure of carbon dioxide.

Product work up: ethylene/styrene copolymerizations After the polymerization reaction, the glass vial insert, containing the polymer product and solvent, was removed from the pressure cell and removed from the inert atmosphere dry box, and the volatile components were removed using a centrifuge vacuum evaporator. After most of the volatile components had evaporated, the vial contents were dried thoroughly by evaporation at elevated temperature under reduced pressure. The vial was then weighed to determine the yield of polymer product. The polymer product was then analyzed by rapid GPC, as described above to determine the molecular weight of the polymer produced, and by FTIR spectroscopy to determine the styrene incorporation. Results are presented in the tables 17–19.

TABLE 16

Description of array of polymerization experiments examples 13.A.1.–13.H.3.

|   | 1 | 2 | 3 | group 13 reagent[a] | group 13 reagent[b] |
|---|---|---|---|---|---|
| A | C 1 | C 1 | C 1 | 30 DIBAL | DIBAL |
| B | C 1 | C 1 |  | 10 DIBAL | DIBAL |
| C | C 1 | C 1 | C 1 | 10 TMA | TMA |
| D | C 3 | C 3 | C 3 | 10 DIBAL | DIBAL |

TABLE 16-continued

Description of array of polymerization experiments examples 13.A.1.–13.H.3.

|   | 1 | 2 | 3 | group 13 reagent[a] | group 13 reagent[b] |
|---|---|---|---|---|---|
| E | C 3 | C 3 | C 3 | 10 TMA | TMA |
| F | C 2 | C 2 | C 2 | 30 DIBAL | DIBAL |
| G | C 2 | C 2 | C 2 | 10 DIBAL | DIBAL |
| H | C 2 | C 2 | C 2 | 10 TMA | TMA |
| $t_1$ (min) | 10 | 10 | 0.8 | | |
| $t_2$ (min) | 0.5 | 0.5 | 0.5 | | |
| Injection Fraction | 0.2 | 0.2 | 0.2 | | |
| Premix Temp. (° C.) | 24 | 50 | 50 | | |
| Activator | ABF20 | ABF20 | ABF20 | | |

[a] Number of equivalents and identity of group 13 reagent added to Metal Complex as described in activation steps
[b] Group 13 reagent, which was placed in reaction vessel prior of catalyst injection (0.02 M solution was used).

TABLE 16A

Polymerization times in seconds for 13.A.1.–13.H.3.

|   | 1 | 2 | 3 |
|---|---|---|---|
| A | 601 | 602 | 444 |
| B | 601 | 601 | n.d. |
| C | 601 | 600 | 601 |
| D | 602 | 601 | 553 |
| E | 601 | 602 | 600 |
| F | 601 | 601 | 601 |
| G | 601 | 601 | 601 |
| H | 600 | 601 | 601 | n.d.: not determined

TABLE 17

Activity (mg polymer per minute per μmol) of examples 13.A.1.–13.H.3.

|   | 1 | 2 | 3 |
|---|---|---|---|
| A | 218 | 220 | 286 |
| B | 170 | 171 | n.d. |
| C | 132 | 134 | 154 |
| D | 197 | 193 | 240 |
| E | 145 | 151 | 166 |
| F | 209 | 215 | 217 |
| G | 174 | 176 | 193 |
| H | 144 | 147 | 151 | n.d.: not determined

TABLE 18

Styrene incorporation (mol %) of examples 13.A.1.–13.H.3.

|   | 1 | 2 | 3 |
|---|---|---|---|
| A | 2.4 | 3.0 | 3.0 |
| B | 3.0 | 3.8 | n.d. |
| C | 2.9 | 3.0 | 3.0 |
| D | 3.9 | 3.8 | 3.7 |
| E | 3.2 | 2.7 | 2.9 |
| F | 3.2 | 3.0 | 3.1 |
| G | 3.2 | 3.4 | 3.4 |
| H | 2.9 | 2.7 | 2.8 | n.d.: not determined

TABLE 19

Weight average molecular weight (k) of examples 13.A.1.–13.H.3.

|   | 1 | 2 | 3 |
|---|---|---|---|
| A | 228 | 241 | 247 |
| B | 386 | 371 | n.d. |
| C | 480 | 484 | 534 |
| D | 275 | 276 | 361 |
| E | 461 | 521 | 535 |
| F | 303 | 324 | 359 |
| G | 390 | 430 | 504 |
| H | 467 | 535 | 679 | n.d.: not determined

Example 14

Preparation of Ligand/Metal Compositions and Propylene Polymerization with Ligand/Metal Compositions Twenty-five polymerization reactions were carried out with different ligand/metal compositions, different temperatures, activators and activation conditions for the polymerization of propylene. Ligands L1–L5, whose structures and synthesis are shown above, are used in this example.

In situ preparation of metal-ligand compositions: Stock solutions were prepared as follows: The "metal precursor solution" is a 10 mM solution of Hf(NMe$_2$)$_4$ in toluene. The "ligand solutions" are 25 mM solutions of the representative ligands in toluene, prepared in an array of 1 mL glass vials by dispensing 0.030 mL of a 25 mM ligand solution in a 1 mL glass vial. To each 1 mL glass vial containing ligand/toluene solution was added 0.075 mL of the metal precursor solution (0.75 μmol), to form the metal-ligand combination solution. The reaction mixtures we allowed to sit at 80° C. for 2–3 hours during which time most of the solvent evaporates. The reaction mixtures were then dried completely by blowing a stream of Argon over the 1 mL vial. Prior to addition of alkylation and activator solution, a small amount of solvent (0.020 mL) was added to the dry composition.

Preparation of the polymerization reactor prior to injection of catalyst composition: This part of this example was performed as described in Example 11, above.

Preparation of the group 13 reagent and activator stock solutions: The "activator solution" is a 5 mM solution of N,N'-dimethylanilinium tetrakis (pentafluorophenyl) borate in toluene ("ABF20"). The solution is heated to approximately 85° C. to dissolve the reagent. The group 13 reagent solution is either a 0.2 M solution of diisobutylaluminium-hydride ("DIBAL") or a 0.2 M solution of triethylboron ("BEt3") or a solution which is 0.133 M in triethyl boron and 0.066M in diisobutyl aluminium hydride ("DIBAL/BEt3") or a solution which is 0.133 M in triethyl boron and 0.066M in triisobutylaluminium ("TIBA/BEt3").

Injection of solutions into the pressure reactor vessel: To the ligand metal composition, 0.030 mL of a 500 mM solution of 1-octene in toluene then 0.028 mL toluene and 0.112 mL of the group 13 reagent solution was added to the 1 mL vial. After 9 minutes, 0.165 mL (0.83 μmol) of the "activator solution" was added to the 1 mL vial. About another 30 seconds later, 0.044 mL of the 1 mL vial contents, followed immediately by 0.356 mL of toluene, were injected into the reaction vessel. The array of experiments is described in detail in table 20.

Propylene Polymerizations and Product work up: This part of this example was performed as described in Example 11, above, with specific polymerization times shown in table 20A. Results are presented in the tables 21–23.

TABLE 20

Description of array of polymerization experiments for examples 14.A.1.–14.D.6. and 14.E.1.

|   | 1 | 2 | 3 | 4 | 5 | 6 |
|---|---|---|---|---|---|---|
| A | L1 | L1 | L1 | L1 | L1 | L1 |
| B | L2 | L2 | L2 | L2 | L2 | L2 |
| C | L3 | L3 | L3 | L3 | L3 | L3 |
| D | L4 | L4 | L4 | L4 | L4 | L4 |
| E | L5 |   |   |   |   |   |
| Polym. Temp. (° C.) | 75 | 90 | 110 | 75 | 90 | 110 |
|   | 30 | 30 | 30 | 10/20 | 10/20 | 10/20 |
| group 13 reagent[a] | DIBAL | DIBAL | DIBAL | DIBAL/BEt3 | DIBAL/BEt3 | DIBAL/BEt3 |
| group 13 reagent[b] | DIBAL | DIBAL | DIBAL | BEt3 | BEt3 | BEt3 |
| Activator | ABF20 | ABF20 | ABF20 | ABF20 | ABF20 | ABF20 |

[a] Number of equivalents and identity of group 13 reagent added to ligand metal combination as described in activation steps.
[b] Group 13 reagent, which was placed in reaction vessel prior of catalyst injection (0.02 M solution was used).

TABLE 20A

Polymerization times in seconds of examples 14.A.1.–14.D.6. and 14.E.1.

|   | 1 | 2 | 3 | 4 | 5 | 6 |
|---|---|---|---|---|---|---|
| A | 263 | 138 | 901 | 250 | 160 | 215 |
| B | 578 | 253 | 901 | 522 | 372 | 901 |
| C | 783 | 233 | 821 | 521 | 341 | 244 |
| D | 363 | 335 | 901 | 341 | 243 | 262 |
| E | 409 |   |   |   |   |   |

TABLE 21

Activity (mg polymer per minute per μmol) of examples 14.A.1.–14.D.6. and 14.E.1.

|   | 1 | 2 | 3 | 4 | 5 | 6 |
|---|---|---|---|---|---|---|
| A | 710 | 635 | 41 | 900 | 786 | 256 |
| B | 103 | 290 | 43 | 101 | 153 | 37 |
| C | 92 | 344 | 67 | 268 | 215 | 227 |
| D | 204 | 181 | 41 | 677 | 339 | 198 |
| E | 652 |   |   |   |   |   |

TABLE 22

Crystallinity index of examples 14.A.1.–14.D.6. and 14.E.1.

|   | 1 | 2 | 3 | 4 | 5 | 6 |
|---|---|---|---|---|---|---|
| A | 0.73 | 0.71 | 0.72 | 0.72 | 0.70 | 0.73 |
| B | 0.71 | 0.67 | 0.66 | 0.66 | 0.64 | 0.66 |
| C | 0.76 | 0.70 | 0.70 | 0.70 | 0.65 | 0.68 |
| D | 0.80 | 0.77 | 0.79 | 0.78 | 0.76 | 0.80 |
| E | 0.76 | | | | | |

TABLE 23

Weight average molecular weight (k) of examples 14.A.1.–14.D.6. and 14.E.1.

|   | 1 | 2 | 3 | 4 | 5 | 6 |
|---|---|---|---|---|---|---|
| A | 554 | 279 | 90 | 878 | 567 | 158 |
| B | 891 | 438 | 109 | 668 | 582 | 112 |
| C | 1391 | 497 | 93 | 1136 | 488 | 95 |
| D | 803 | 489 | 106 | 980 | 661 | 149 |
| E | 463 | | | | | |

Example 15

Preparation of Ligand/Metal Compositions and Propylene Polymerization with Ligand/Metal Compositions Example 15.A.–15.F: Six polymerization reactions were carried out with different ligand/metal compositions for the polymerization of propylene. Preparation of the polymerization reactor prior to injection of catalyst composition, preparation of the stock solutions, propylene polymerizations and product work up were performed as in Example 14. The ligands that were used are L4, L5 and L29 described above.

In situ preparation of metal-ligand compositions: Stock solutions were prepared as follows: The "metal precursor solution" is a 10 mM solution of $Hf(NMe_2)_4$ in toluene or a 10 mM solution of $Zr(NMe_2)_4$. The "ligand solutions" are 25 mM solutions of the representative ligands in toluene, prepared in an array of 1 mL glass vials by dispensing 0.030 mL of a 25 mM ligand solution in a 1 mL glass vial. To each 1 mL glass vial containing ligand/toluene solution was added 0.075 mL of the metal precursor solution (0.75 µmol), to form the metal-ligand combination solution. The reaction mixtures we allowed to sit at 80° C. for 2–3 hours during which time most of the solvent evaporates. The reaction mixtures were dried completely by blowing a stream of Argon over the 1 mL vial. Prior to addition of alkylation and activator solution, a small amount of solvent (0.020 mL) was added to the dry composition.

Injection of solutions into the pressure reactor vessel: To the ligand metal composition, 0.037 mL of a 500 mM solution of 1-octene in toluene and 0.020 mL toluene and 0.112 mL of the group 13 reagent solution was added to the 1 mL vial. After 9 minutes, 0.165 mL (0.083 µmol) of the "activator solution" was added to the 1 mL vial. About another 30 seconds later, 0.090 mL of the 1 mL vial contents, followed immediately by 0.310 mL of toluene, were injected into the reaction vessel. The results are described in table 24.

Polymerization: The polymerization reaction was allowed to continue for the 155–600 seconds, during which time the temperature and pressure were maintained at their pre-set levels by computer control. The polymerization times were the lesser of the maximum desired polymerization reaction time or the time taken for a predetermined amount of monomer gas to be consumed in the polymerization reaction. The specific times for each polymerization are shown in table 24. After the reaction time elapsed, the reaction was quenched by addition of an overpressure of carbon dioxide.

Product work up: After the polymerization reaction, the glass vial insert, containing the polymer product and solvent, was removed from the pressure cell and removed from the inert atmosphere dry box, and the volatile components were removed using a centrifuge vacuum evaporator. After most of the volatile components had evaporated, the vial contents were dried thoroughly by evaporation at elevated temperature under reduced pressure. The vial was then weighed to determine the yield of polymer product. The polymer product was then analyzed by rapid GPC, as described above to determine the molecular weight of the polymer produced, and by FTIR spectroscopy to determine crystallinity. The results are described in table 24.

TABLE 24

Results of examples 15.A and 15.F

|   | Ligand | Temp. (° C.) | Metal precursor | Polym. time (sec) | Activity[a] | Cryst. Index[b] | Melting point (° C.) | % mmmm | Weight average MW (k) |
|---|---|---|---|---|---|---|---|---|---|
| A | L4 | 75 | $Hf(NMe_2)_4$ | 301 | 372 | 0.77 | 141 | 73 | 845 |
| B | L5 | 75 | $Hf(NMe_2)_4$ | 174 | 765 | 0.72 | 131 | 70 | 385 |
| C | L4 | 75 | $Zr(NMe_2)_4$ | 308 | 80 | 0.74 | 129 | nd | 682 |
| D | L5 | 75 | $Zr(NMe_2)_4$ | 218 | 255 | 0.65 | 118 | nd | 517 |
| E | L29 | 75 | $Hf(NMe_2)_4$ | 155 | 496 | 0.16 | nd | nd | 288 |
| F | L29 | 75 | $Zr(NMe_2)_4$ | 600 | 18 | 0.19 | nd | nd | 68 |

[a] Activity in mg polymer per minute per µmol;
[b] Crystallinity index by FTIR as described above
nd: not determined

Example 16

Ethylene/1-Octene Copolymerization

Ten polymerization reactions were carried out with metal complex C 21 described above at different activation conditions, for the copolymerization of ethylene and 1-octene.

Preparation of the polymerization reactor prior to injection of catalyst composition: A pre-weighed glass vial insert and disposable stirring paddle were fitted to each reaction vessel of the reactor. The reactor was then closed, 0.10 mL of a 0.02 M solution of group 13 reagents in toluene and 3.8 mL of toluene were injected into each pressure reaction vessel through a valve. The temperature was then set to 130° C. and the stirring speed was set to 800 rpm, and the mixture was exposed to ethylene at 100 psi pressure. An ethylene pressure of 100 psi in the pressure cell and the temperature setting were maintained, using computer control, until the end of the polymerization experiment. The identity of the of group 13 reagents is described in table 25.

Preparation of the group 13 reagent, activator stock solutions and metal complex solution: The "activator solution" is a 5 mM solution of N,N'-dimethylanilinium tetrakis (pentafluorophenyl) borate in toluene ("ABF20"). The solution is heated to approximately 85° C. to dissolve the reagent. The "group 13 reagent" solution is either a 0.20 M solution of triisobutylaluminium ("TIBA") or 0.20 M solution of triethylaluminium ("TEAL") or a 0.20 M solution of trimethylaluminium ("TMA") or 0.20 M solution of diisobutylaluminiumhydride ("DIBAL") or a 0.20 M solution of triethylboron ("BEt$_3$"), all "group 13 reagent" solutions were solutions in toluene. The metal complex solution is 5 mM solution of C21 in toluene (27.5 mg of C21 dissolved in 6.4 mL toluene).

Activation and Injection of solutions into the pressure reactor vessel: First, 0.016 mL of a 0.5 M solution of 1-octene in toluene was dispensed into a 1 mL vial. Then, 0.060 mL (1.2 µmol) of the group 13 reagent solution was dispensed into the 1 mL vial as specified in the table 25. Then, 0.080 ml (0.4 µmol) of the metal complex solution (5 mM in toluene) followed by 0.020 ml toluene was added to the 1 mL vial. After around 9 min, 0.420 mL 1-octene, followed immediately by 0.380 mL of toluene were injected into the reaction vessel. After another 30 seconds, 0.088 mL (0.44 µmol) of the "activator solution" was added to the 1 mL vial. After 30 seconds elapsed, a fraction of the total 1 mL vial contents (listed in table 25 as Catalyst injection fraction), followed immediately by approximately 0.7 mL of toluene, were injected into the reaction vessel. The array of experiments with values for equivalents and identity of group 13 reagent and injection fractions is described in table 25.

Polymerization: The polymerization reaction was allowed to continue for the time shown in table 25A, during which time the temperature and pressure were maintained at their pre-set levels by computer control. The polymerization times were the lesser of the maximum desired polymerization reaction time or the time taken for a predetermined amount of monomer gas to be consumed in the polymerization reaction. After the reaction time elapsed, the reaction was quenched by addition of an overpressure of carbon dioxide sent to the reactor.

Product work up: ethylene/1-octene copolymerizations After the polymerization reaction, the glass vial insert, containing the polymer product and solvent, was removed from the pressure cell and removed from the inert atmosphere dry box, and the volatile components were removed using a centrifuge vacuum evaporator. After most of the volatile components had evaporated, the vial contents were dried thoroughly by evaporation at elevated temperature under reduced pressure. The vial was then weighed to determine the yield of polymer product. The polymer product was then analyzed by rapid GPC, as described above to determine the molecular weight of the polymer produced, and by FTIR spectroscopy to determine 1-octene incorporation. Results are presented in Table 26–28.

TABLE 25

Description of array of polymerization experiments for examples 16.A.1.–16.E.2.

|  | 1 | 2 | group 13 reagent[a] | group 13 reagent[b] |
|---|---|---|---|---|
| Polymerization temp (° C.) | 130 | 130 |  |  |
| A | C 21 | C 21 | 30 TIBA | TIBA |
| B | C 21 | C 21 | 30 DIBAL | DIBAL |
| C | C 21 | C 21 | 30 TMA | TMA |
| D | C 21 | C 21 | 30 TEAL | TEAL |
| E | C 21 | C 21 | 30 BEt$_3$ | BEt$_3$ |
| Catalyst injection fraction | 0.5 | 0.25 |  |  |
| Activator | ABF20 | ABF20 |  |  |

[a] Number of equivalents and identity of group 13 reagent added to ligand metal combination as described in activation steps.
[b] Group 13 reagent, which was placed in reaction vessel prior of catalyst injection (0.02 M solution was used).

TABLE 25A

Polymerization times in seconds of examples 16.A.1.–16.E.2.

|  | 1 | 2 |
|---|---|---|
| A | 350 | 457 |
| B | 278 | 349 |
| C | 311 | 457 |
| D | 169 | 466 |
| E | 601 | 600 |

TABLE 26

Activity (mg polymer per minute per µmol) of examples 16.A.1.–16.E.2.

|  | 1 | 2 |
|---|---|---|
| A | 242 | 338 |
| B | 339 | 492 |
| C | 278 | 322 |
| D | 466 | 307 |
| E | 112 | 126 |

TABLE 27 wt % Octene incorporation of examples 16.A.1.–16.E.2.

|  | 1 | 2 |
|---|---|---|
| A | 38 | 32 |
| B | 40 | 36 |
| C | 38 | 33 |
| D | 32 | 33 |
| E | 43 | 37 |

TABLE 28

Weight average molecular weight (k) of examples 16.A.1.–16.E.2.

|  | 1 | 2 |
|---|---|---|
| A | 51 | 71 |
| B | 50 | 67 |
| C | 58 | 78 |
| D | 50 | 72 |
| E | 380 | 793 |

Example 17

Propylene Polymerization Using Metal Complex 7, 8, 9, 10 at Different Polymerization Temperatures In this example, thirty-one polymerization reactions were carried out. The reactor was prepared as in Example 11, above. In addition, the polymerization was run in the same manner and the polypropylene polymer was worked up in the same manner as in Example 11, above.

Preparation of the polymerization reactor prior to injection of catalyst composition: This part of this example was performed as described in Example 11, above.

Preparation of the group 13 reagent and activator stock solutions: The "activator solution" is a 5 mM solution of N,N'-dimethylanilinium tetrakis (pentafluorophenyl) borate in toluene ("ABF20"). The solution is heated to approximately 85° C. to dissolve the reagent. The "group 13 reagent" solution is either a 0.2 M solution of diisobutyla-luminiumhydride ("DIBAL") or a 0.2 M solution of trimethylaluminium ("TMA"). All "group 13 reagent" solutions were solutions in toluene.

Activation and Injection of solutions into the pressure reactor vessel: First, an appropriate amount of the 0.2 M group 13 reagent solution was dispensed into a 1 mL vial as specified in the table 29.0.100 mL (0.4 μmol) of the metal complex solution (4 mM in toluene) was added to the 1 mL vial. This mixture was held at at ambient temperature for a time period of $t_1$ as indicated in table 29. Then, 0.088 mL (0.44 μmol) of the "activator solution" was added to the 1 mL vial. After the time period $t_2$ elapsed (time listed in table 29), a fraction of the total 1 mL vial contents (listed in table 29), followed immediately by approximately 0.3 mL of toluene, were injected into the reaction vessel. The array of experiments with values for equivalents of group 13 reagent, $t_1$, $t_2$ and injection fraction is described in table 29.

Polymerization: The polymerization reaction was allowed to continue for the time shown in table 29A, during which time the temperature and pressure were maintained at their pre-set levels by computer control. The polymerization times were the lesser of the maximum desired polymerization reaction time or the time taken for a predetermined amount of monomer gas to be consumed in the polymerization reaction. After the reaction time elapsed, the reaction was quenched by addition of an overpressure of carbon dioxide sent to the reactor.

Product work up: Propylene Polymerizations: This part of this example was performed as described in Example 11, above. The results are presented in tables 30–32.

TABLE 29

Description of polymerization experiments using complexes 7–10 (examples 17.A.1–17.H.3):

|   | 1 | 2 | 3 | 4 | group 13 reagent[a] | group 13 reagent[b] |
|---|---|---|---|---|---|---|
| A | C7 | C7 | C7 | C7 | 30 | DIBAL |
| B | C7 | C7 | C7 | C7 | 10 | DIBAL |
| C | C8 | C8 | C8 | C8 | 30 | DIBAL |
| D | C8 | C8 | C8 | C8 | 10 | DIBAL |
| E | C9 | C9 | C9 | C9 | 30 | DIBAL |
| F | C9 | C9 | C9 | C9 | 10 | DIBAL |
| G | C10 | C10 | C10 | C10 | 30 | DIBAL |
| H | C10 | C10 | C10 |  | 10 | DIBAL |
| $t_1$ (min) | 10 | 10 | 10 | 10 | | |
| $t_2$ (min) | 0.5 | 0.5 | 0.5 | 0.5 | | |
| Injection Fraction | 0.15 | 0.15 | 0.15 | 0.45 | | |
| Polym. Temp. (° C.) | 90 | 90 | 110 | 130 | | |
| group 13 reagent[c] | DIBAL | TMA | DIBAL | DIBAL | | |
| Activator | ABF20 | ABF20 | ABF20 | ABF20 | | |

[a] Number of equivalents of group 13 reagent added to Metal Complex as described in activation steps
[b] Group 13 reagent, which was placed in reaction vessel prior of catalyst injection (0.02M solution was used).
[c] Identity of group 13 reagent added to Metal Complex as described in activation steps

TABLE 29A

Polymerization times in seconds for examples 17.A1.–17.H.3.

|   | 1 | 2 | 3 | 4 |
|---|---|---|---|---|
| A | 346 | 178 | 288 | 661 |
| B | 291 | 150 | 341 | 900 |
| C | 272 | 145 | 266 | 902 |
| D | 251 | 141 | 367 | 902 |
| E | 159 | 182 | 170 | 383 |
| F | 159 | 157 | 195 | 528 |
| G | 172 | 169 | 201 | 204 |
| H | 179 | 155 | 196 |  |

TABLE 30

Activity (mg polymer per minute per μmol) of examples 17.A.1.–17.H.3.

|   | 1 | 2 | 3 | 4 |
|---|---|---|---|---|
| A | 316 | 1020 | 320 | 49 |
| B | 416 | 1287 | 277 | 32 |
| C | 399 | 1254 | 348 | 19 |
| D | 489 | 1496 | 240 | 21 |
| E | 989 | 1016 | 624 | 78 |
| F | 1006 | 1304 | 524 | 55 |
| G | 848 | 1250 | 518 | 145 |
| H | 754 | 1495 | 507 |  |

TABLE 31

Crystallinity index of examples 17.A.1.–17.H.3.

|   | 1 | 2 | 3 | 4 |
|---|---|---|---|---|
| A | 0.91 | 0.87 | 0.84 | 0.88 |
| B | 0.88 | 0.88 | 0.89 | 0.89 |
| C | 0.86 | 0.82 | 0.84 | 0.83 |
| D | 0.85 | 0.82 | 0.84 | 0.86 |
| B | 0.86 | 0.86 | 0.86 | 0.88 |
| F | 0.85 | 0.83 | 0.84 | 0.87 |
| G | 0.83 | 0.86 | 0.86 | 0.91 |
| H | 0.87 | 0.87 | 0.85 |      |

TABLE 32

Weight average molecular weight (k) of examples 17.A.1.–17.H.3.

|   | 1 | 2 | 3 | 4 |
|---|---|---|---|---|
| A | 536 | 350 | 161 | 32 |
| B | 552 | 310 | 175 | 50 |
| C | 579 | 422 | 218 | 44 |
| D | 859 | 345 | 231 | 56 |
| E | 404 | 299 | 177 | 40 |
| F | 525 | 368 | 206 | 46 |
| G | 425 | 336 | 154 | 33 |
| H | 604 | 361 | 186 | 3 |

Example 18

Propylene Polymerization Using Metal Complex 11 (C 11) at Different Activation Methods In this example, sixteen polymerization reactions were carried out. The reactor was prepared as in Example 11, above. In addition, the polymerization was run in the same manner and the polypropylene polymer was worked up in the same manner as in Example 11, above.

Preparation of the polymerization reactor prior to injection of catalyst composition: This part of this example was performed as described in Example 11, above.

Preparation of the group 13 reagent and activator stock solutions: The "activator solution" is a 2.5 mM solution of N,N'-dimethylanilinium tetrakis (pentafluorophenyl) borate in toluene ("ABF20"). The solution is heated to approximately 85° C. to dissolve the reagent. The "group 13 reagent" solution is either a 0.05 M solution of triisobutylaluminium ("TIBA") or 0.05 M solution of triethylaluminium ("TEAL") or a 0.05 M solution of trimethylaluminium ("TMA") or 0.05 M solution of diisobutylaluminiumhydride ("DIBAL") or a 0.05 M solution of Akzo PMAO-IP ("PMAO") or 0.05M of Akzo MMAO-3A ("MMAO"), all "group 13 reagent" solutions were solutions in toluene.

Activation and Injection of solutions into the pressure reactor vessel: First, an appropriate amount of the 0.05 M group 13 reagent solution was dispensed into a 1 mL vial that was kept at a constant premix temperature as specified in the table 33. Then, 0.100 mL (0.25 μmol) of the metal complex solution (2.5 mM in toluene) was added to the 1 mL vial. This mixture was held at a premix temperature for a time period of $t_1$ as indicated in table 33. Then, 0.110 mL (0.275 μmol) of the "activator solution" was added to the 1 mL vial. After the time period $t_2$ elapsed, a fraction of the total 1 mL vial content, followed immediately by approximately 0.3 mL of toluene, were injected into the reaction vessel. The array of experiments with values for equivalents of group 13 reagent, $t_1$, $t_2$ and injection fraction is described in table 33.

Polymerization: The polymerization reaction was allowed to continue for the time shown in table 33A, during which time the temperature and pressure were maintained at their pre-set levels by computer control. The polymerization times were the lesser of the maximum desired polymerization reaction time or the time taken for a predetermined amount of monomer gas to be consumed in the polymerization reaction. After the reaction time elapsed, the reaction was quenched by addition of an overpressure of carbon dioxide sent to the reactor.

Product work up: Propylene Polymerizations: This part of this example was performed as described in Example 11, above. The results are presented in tables 34–36.

The array of experiments is described in table 33. The specific times for each polymerization are shown in table 33a. The results are presented in tables 34–36.

TABLE 33

Description of polymerization experiments using complex 11 (examples 18.A.1–18.H.2):

|   | 1 | 2 | group 13 reagent[a] | group 13 reagent[b] |
|---|---|---|---|---|
| A | C 11 | C 11 | 6 TIBA | TIBA |
| B | C 11 | C 11 | 6 TEAL | TEAL |
| C | C 11 | C 11 | 6 TMA | TMA |
| D | C 11 | C 11 | 10 TMA | TMA |
| E | C 11 | C 11 | 6 DIBAL | DIBAL |
| F | C 11 | C 11 | 10 DIBAL | DIBAL |
| G | C 11 | C 11 | 6 PMAO-IP | PMAO-IP |
| H | C 11 | C 11 | 6 MMAO | MMAO |
| Injection Fraction | 0.132 | 0.132 | | |
| Polym. Temp. (° C.) | 110 | 110 | | |
| $T_1$ (min) | 10 | 0.5 | | |
| $T_2$ (min) | 0.5 | 0.5 | | |
| Premix Temp. (° C.) | 25 | 25 | | |
| Activator | ABF20 | ABF20 | | |

[a]Number of equivalents and identity of group 13 reagent added to Metal Complex as described in activation steps
[b]Group 13 reagent, which was placed in reaction vessel prior of catalyst injection (0.02 M solution was used).

TABLE 33A

Polymerization times in seconds for examples 18.A.1.–18.H.2.

|   | 1 | 2 |
|---|---|---|
| A | 241 | 279 |
| B | 236 | 199 |
| C | 263 | 226 |
| D | 303 | 223 |
| E | 257 | 601 |
| F | 242 | 601 |
| G | 199 | 231 |
| H | 232 | 186 |

TABLE 34

Activity (mg polymer per minute per μmol) of examples 18.A.1.–18.H.2.

|   | 1 | 2 |
|---|---|---|
| A | 782 | 577 |
| B | 741 | 959 |
| C | 663 | 794 |
| D | 533 | 831 |
| E | 714 | 224 |
| F | 714 | 160 |
| G | 930 | 842 |
| H | 741 | 1050 |

TABLE 35

Crystallinity index of examples 18.A.1.–18.H.2.

| | 1 | 2 |
|---|---|---|
| A | 0.87 | 0.88 |
| B | 0.87 | 0.87 |
| C | 0.87 | 0.86 |
| D | 0.86 | 0.88 |
| E | 0.89 | 0.85 |
| F | 0.87 | 0.84 |
| G | 0.89 | 0.81 |
| H | 0.88 | 0.84 |

TABLE 36

Weight average molecular weight (k) of examples 18.A.1.–18.H.2.

| | 1 | 2 |
|---|---|---|
| A | 80 | 81 |
| B | 86 | 94 |
| C | 101 | 105 |
| D | 101 | n.d. |
| E | 77 | n.d. |
| F | 75 | 70 |
| G | 109 | n.d. |
| H | 107 | 106 | n.d. not determined

Example 19

Propylene Polymerization Using Metal Complex 1, 2, 9, 12, 13, 14, 15 and 16

In this example, eight polymerization reactions were carried out. The reactor was prepared as in Example 11, above.

Preparation of the polymerization reactor prior to injection of catalyst composition: This part of this example was performed as described in Example 11, above.

Preparation of the group 13 reagent and activator stock solutions: The "activator solution"is a 5 mM solution of N,N'-dimethylanilinium tetrakis (pentafluorophenyl) borate in toluene ("ABF20"). The solution is heated to approximately 85° C. to dissolve the reagent. The "group 13 reagent" solution a 0.2 M solution of trimethylaluminium ("TMA"), all "group 13 reagent" solutions were solutions in toluene.

Activation and Injection of solutions into the pressure reactor vessel: First, 0.120 mL (0.6 μmol) of the metal complex solution (5 mM in toluene) was added to the 1 mL vial. Then, 0.012 ml of a 0.5 M solution of 1-octene intoluene followed by 0.090 ml of the 0.2 M group 13 reagent solution was dispensed into a 1 mL as specified in the table 37. This mixture was held for a time period of $t_1$ as indicated in table 37. Then, 0.132 mL (0.66 μmol) of the "activator solution" was added to the 1 mL vial. After the time period $t_2$ elapsed (time listed in table 37), a fraction of the total 1 mL vial contents (listed in table 37), followed immediately by approximately 0.3 mL of toluene, were injected into the reaction vessel. The array of experiments with values for equivalents of group 13 reagent, $t_1$, $t_2$ and injection fraction is described in table 37.

Polymerization: The polymerization reaction was allowed to continue for the time shown in table 37A, during which time the temperature and pressure were maintained at their pre-set levels by computer control. The polymerization times were the lesser of the maximum desired polymerization reaction time or the time taken for a predetermined amount of monomer gas to be consumed in the polymerization reaction. After the reaction time elapsed, the reaction was quenched by addition of an overpressure of carbon dioxide sent to the reactor.

Product work up: Propylene Polymerizations: This part of this example was performed as described in Example 11, above. The results are presented in tables 38–40.

TABLE 37

Description of polymerization experiments using complexes 1, 2, 9, 12, 13, 14, 15 and 16 (examples 19.A.1–19.H.1):

| | 1 | Group 13 reagent[b] |
|---|---|---|
| A | C 13 | TMA |
| B | C 14 | TMA |
| C | C 15 | TMA |
| D | C 16 | TMA |
| E | C 12 | TMA |
| F | C 9 | TMA |
| G | C 1 | TMA |
| H | C 2 | TMA |
| Injection Fraction | 0.10 | |
| Polym. Temp. (° C.) | 110 | |
| Group 13 reagent[a] | 30 TMA | |
| $t_1$ (min) | 10 | |
| $t_2$ (min) | 0.5 | |
| Activator | ABF20 | |

[a] Number of equivalents and identity of group 13 reagent added to Metal Complex as described in activation steps
[b] Group 13 reagent, which was placed in reaction vessel prior of catalyst injection (0.02 M solution was used).

TABLE 37A

Polymerization times in seconds for examples 19.A.1–19.H.1.

| | 1 |
|---|---|
| A | 431 |
| B | 224 |
| C | 900 |
| D | 900 |
| E | 94 |
| F | 174 |
| G | 165 |
| H | 86 |

TABLE 38

Activity (mg polymer per minute per μmol) of examples 19.A.1–19.H.1.

| | 1 |
|---|---|
| A | 230 |
| B | 716 |
| C | 79 |
| D | 47 |
| E | 2511 |
| F | 825 |
| G | 779 |
| H | 1466 |

TABLE 39

Crystallinity index of examples 19.A.1–19.H.1.

| | 1 |
|---|---|
| A | 0.38 |
| B | 0.56 |
| C | 0.53 |
| D | 0.30 |

TABLE 39-continued

Crystallinity index of examples 19.A.1–19.H.1.

| | 1 |
|---|---|
| E | 0.92 |
| F | 0.91 |
| G | 0.88 |
| H | 0.88 |

TABLE 40

Weight average molecular weight (k) of examples 19.A.1–19.H.1.

| | 1 |
|---|---|
| A | 64 |
| B | 94 |
| C | 67 |
| D | 76 |
| E | 86 |
| F | 100 |
| G | 90 |
| H | 89 |

Example 20

Propylene Polymerization Using Metal Complexes 9 and 12 at Different Polymerization Temperatures In this example, four polymerization reactions were carried out.

Preparation of the polymerization reactor prior to injection of catalyst composition: This part of this example was performed as described in Example 11, above.

Preparation of the group 13 reagent and activator stock solutions: The "activator solution" is a 5 mM solution of N,N'-dimethylanilinium tetrakis (pentafluorophenyl) borate in toluene ("ABF20"). The solution is heated to approximately 85° C. to dissolve the reagent. The "group 13 reagent" solution a 0.2 M solution of diisobutylaluminium-hydride ("DIBAL"), all "group 13 reagent" solutions were solutions in toluene.

Activation and Injection of solutions into the pressure reactor vessel: First, an appropriate amount of the 0.2 M group 13 reagent solution was dispensed into a 1 mL vial as specified in the table 41. 0.120 mL (0.6 µmol) of the metal complex solution (5 mM in toluene) was added to the 1 mL vial. This mixture was held at a premix temperature for a time period of $t_1$ as indicated in table 41. Then, 0.132 mL (0.66 µmol) of the "activator solution" was added to the 1 mL vial. After the time period $t_2$ elapsed (time listed in table 41), a fraction of the total 1 mL vial contents (listed in table 41), followed immediately by approximately 0.3 mL of toluene, were injected into the reaction vessel. The array of experiments with values for equivalents of group 13 reagent, t1, t2 and injection fraction is described in table 41.

Polymerization: The polymerization reaction was allowed to continue for 120–900 seconds, during which time the temperature and pressure were maintained at their pre-set levels by computer control. The specific times for each polymerization are shown in table 41a. After the reaction time elapsed, the reaction was quenched by addition of an overpressure of carbon dioxide sent to the reactor.

Product work up: Propylene Polymerizations: This part of this example was performed as described in Example 11, above. The results are presented in tables 42–45

TABLE 41

Description of polymerization experiments using complexes 9 and 12 (examples 20.A.1–20.B.2):

| | 1 | 2 | group 13 reagent[a] | group 13 reagent[b] |
|---|---|---|---|---|
| A | C 9 | C 9 | 30 DIBAL | DIBAL |
| B | C 12 | C 12 | 30 DIBAL | DIBAL |
| Injection Fraction | 0.075 | 0.20 | | |
| Polym. Temp. (° C.) | 110 | 130 | | |
| $T_1$ (min) | 10 | 10 | | |
| $T_2$ (min) | 0.5 | 0.5 | | |
| Activator | ABF20 | ABF20 | | |

[a]Number of equivalents and identity of group 13 reagent added to Metal Complex as described in activation steps
[b]Group 13 reagent, which was placed in reaction vessel prior of catalyst injection (0.02M solution was used).

TABLE 41A

Polymerization times in seconds for examples 20.A.1–20.B.2

| | 1 | 2 |
|---|---|---|
| A | 215 | 900 |
| B | 120 | 901 |

TABLE 42

Activity (mg polymer per minute per µmol) of examples 20.A.1–20.B.2

| | 1 | 2 |
|---|---|---|
| A | 603 | 37 |
| B | 1232 | 49 |

TABLE 43

Crystallinity index of examples 20.A.1–20.B.2

| | 1 | 2 |
|---|---|---|
| A | 0.86 | 0.86 |
| B | 0.83 | 0.78 |

TABLE 44

Melting points of examples (in ° C.) 20.A.1–20.B.2

| | 1 | 2 |
|---|---|---|
| A | 145/152 | 138/147 |
| B | 137/144 | 133/141 |

Bimodal melting points observed

TABLE 45

Weight average molecular weight (k) of examples 20.A.1–29.B.2

| | 1 | 2 |
|---|---|---|
| A | 94 | 26 |
| B | 59 | 15 |

Example 21

Preparation of Ligand/Metal Compositions and Propylene Polymerization with Ligand/Metal Compositions Twenty-four polymerization reactions were carried out with different ligand/metal compositions, different temperatures, activators and activation conditions for the polymerization of propylene. Ligands 6–13, whose structures and synthesis are shown above, are used in this example.

In situ preparation of metal-ligand compositions: This part of this example was performed as described in Example 14, above.

Preparation of the polymerization reactor prior to injection of catalyst composition: This part of this example was performed as described in Example 11, above.

Preparation of the group 13 reagent and activator stock solutions: The "activator solution" is a 5 mM solution of N,N'-dimethylanilinium tetrakis (pentafluorophenyl) borate in toluene ("ABF20"). The solution is heated to approximately 85° C. to dissolve the reagent. The group 13 reagent solution is a 0.2 M solution of diisobutylaluminiumhydride ("DIBAL").

Injection of solutions into the pressure reactor vessel: To the ligand metal composition, 0.030 mL of a 500 mM solution of 1-octene in toluene and 0.028 ml of toluene and 0.112 mL of the group 13 reagent solution was added to the 1 mL vial. After 9 minutes, 0.165 mL (0.83 μmol) of the "activator solution" was added to the 1 mL vial. About another 30 seconds later, a fraction of the total 1 mL vial contents (listed in table 46 as Injection fractio), followed immediately by approximately 0.3 mL of toluene, were injected into the reaction vessel. The array of experiments is described in detail in table 46.

Propylene Polymerizations and Product work up: This part of this example was performed as described in Example 11, above, with specific polymerization times shown in table 51A. Results are presented in the tables 47–50.

Propylene Polymerizations and Product work up: This part of this example was performed as described in Example 11, above, with specific polymerization times shown in table 46A. Results are presented in the tables 47–50.

TABLE 46

Description of array of polymerization experiments for examples 21.A.1.–21.H.3.

|   | 1 | 2 | 3 |
|---|---|---|---|
| A | L10 | L10 | L10 |
| B | L11 | L11 | L11 |
| C | L12 | L12 | L12 |
| D | L13 | L13 | L13 |
| E | L6 | L6 | L6 |
| F | L7 | L7 | L7 |
| G | L8 | L8 | L8 |
| H | L9 | L9 | L9 |
| group 13 reagent[a] | 30 DIBAL | 30 DIBAL | 30 DIBAL |
| group 13 reagent[b] | DIBAL | DIBAL | DIBAL |
| Activator | ABF20 | ABF20 | ABF20 |
| Polym. Temp (° C.): | 90 | 110 | 130 |
| Injection fraction | 0.086 | 0.13 | 0.26 |

[a] Number of equivalents and identity of group 13 reagent added to ligand metal combination as described in activation steps.
[b] Group 13 reagent, which was placed in reaction vessel prior of catalyst injection (0.02M solution was used).

TABLE 46A

Polymerization times in seconds of examples 21.A.1.–21.H.3.

|   | 1 | 2 | 3 |
|---|---|---|---|
| A | 901 | 901 | 901 |
| B | 900 | 901 | 901 |
| C | 900 | 901 | 900 |
| D | 901 | 901 | 901 |
| E | 252 | 327 | 901 |
| F | 359 | 902 | 901 |
| G | 288 | 287 | 900 |
| H | 155 | 229 | 900 |

TABLE 47

Activity (mg polymer per minute per μmol) of examples 21.A.1.–21.H.3.

|   | 1 | 2 | 3 |
|---|---|---|---|
| A | 12 | 3 | 1 |
| B | 10 | 2 | 1 |
| C | 1 | 1 | 0 |
| D | 23 | 6 | 2 |
| E | 429 | 158 | 18 |
| F | 250 | 50 | 10 |
| G | 329 | 191 | 15 |
| H | 853 | 258 | 20 |

TABLE 48

Crystallinity index of examples 21.A.1.–21.H.3.

|   | 1 | 2 | 3 |
|---|---|---|---|
| A | n.d. | n.d. | n.d. |
| B | n.d. | n.d. | n.d. |
| C | n.d. | n.d. | n.d. |
| D | 0.74 | n.d. | n.d. |
| E | 0.85 | 0.84 | 0.81 |
| F | 0.89 | 0.84 | 0.86 |
| G | 0.84 | 0.87 | 0.82 |
| H | 0.80 | 0.86 | 0.84 | n.d. = not determined

TABLE 49

Weight average molecular weight (k) of examples 21.A.1.–21.H.3.

|   | 1 | 2 | 3 |
|---|---|---|---|
| A | n.d. | n.d. | n.d. |
| B | n.d. | n.d. | n.d. |
| C | n.d. | n.d. | n.d. |
| D | 310 | n.d. | n.d. |
| E | 681 | 165 | 30 |
| F | 537 | 106 | 19 |
| G | 560 | 124 | 25 |
| H | 458 | 124 | 26 | n.d. = not determined

TABLE 50

Melting points of selected examples (in ° C.) 21.E.1., 21.F.1. and 21.H.1.

|   | 1 | 2 | 3 |
|---|---|---|---|
| A |   |   |   |
| B |   |   |   |
| C |   |   |   |

TABLE 50-continued

Melting points of selected examples (in ° C.) 21.E.1., 21.F.1. and 21.H.1.

|   | 1 | 2 | 3 |
|---|---|---|---|
| D |   |   |   |
| E | 142/147 |   |   |
| F | 148 |   |   |
| G |   |   |   |
| H | 146 |   |   |

Bimodal melting points detected

Example 22

Preparation of Ligand/Metal Compositions and Propylene Polymerization with Ligand/Metal Compositions Eighteen polymerization reactions were carried out with different ligand/metal compositions, different temperatures, activators and activation conditions for the polymerization of propylene. Ligands L14–L19, whose structures and synthesis are shown above, are used in this example.

In situ preparation of metal-ligand compositions: This part of this example was performed as described in Example 14, above.

Preparation of the polymerization reactor prior to injection of catalyst composition: This part of this example was performed as described in Example 11, above.

Preparation of the group 13 reagent and activator stock solutions: The "activator solution" is a 5 mM solution of N,N'-dimethylanilinium tetrakis pentafluorophenyl) borate in toluene ("ABF20"). The solution is heated to approximately 85° C. to dissolve the reagent. The group 13 reagent solution is a 0.2 M solution of diisobutylaluminiumhydride ("DIBAL").

Injection of solutions into the pressure reactor vessel: To the ligand metal composition, 0.030 mL of a 500 mM solution of 1-octene in toluene and 0.112 mL of the group 13 reagent solution was added to the 1 mL vial. After 9 minutes, 0.165 mL (0.83 µmol) of the "activator solution" was added to the 1 mL vial. About another 30 seconds later, a fraction of the total 1 mL vial contents (listed in table 51), followed immediately by approximately 0.3 mL of toluene, were injected into the reaction vessel. The array of experiments is described in detail in table 51.

Propylene Polymerizations and Product work up: This part of this example was performed as described in Example 11, above, with specific polymerization times shown in table 51A. Results are presented in the tables 52–55.

TABLE 51

Description of array of polymerization experiments for examples 22.A.1.–22.F.3.

|   | 1 | 2 | 3 |
|---|---|---|---|
| A | L14 | L14 | L14 |
| B | L15 | L15 | L15 |
| C | L16 | L16 | L16 |
| D | L17 | L17 | L17 |
| E | L18 | L18 | L18 |
| F | L19 | L19 | L19 |
| Polym. Temp (° C.): | 90 | 110 | 130 |
| group 13 reagent[a] | 30 DIBAL | 30 DIBAL | 30 DIBAL |
| group 13 reagent[b] | DIBAL | DIBAL | DIBAL |

TABLE 51-continued

Description of array of polymerization experiments for examples 22.A.1.–22.F.3.

|   | 1 | 2 | 3 |
|---|---|---|---|
| Activator | ABF20 | ABF20 | ABF20 |
| Injection fraction | 0.065 | 0.13 | 0.26 |

[a] Number of equivalents and identity of group 13 reagent added to ligand metal combination as described in activation steps.
[b] Group 13 reagent, which was placed in reaction vessel prior of catalyst injection (0.02 M solution was used).

TABLE 51A

Polymerization times in seconds of examples 22.A.1.–22.F.3.

|   | 1 | 2 | 3 |
|---|---|---|---|
| A | 900 | 902 | 901 |
| B | 901 | 901 | 900 |
| C | 224 | 290 | 901 |
| D | n.d. | 902 | 901 |
| E | 518 | 901 | 901 |
| F | 538 | 901 | 901 | n.d. = not determined

TABLE 52

Activity (mg polymer per minute per µmol) of examples 22.A.1.–22.F.3.

|   | 1 | 2 | 3 |
|---|---|---|---|
| A | 2 | 1 | 1 |
| B | 9 | 2 | 1 |
| C | 556 | 188 | 14 |
| D | n.d. | 1 | 1 |
| E | 203 | 33 | 6 |
| F | 195 | 21 | 6 | n.d. = not determined

TABLE 53

Crystallinity index of examples examples 22.A.1.–22.F.3.

|   | 1 | 2 | 3 |
|---|---|---|---|
| A | n.d. | n.d. | n.d. |
| B | n.d. | n.d. | n.d. |
| C | 0.48 | 0.52 | 0.47 |
| D | n.d. | n.d. | n.d. |
| E | 0.54 | 0.56 | n.d. |
| F | 0.60 | 0.61 | n.d. | n.d. = not determined

TABLE 54

Weight average molecular weight (k) of examples 22.A.1.–22.F.3.

|   | 1 | 2 | 3 |
|---|---|---|---|
| A | n.d. | n.d. | n.d. |
| B | n.d. | n.d. | n.d. |
| C | 334 | 97 | 18 |
| D | n.d. | n.d. | n.d. |
| E | 229 | 62 | n.d. |
| F | 248 | 46 | n.d. | n.d. = not determined

TABLE 55

Melting points (in ° C.) of selected examples for 22.A.1.–22.F.3.

|   | 1 | 2 | 3 |
|---|---|---|---|
| A |   |   |   |
| B |   |   |   |
| C | 118 |   |   |
| D |   |   |   |
| E | 130/139 |   |   |
| F | 134/141 |   |   |

Bimodal melting points detected

Example 23

Ethylene-Styrene Copolymerization Using Metal Complexes 7, 8, 9 and 10 (C7, C8, C9, C10) at Different Activation Conditions Twenty-four polymerization reactions were run with different metal complexes, temperatures, activators and activating conditions for copolymerization of ethylene and styrene.

Preparation of the polymerization reactor prior to injection of catalyst composition: A pre-weighed glass vial insert and disposable stirring paddle were fitted to each reaction vessel of the reactor. The reactor was then closed, 0.10 mL of a 0.02 M group 13 reagent solution in toluene and 3.8 mL of toluene were injected into each pressure reaction vessel through a valve. The identity of the group 13 reagent solution is given in table 56. The temperature was then set to the appropriate polymerization temperature (as described in table 56), and the stirring speed was set to 800 rpm, and the mixture was exposed to ethylene at 100 psi pressure. An ethylene pressure of 100 psi in the pressure cell and the temperature setting were maintained, using computer control, until the end of the polymerization experiment.

Preparation of the group 13 reagent and activator stock solutions: The "activator solution" is a 5 mM solution of N,N'-dimethylanilinium tetrakis (pentafluorophenyl) borate in toluene ("ABF20"). The solution is heated to approximately 85° C. to dissolve the reagent. The group 13 reagent solution is either a 0.2 M solution of diisobutylaluminium-hydride ("DIBAL") or a 0.2 M solution of trimethylaluminium ("TMA"), both in toluene.

Activation and Injection of solutions into the pressure reactor vessel: First, an appropriate amount of the 0.2 M group 13 reagent solution was dispensed in a 1 mL vial which was kept at a constant premix temperature as specified in the table 56. Then 0.100 mL of the metal complex solution (4 mM in toluene) was added. This mixture was held at a premix temperature for a time $t_1$ as indicated in table 56, during which time, 0.420 mL of styrene followed immediately by 0.380 mL of toluene, were injected into the prepressurized reaction vessel. Then, 0.088 mL (0.55 µmol) of the "activator solution" was added to the 1 mL vial. After the time period $t_2$ elapsed, a fraction (as indicated in table 56) of the total 1 mL vial contents, followed immediately by approximately 0.3 mL of toluene were injected into the reaction vessel. The array of experiments is described in table 56.

Polymerization: The polymerization reaction was allowed to continue for the the time shown in table 56A, during which time the temperature and pressure were maintained at their pre-set levels by computer control. The polymerization times were the lesser of the maximum desired polymerization reaction time or the time taken for a predetermined amount of monomer gas to be consumed in the polymerization reaction. After the reaction time elapsed, the reaction was quenched by addition of an overpressure of carbon dioxide.

Product work up: ethylene/styrene copolymerizations After the polymerization reaction, the glass vial insert, containing the polymer product and solvent, was removed from the pressure cell and removed from the inert atmosphere dry box, and the volatile components were removed using a centrifuge vacuum evaporator. After most of the volatile components had evaporated, the vial contents were dried thoroughly by evaporation at elevated temperature under reduced pressure. The vial was then weighed to determine the yield of polymer product. The polymer product was then analyzed by rapid GPC, as described above to determine the molecular weight of the polymer produced, and by FTIR spectroscopy to determine the styrene incorporation. Results are presented in the tables 57–59.

TABLE 56

Description of polymerization experiments using complexes 7–10 for examples 23.A.1.–23.H.3.

|   | 1 | 2 | 3 | group 13 reagent[a] |
|---|---|---|---|---|
| A | C 7 | C 7 | C 7 | 30 |
| B | C 7 | C 7 | C 7 | 10 |
| C | C 8 | C 8 | C 8 | 30 |
| D | C 8 | C 8 | C 8 | 10 |
| E | C 9 | C 9 | C 9 | 30 |
| F | C 9 | C 9 | C 9 | 10 |
| G | C 10 | C 10 | C 10 | 30 |
| H | C 10 | C 10 | C 10 | 10 |
| Injection Fraction | 0.25 | 0.25 | 0.25 |   |
| Polym. Temp. (° C.) | 110 | 110 | 110 |   |
| Premix temp. (° C.) | 24 | 50 | 50 |   |
| group 13 reagent[c] | DIBAL | DIBAL | TMA |   |
| group 13 reagent[b] | DIBAL | DIBAL | TMA |   |
| Activator | ABF20 | ABF20 | ABF20 |   |

[a] Number of equivalents of group 13 reagent added to Metal Complex as described in activation steps
[b] Group 13 reagent, which was placed in reaction vessel prior of catalyst injection (0.02 M solution was used).
[c] Identity of group 13 reagent added to Metal Complex as described in activation steps

TABLE 56A

Polymerization times in seconds for examples 23.A.1.–23.H.3.

|   | 1 | 2 | 3 |
|---|---|---|---|
| A | 720 | 337 | 305 |
| B | 901 | 749 | 900 |
| C | 353 | 259 | 284 |
| D | 900 | 840 | 902 |
| E | 760 | 265 | 281 |
| F | 902 | 901 | 901 |
| G | 582 | 300 | 492 |
| H | 902 | 902 | 883 |

TABLE 57

Activity (mg polymer per minute per µmol) of examples 23.A.1.-23.H.3.

|   | 1 | 2 | 3 |
|---|---|---|---|
| A | 186 | 386 | 453 |
| B | 129 | 180 | 126 |
| C | 346 | 457 | 413 |

TABLE 57-continued

Activity (mg polymer per minute per μmol) of examples 23.A.1.-23.H.3.

|   | 1 | 2 | 3 |
|---|---|---|---|
| D | 122 | 155 | 117 |
| E | 188 | 524 | 492 |
| F | 127 | 139 | 129 |
| G | 244 | 467 | 276 |
| H | 125 | 144 | 143 |

TABLE 58

Styrene incorporation (mol %) of examples 23.A.1.-23.H.3.

|   | 1 | 2 | 3 |
|---|---|---|---|
| A | 3.1 | 3.7 | 3.6 |
| B | 3.8 | 4.5 | 4.9 |
| C | 2.5 | 3.1 | 2.9 |
| D | 2.8 | 3.6 | 3.7 |
| E | 3.5 | 4.1 | 3.5 |
| F | 3.9 | 4.6 | 4.4 |
| G | 3.1 | 3.8 | 3.3 |
| H | 3.9 | 4.8 | 4.3 |

TABLE 59

Weight average molecular weight (k) of examples 23.A.1.-23.H.3.

|   | 1 | 2 | 3 |
|---|---|---|---|
| A | 322 | 255 | 311 |
| B | 512 | 571 | 987 |
| C | 334 | 253 | 233 |
| D | 530 | 384 | 577 |
| E | 645 | 270 | 274 |
| F | 464 | 652 | 762 |
| G | 301 | 214 | 256 |
| H | 176 | 512 | 743 |

Example 24

Ethylene-Styrene Copolymerization Using Metal Complexes 17, 18, 19 and 20 (C17, C18, C19, C20) at Different Activation Conditions Sixteen polymerization reactions were run with different metal complexes and activating conditions for copolymerization of ethylene and styrene.

Preparation of the polymerization reactor prior to injection of catalyst composition: A pre-weighed glass vial insert and disposable stirring paddle were fitted to each reaction vessel of the reactor. The reactor was then closed, 0.050 mL of a 0.02 M group 13 reagent solution in toluene and 4.55 mL of toluene were injected into each pressure reaction vessel through a valve. The identity of the group 13 reagent solution is given in table 60. The temperature was then set to 110° C., and the stirring speed was set to 600 rpm, and the mixture was exposed to ethylene at 100 psi pressure. An ethylene pressure of 100 psi in the pressure cell and the temperature setting were maintained, using computer control, until the end of the polymerization experiment.

Preparation of the group 13 reagent and activator stock solutions: The "activator solution" is a 5 mM solution of N,N'-dimethylanilinium tetrakis (pentafluorophenyl) borate in toluene ("ABF20"). The solution is heated to approximately 85° C. to dissolve the reagent. The group 13 reagent solution is a 0.2 M solution of triisobutylaluminium ("TIBA").

Activation and Injection of solutions into the pressure reactor vessel: First, 0.200 mL of the metal complex solution (5 mM in toluene) was dispensed in a 1 mL vial. Then, an appropriate amount of the 0.2 M group 13 reagent solution was added. This mixture was held for 75 seconds, during which time, 0.500 mL of styrene followed immediately by 0.500 mL of toluene, and 0.100 mL of the "activator solution" followed immediately by 0.400 mL of toluene were injected into the prepressurized reaction vessel. Then, half of the total 1 mL vial contents, followed immediately by approximately 0.3 mL of toluene were injected into the reaction vessel. The array of experiments is described in table 60.

Polymerization: The polymerization reaction was allowed to continue for the times shown in table 60A, during which time the temperature and pressure were maintained at their pre-set levels by computer control. The polymerization times were the lesser of the maximum desired polymerization reaction time or the time taken for a predetermined amount of monomer gas to be consumed in the polymerization reaction. After the reaction time elapsed, the reaction was quenched by addition of an overpressure of carbon dioxide.

Product work up: ethylene/styrene copolymerizations: This part of this example was performed as described in example 23. Results are presented in the tables 61–63.

TABLE 60

Description of polymerization experiments using complexes 7–10 (examples 24.A.1-24.H.2):

|   | 1 | 2 |
|---|---|---|
| A | C 17 | C 17 |
| B | C 17 | C 17 |
| C | C 18 | C 18 |
| D | C 18 | C 18 |
| E | C 19 | C 19 |
| F | C 19 | C 19 |
| G | C 20 | C 20 |
| H | C 20 | C 20 |
| Polym. Temp. (° C.) | 110 | 110 |
| group 13 reagent[a] | 5 TIBA | 10 TIBA |
| group 13 reagent[b] | TIBA | TIBA |
| Activator | ABF20 | ABF20 |

[a]Number of equivalents and identity of group 13 reagent added to Metal Complex as described in activation steps
[b]Group 13 reagent, which was placed in reaction vessel prior of catalyst injection (0.02 M solution was used).

TABLE 60A

Polymerization times in seconds for examples 24.A.1-24.H.2

|   | 1 | 2 |
|---|---|---|
| A | 900 | 900 |
| B | 900 | 900 |
| C | 900 | 900 |
| D | 900 | 900 |
| E | 639 | 408 |
| F | 670 | 464 |
| G | 900 | 743 |
| H | 900 | 797 |

TABLE 61

Activity (mg polymer per minute per μmol) of examples 24.A.1-24.H.2

|   | 1 | 2 |
|---|---|---|
| A | 21 | 23 |
| B | 22 | 22 |
| C | 20 | 23 |
| D | 21 | 22 |
| E | 43 | 61 |
| F | 41 | 57 |
| G | 28 | 44 |
| H | 29 | 41 |

TABLE 62

Styrene incorporation (mol %) of examples 24.A.1-24.H.2

|   | 1 | 2 |
|---|---|---|
| A | 3.1 | 3.3 |
| B | 3.2 | 3.4 |
| C | 4.3 | 3.6 |
| D | 3.6 | 3.8 |
| E | 3.9 | 3.3 |
| F | 4.1 | 3.3 |
| G | 5.5 | 4.7 |
| H | 5.2 | 5.1 |

TABLE 63

Weight average molecular weight (k) of examples 24.A.1-24.H.2

|   | 1 | 2 |
|---|---|---|
| A | 50 | 42 |
| B | 62 | 36 |
| C | 79 | 34 |
| D | 80 | 47 |
| E | 118 | 49 |
| F | 116 | 52 |
| G | 549 | 259 |
| H | 422 | 226 |

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purposes.

What is claimed is:

1. A process for the production of an ethylene-isobutylene copolymer, comprising forming a reaction mixture of at least ethylene, isobutylene and a catalyst and subjecting the reaction mixture to polymerization conditions, wherein said catalyst comprises:

(1) a ligand represented by the general formula:

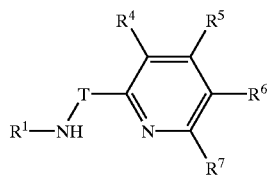

wherein
$R^1$ is selected from the group consisting of aryl and substituted aryl;
T is —$Cr^2R^3$— and $R^2$ are $R^3$ are independently selected from the group consisting of hydrogen, alkyl, substituted alkyl, cycloalkyl, substituted cycloalkyl, heteroalkyl, substituted heteroalkyl, heterocycloalkyl, substituted hetercycloalkyl, aryl, substituted aryl, heteroaryl, substituted heteroaryl, alkoxyl, aryloxyl, silyl, boryl, phosphino, amino, thio, seleno, halide, nitro, and combinations thereof; and optionally, any combination of $R^1$, $R^2$, and $R^3$ may be joined together in a ring structure;
$R^4$, $R^5$, $R^6$ and $R^7$ are each hydrogen;

(2) a metal precursor compound characterized by the general formula $Hf(L)_n$ wherein each L is independently selected from the group consisting of halide, alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, hydroxy, boryl, silyl, amino, amine, hydrido, allyl, diene, seleno, phosphino, phosphine, carboxylates, thio, 1,3-dionates, oxalates, carbonates, nitrates, sulphates, ethers, thioethers and combinations thereof or optionally two or more L groups are joined into a ring structure; n is 1, 2, 3, 4, 5, or 6;

(3) optionally, at least one activator; and (4) optionally, a trialkyl aluminum compound.

2. A process of claim 1, wherein said polymerization wherein $R^3$ is selected from the group consisting of substituted alkyl, aryl and substituted aryl.

3. The process of claim 2, wherein a trialkyl aluminum compound is present.

4. The process of claim 3, wherein said said trialkyl aluminum compound is triethylaluminum.

5. The process of claim 3, wherein said triethylaluminum is present in an amount of at least 0.1 equivalents to the metal precursor compound.

6. The process of claim 3 wherein said triethylaluminum is present in an amount of between 1 and 10 equivalents to the metal precursor compound.

7. The process of claim 1, wherein an activator is present.

8. The process of claim 5, wherein said activator is an ion forming compound comprising boron.

9. The process of claim 1, wherein said ligand is selected from the group consisting of:

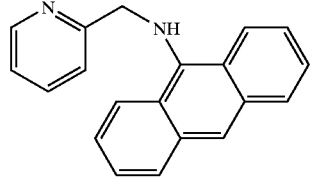

-continued
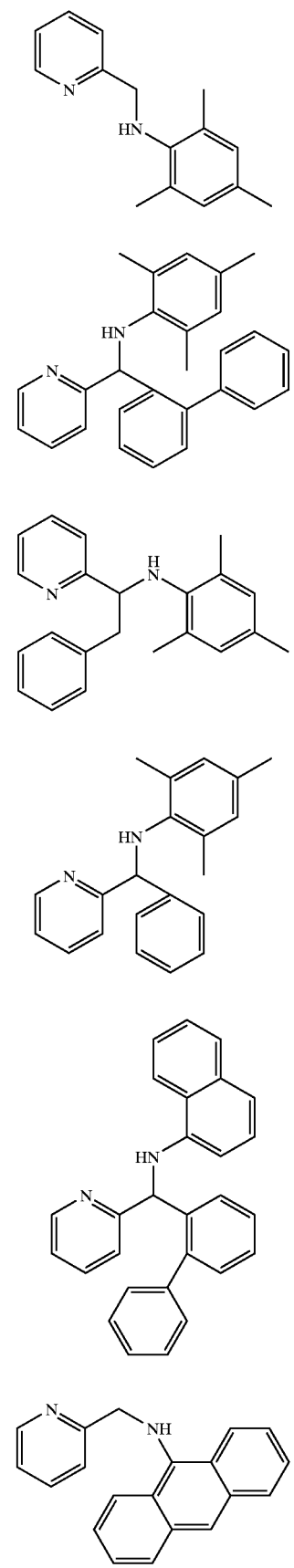
-continued
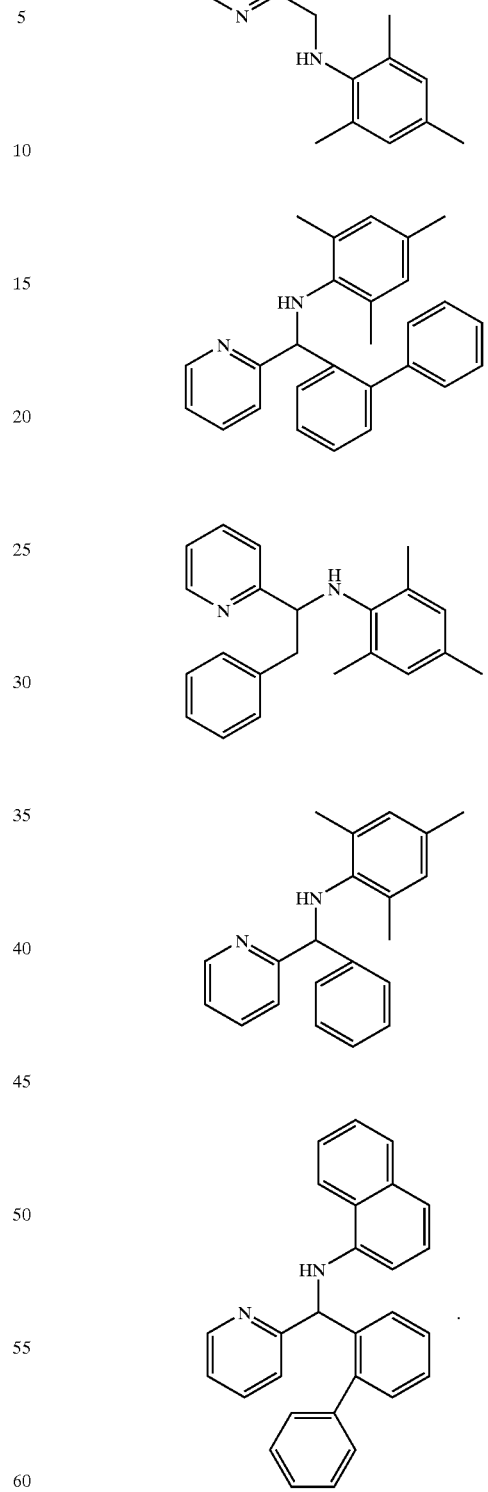
10. The process of claim 1, wherein the ligand is mixed with the metal precursor prior to, or while contacting said ethylene and isobutylene.
* * * * *

UNITED STATES PATENT AND TRADEMARK OFFICE
CERTIFICATE OF CORRECTION

PATENT NO.   : 6,828,397 B2
DATED        : December 7, 2004
INVENTOR(S)  : Boussie et al.

It is certified that error appears in the above-identified patent and that said Letters Patent is hereby corrected as shown below:

Column 146,
Line 18, delete "hetercycloalkyl," and insert -- heterocycloalkyl --

Signed and Sealed this

Fifteenth Day of March, 2005

JON W. DUDAS
*Director of the United States Patent and Trademark Office*